US011666628B2

(12) United States Patent
Laporte et al.

(10) Patent No.: US 11,666,628 B2
(45) Date of Patent: Jun. 6, 2023

(54) COMPOSITIONS AND METHOD FOR THE TREATMENT OF X-LINKED CENTRONUCLEAR MYOPATHY

(71) Applicants: UNIVERSITE DE STRASBOURG, Strasbourg (FR); INSTITUT NATIONAL DE LA SANTE ET DE LA RECHERCHE MEDICALE, Paris (FR); CENTRE NATIONAL DE LA RECHERCHE SCIENTIFIQUE, Paris (FR)

(72) Inventors: Jocelyn Laporte, Strasbourg (FR); Valentina Lionello, Gerenzano (IT); Belinda Cowling, Kaltenhouse (FR)

(73) Assignees: UNIVERSITE DE STRASBOURG, Strasbourg (FR); INSTITUT NATIONAL DE LA SANTE ET DE LA RECHERCHE MEDICALE, Paris (FR); CENTRE NATIONAL DE LA RECHERCHE SCIENTIFIQUE, Paris (FR)

( * ) Notice: Subject to any disclaimer, the term of this patent is extended or adjusted under 35 U.S.C. 154(b) by 0 days.

(21) Appl. No.: 16/762,953

(22) PCT Filed: Nov. 12, 2018

(86) PCT No.: PCT/EP2018/080964
§ 371 (c)(1),
(2) Date: May 11, 2020

(87) PCT Pub. No.: WO2019/092251
PCT Pub. Date: May 16, 2019

(65) Prior Publication Data
US 2020/0405804 A1 Dec. 31, 2020

(30) Foreign Application Priority Data
Nov. 11, 2017 (EP) ..................... 17306566

(51) Int. Cl.
*A61K 38/16* (2006.01)
*A61P 21/00* (2006.01)

(52) U.S. Cl.
CPC .............. *A61K 38/16* (2013.01); *A61P 21/00* (2018.01)

(58) Field of Classification Search
CPC .... A61K 38/1703; A61K 38/16; A61K 48/00; A61K 48/0016; A61K 48/005
See application file for complete search history.

(56) References Cited

U.S. PATENT DOCUMENTS

2016/0264976 A1   9/2016   Laporte et al.

OTHER PUBLICATIONS

Wechsler-Reya et al. "Structural Analysis of the Human B1N1 Gene: Evidence for Tissue-Specific Transcriptional Regulation and Alternative RNA Splicing", Journal of Biological Chemistry, 1997, 31453-31458 (Year: 1997).*
U.S National Library of Medicine, "Help Me Understand Genetics: Gene Therapy and Other Medical Advances", Reprinted from MedlinePlus Genetics, Available from: https://medlineplus.gov/; accessed on May 6, 2022. (Year: 2022).*
Childers et al. "Gene Therapy Prolongs Survival and Restores Function in Murine and Canine Models of Myotubular Myopathy", Science Translational Medicine, 2014, 16 pages (Year: 2014).*
Cowling et al., "Reducing dynamin 2 expression rescues X-linked centronuclear myopathy", The Journal of Clinical Investigation, 2014, 1350-1363 (Year: 2014).*
Bohm, L. et al. "Case report of intrafamilial variability in autosomal recessive centronuclear myopathy associated to a novel *BIN1* stop mutation" *Orphanet Journal of Rare Diseases*, Dec. 3, 2010, pp. 1-6, vol. 5, No. 35.
Husta Butler, M. et al. "Amphiphysin II (SH3P9; BIN1), a Member of the Amphiphysin/Rvs Family, is Concentrated in the Cortical Cytomatrix of Axon Initial Segments and Nodes of Ranvier in Brain and around T Tubules in Skeletal Muscle" *The Journal of Cell Biology*, Jun. 16, 1997, pp. 1355-1367, vol. 137, No. 6.
Lee, E. et al. "Amphiphysin 2 (Bin1) and T-Tubule Biogenesis in Muscle" *Science*, Aug. 16, 2002, pp. 1193-1196, vol. 297, No. 5584.
Prokic, I. et al. "Amphiphysin 2 (BIN1) in physiology and diseases" *J Mol Med*, 2014, pp. 453-463, vol. 92, No. 5.
Sakamuro, D. et al. "BIN1 is a novel MYC-interacting protein with features of a tumour suppressor" *Nature Genetics*, Sep. 1996, pp. 69-77, vol. 14.
Wechsler-Reya, R. et al. "Structural Analysis of the Human *BIN1* Gene; Evidence for Tissue-Specific Transcriptional Regulation and Alternate RNA Splicing" *The Journal of Biological Chemistry*, Dec. 12, 1997, pp. 31453-31458, vol. 272, No. 50.
Written Opinion in International Application No. PCT/EP2018/080964, dated Feb. 12, 2019, pp. 1-7.

* cited by examiner

*Primary Examiner* — Lianko G Garyu
(74) *Attorney, Agent, or Firm* — Saliwanchik, Lloyd & Eisenschenk

(57) ABSTRACT

The present disclosure relates to a BIN1 protein or a BIN1 nucleic acid sequence producing or encoding the same, for a use in the treatment of X-linked centronuclear myopathy. The present invention provides compositions and methods for treatment of X-linked centronuclear myopathy. The present invention relates to a method of delivering the BIN1 polypeptide to subjects with X-linked centronuclear myopathy.

11 Claims, 9 Drawing Sheets
Specification includes a Sequence Listing.

COMPOSITIONS AND METHOD FOR THE TREATMENT OF X-LINKED CENTRONUCLEAR MYOPATHY

CROSS-REFERENCE TO RELATED APPLICATION

This application is the U.S. national stage application of International Patent Application No. PCT/EP2018/080964, filed Nov. 12, 2018.

The Sequence Listing for this application is labeled "Seq-List-replace-2.txt" which was created on May 12, 2021 and is 39 KB. The entire content of the sequence listing is incorporated herein by reference in its entirety.

FIELD OF THE INVENTION

The present disclosure relates to a BIN1 protein or a BIN1 nucleic acid sequence producing or encoding the same, for a use in the treatment of X-linked centronuclear myopathy. The present invention provides compositions and methods for treatment of X-linked centronuclear myopathy. The present invention relates to a method of delivering the BIN1 polypeptide to subjects with X-linked centronuclear myopathy.

BACKGROUND OF THE INVENTION

Centronuclear Myopathies (CNM) are a group of congenital myopathies characterized by muscle weakness and confirmed histologically by fiber atrophy, predominance of type I fibers, and increased centralization of nuclei, not secondary to muscle regeneration. Among the three main characterized forms of CNM, X-linked centronuclear myopathy (also called XLCNM, myotubular myopathy— XLMTM, or OMIM 310400) is the most common and severe form of CNM, with neonatal onset and death often occurring in the first years of life (Jungbluth, H. et al., Orphanet J Rare Dis, 2008. 3: p. 26). Survival beyond the postnatal period requires intensive support, often including gastrostomy feeding and mechanical ventilation. There is currently no cure, nor effective treatments available for this disorder.

XLCNM is due to mutations in the phosphoinositides phosphatase myotubularin (MTM1) (Laporte, J. et al., Nature Genetics, 1996. 13(2): p. 175-82). To date more than 200 different mutations in MTM1 have been reported in about 450 families, most of which lead to a strong reduction of protein. Mtm1 knockout or knockin mice have previously been characterized, which recapitulate the CNM phenotype with classical histological features including abnormal organelle positioning, mislocalization of nuclei and muscle atrophy, associated with a corresponding reduction in muscle strength (Buj-Bello A, Laugel V, Messaddeq N, Zahreddine H, Laporte J, Pellissier J F, Mandel J L., The lipid phosphatase myotubularin is essential for skeletal muscle maintenance but not for myogenesis in mice, Proc Natl Acad Sci USA. 2002 Nov. 12; 99(23):15060-5. Epub 2002 Oct 21; Pierson C R, Dulin-Smith A N, Durban A N, Marshall M L, Marshall J T, Snyder A D, Naiyer N, Gladman J T, Chandler D S, Lawlor M W, Buj-Bello A, Dowling J J, Beggs A H., Hum Mol Genet. 2012 Feb. 15; 21(4):811-25. doi: 10.1093/hmg/ddr512. Epub 2011 Nov. 7; Mol Cell Biol. 2013 January; 33(1):98-110. doi: 10.1128/MCB.01075-12. Epub 2012 Oct 29. Defective autophagy and mTORC1 signaling in myotubularin null mice. Fetalvero K M, Yu Y, Goetschkes M, Liang G, Valdez R A, Gould T, Triantafellow E, Bergling S, Loureiro J, Eash J, Lin V, Porter J A, Finan P M, Walsh K, Yang Y, Mao X, Murphy L O). A defect in triads structure associated with abnormal excitation-contraction coupling has been detected in several animal models and patients with different forms of CNM, identifying a common defect in all CNM forms (Toussaint A. et al., Acta Neuropathol. 2011 February; 121(2):253-66). This is consistent with a proposed role of MTM1 in the regulation of phosphoinositides level on the sarcoplasmic reticulum component of the triads.

MTM1 has an important role in membrane remodeling and in Beta1 Integrin recycling. Beta1 integrin is part of the focal adhesion complex that allows to maintain muscle fibers adherent when they are exposed to mechanical stress. In XLCNM muscle patient, it has been observed abnormalities on Beta1 integrin localization compared to wild type (Ribeiro et al., Phosphoinositide regulation of integrin trafficking required for muscle attachment and maintenance., PLoS Genet. 2011 Feb. 10; 7(2):e1001295. doi: 10.1371/journal.pgen.1001295. PMID:2134728). Ribeiro et al. showed that the depletion of MTM1 in *Drosophila* muscle causes issues in Beta1 Integrin recycling (Ribeiro et al. 2011). Further analysis showed that XLCNM patient fibroblasts have an increase of Beta1 Integrin that is blocked in the early endosomal vesicle (Ketel et al. 2016 A phosphoinositide conversion mechanism for exit from endosomes. Nature. 2016 Jan. 21; 529(7586):408-12. doi: 10.1038/nature16516. Epub 2016 Jan. 13. PMID: 26760201).

BIN1 (i.e., Bridging INtegrator 1) encodes for Amphiphysin 2 and mutations in this gene can cause CNM, and more particularly autosomal recessive CNM (also named ARCNM). BIN1 is ubiquitously expressed and it is essential for endocytosis, membrane recycling and remodeling. There are various tissue-specific isoforms of BIN1, among them, the skeletal muscle specific is the isoform 8 which contain a phosphoinositides (PI) binding domain. This domain increases the affinity of BIN1 to the PtdIns4,5P$_2$, PtdIns5P and PtdIns3P, in vitro studies have demonstrated the involvement of this domain on creating membrane tubules that resemble the T tubule in skeletal muscle (Lee et al. Amphiphysin 2 (Bin1) and T-tubule biogenesis in muscle. Science. 2002 Aug. 16; 297(5584):1193-6. PMID: 12183633). It has been shown that MTM1 and BIN1 interact and this interaction is crucial for membrane tubulation (Royer et al. The myotubularin-amphiphysin 2 complex in membrane tubulation and centronuclear myopathies. EMBO Rep. 2013 October; 14(10):907-15. doi: 10.1038/embor.2013.119. Epub 2013 Aug. 6. PMID: 23917616). However, no link has shown that BIN1 and MTM1 are part of a common pathway in vivo.

Here, it is demonstrated that overexpression of BIN1 is sufficient to completely rescue the XLCNM phenotype and that BIN1 and MTM1 are both involved in Beta1 integrin recycling. Overexpression of BIN1 can thus rescue the myopathy displayed by Mtm1KO mice, which makes such overexpression an effective therapy for the treatment of XLCNM.

SUMMARY OF THE INVENTION

The present disclosure provides methods and compositions for treating XLCNM by overexpression of BIN1. The present invention provides compositions and methods for treatment of XLCNM, in a subject in need thereof.

The present invention relates to a method of expressing BIN1 to subjects with XLCNM. The compositions and methods of the present invention can increase muscle strength and/or improve muscle function and/or rescue histological features in a subject with XLCNM.

In one embodiment, the present invention is useful for treating an individual with XLCNM. In particular, the present invention relates to an Amphiphysin 2 polypeptide or a BIN1 nucleic acid sequence, for a use in the treatment of XLCNM. In other words, the invention relates to the use of an Amphiphysin 2 polypeptide or a BIN1 nucleic acid sequence, for the preparation of a medicament for the treatment of XLCNM. More specifically, the invention relates to a method for treating XLCNM in a subject in need thereof, comprising administering to said subject a therapeutically effective amount of an Amphiphysin 2 polypeptide or a BIN1 nucleic acid sequence. Indeed, the present invention improves muscle function and prolongs survival in afflicted subjects.

In a particular aspect, the present invention concerns a composition comprising Amphiphysin 2 polypeptide or a nucleic acid sequence producing or encoding such polypeptide, such as BIN1. Said composition can be for use in the treatment of XLCNM.

The present invention also provides isolated polypeptides comprising Amphiphysin 2 protein, as well as pharmaceutical compositions comprising Amphiphysin 2 protein in combination with a pharmaceutical carrier.

The present invention also deals with an isolated nucleic acid sequence comprising at least one BIN1 nucleic acid sequence, or an expression vector comprising such nucleic acid sequence comprising at least one BIN1 nucleic acid sequence, as well as pharmaceutical compositions comprising the same in combination with a pharmaceutical carrier.

Further, the present invention relates to methods of making such Amphiphysin 2 or constructs comprising at least one BIN1 nucleic acid sequence.

Additionally, disclosed herein are methods of using Amphiphysin 2 polypeptide or expression vector comprising at least one BIN1 nucleic acid sequence, for the treatment of XLCNM.

These and other objects and embodiments of the invention will become more apparent after the detailed description of the invention.

BRIEF DESCRIPTION OF THE DRAWINGS

FIG. 5: MTM1 is essential for Beta1 integrin trafficking and focal adhesion functions in mammalian muscle. Mtm1 mice have mis-localized Beta1 Integrin. BIN1 isoform 8 of sequence SEQ ID NO: 27 has been used herein. (A). Transversal WT and Mtm1−/y TA muscle stained for Dystrophin. Scale bar 10 μm. (B) Model of focal adhesion in skeletal muscle (C) Transversal WT and Mtm1−/y TA muscle immunofluorescence stained for the extracellular matrix protein Laminin. Scale bar 10 μm (D) Transversal WT and Mtm1−/y TA muscle immunofluorescence stained for the extracellular matrix protein Collagen. Scale bar 10 μm (E) Transversal WT and Mtm1−/y TA muscle immunofluorescence probed anti Vinculin and Beta1 Integrin. Scale bar 10 μm (F). Transversal WT and Mtm1−/y TA muscle sections stained for EEA1 and Beta1 Integrin. Arrows point to abnormal intracellular accumulation of Beta1 Integrin on EEA-1 positive endosomes. Scale bar 10 μm and 1 μm (zoom) (G). Western Blot of WT and Mtm1−/y TA muscle (5 weeks old mice) probed with anti-Beta Integrin, anti-MTM1 and anti-GAPDH antibodies (left panel). Beta1 Integrin level fold expression normalized on GAPDH (right panel). (H) Comparison of transversal muscle sections from a control human skeletal muscle with X-linked centronuclear myopathy patient (mutation c.141-144delAGAA p.Glu48LeufsX24 in MTM1. Scale bar 20 μm. (I) 8 weeks WT and Mtm1−/y TA muscle stained with Masson trichrome. Scale bar 10 μm. (J) WT and Mtm1−/y primary myoblasts probed for Beta1 Integrin. Scale bar 10 μm. (K) Western Blot of WT and Mtm1−/y TA muscle (5 weeks old mice) probed with anti-FAK and anti-p-FAK (Tyr397) antibodies. (L) Quantification of FAK normalized on TCE and (M), quantification of p-FAK (Tyr397) on total FAK. (N) Adhesion assay: adherent surface of primary myoblasts at different timepoints after plating (n≥25 from n>=2 mice). (O) Migration assay: distance (μm) migrated by WT and Mtm1−/y myoblasts during 24 hours (n≥0 from n=3 mice). (P) Fusion index: number of nuclei in WT and Mtm1−/y myotubes at 3 times point after differentiation was started (24, 48, 72 hours) (n>36 from n>=2 mice). Statistic test: T-test; ns: not significant, *p<0.05,  p<0.01, *p<0.001.

Figure 6:
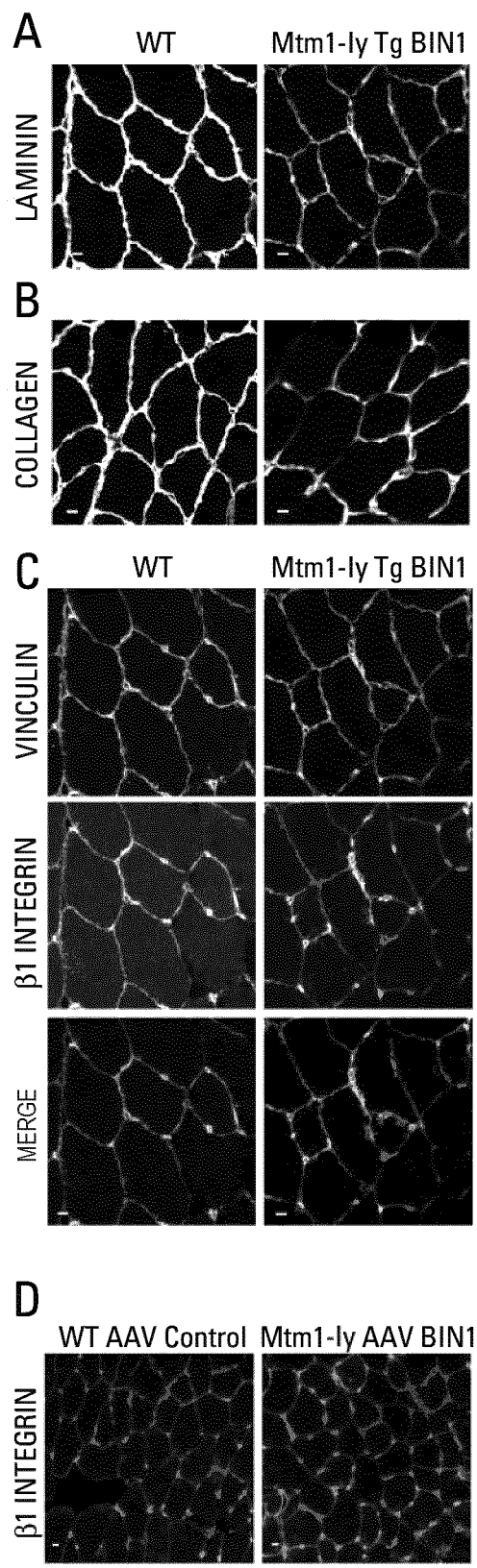
Figure 6:
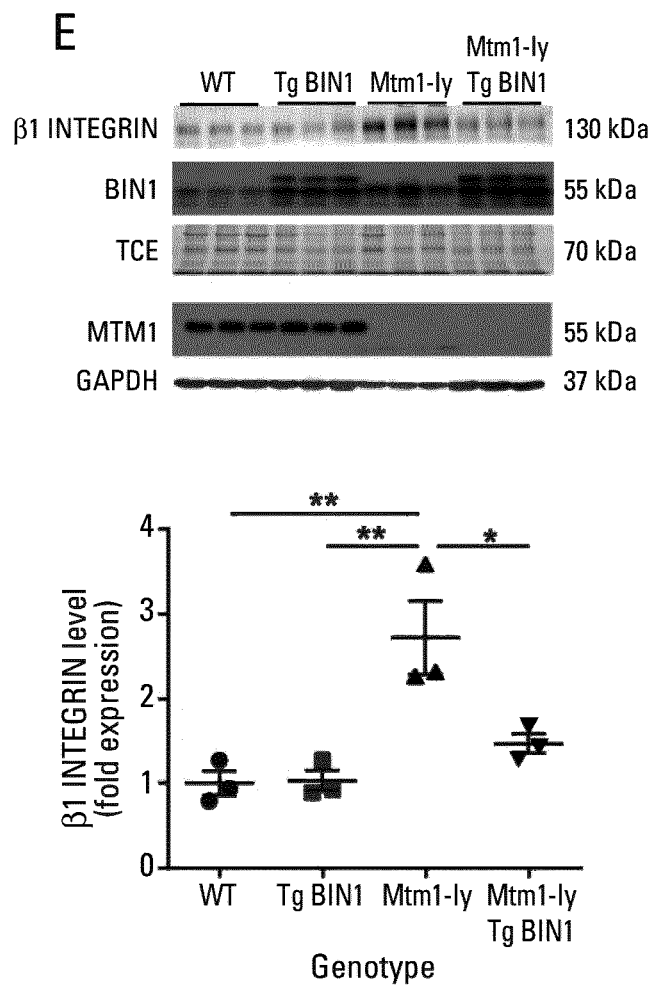
Figure 6:
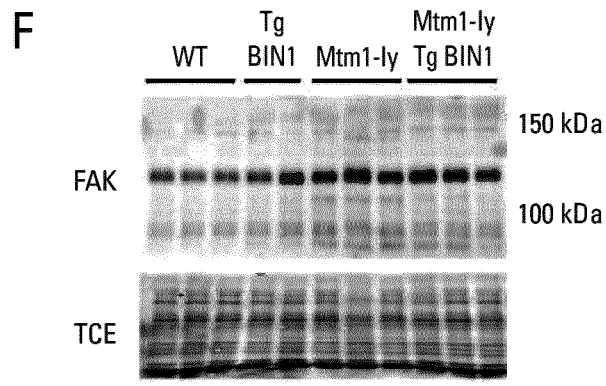
Figure 6:
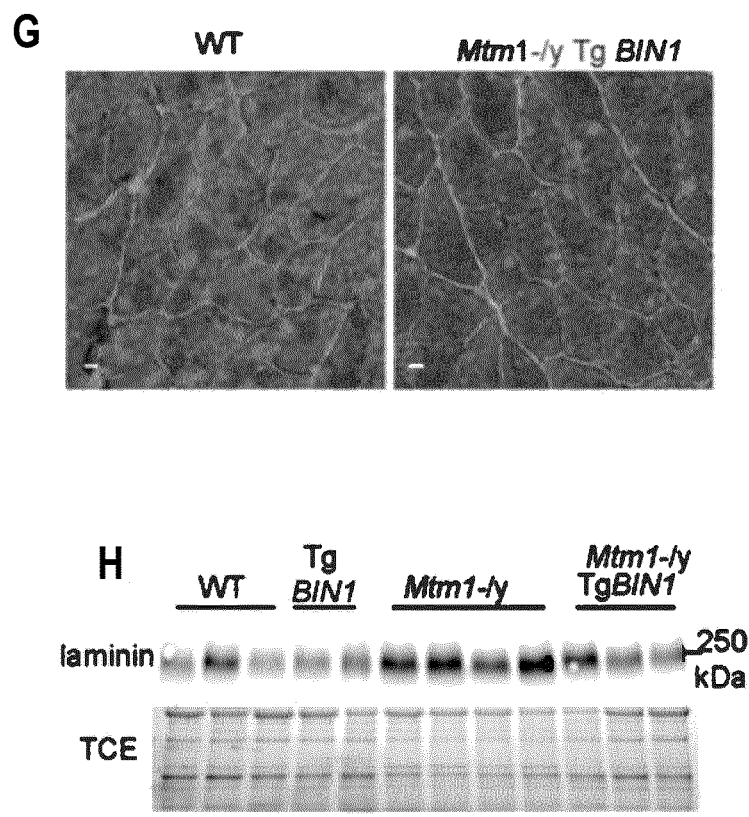

FIG. 6: Overexpression of BIN1 rescues Beta1 Integrin level and focal adhesion in the Mtm1−/y mice muscle. BIN1 isoform 8 of sequence SEQ ID NO: 27 has been used herein. (A) Transversal 8-weeks WT and Mtm1−/y TgBIN1 TA muscle sections immunofluorescence stained for the extracellular matrix protein Laminin. Scale bar 10 μm. (B) Transversal 8-weeks WT and Mtm1−/y TgBIN1 TA muscle sections immunofluorescence stained for the extracellular matrix protein Collagen. Scale bar 10 μm. (C) Transversal TA muscle probed with anti-Vinculin and anti-Beta1 Integrin antibodies. Scale bar 10 μm. (D) Transversal TA muscle of WT mice injected systemically with AAV empty as Control and of Mtm1−/y mice injected systemically with AAV BIN1, probed with anti-Beta1 Integrin antibody. Scale bar 10 μm. (E)Western blot probed for Beta1 Integrin, BIN1 and MTM1 (top panel). Quantification of Beta1 Integrin normalized to TCE of the same gel (bottom panel). (F) Western blot probed for FAK and TCE picture of the blot as loading control. (G) Transversal 8-weeks WT and Mtm1−/y TgBIN1 TA muscle sections stained with trichrome Masson staining. Scale bar 10 μm. (H) Western-blot probed with anti-Laminin antibodies (top panel). Quantification of Laminin normalized on TCE (bottom panel). Statistic test: One-Way Anova, Bonferroni post-hoc test; ns: not significant, *p<0.05, ** p<0.01.

DETAILED DESCRIPTION

Unless otherwise defined, all technical and scientific terms used herein have the same meaning as commonly understood by one of ordinary skill in the art to which this invention belongs.

The articles "a" and "an" are used herein to refer to one or to more than one (i.e., to at least one) of the grammatical object of the article. By way of example, "an element" means one element or more than one element.

"About" or "around" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods or compositions.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

According to the invention, the term "comprise(s)" or "comprising" (and other comparable terms, e.g., "containing," and "including") is "open-ended" and can be generally interpreted such that all of the specifically mentioned features and any optional, additional and unspecified features are included. According to specific embodiments, it can also be interpreted as the phrase "consisting essentially of" where the specified features and any optional, additional and unspecified features that do not materially affect the basic and novel characteristic(s) of the claimed invention are included or the phrase "consisting of" where only the specified features are included, unless otherwise stated.

The terms "polypeptide," "peptide" and "protein" are used interchangeably herein to refer to a polymer of amino acid residues covalently linked by peptide bonds. The terms apply to amino acid polymers in which one or more amino acid residue is an artificial chemical mimetic of a corresponding naturally occurring amino acid, as well as to naturally occurring amino acid polymers and non-naturally occurring amino acid polymers. "Polypeptides" include, for example, biologically active fragments, substantially homologous polypeptides, oligopeptides, homodimers, heterodimers, variants of polypeptides, modified polypeptides, derivatives, analogues, fusion proteins, among others. The polypeptides include natural peptides, recombinant peptides, synthetic peptides, or a combination thereof.

As used herein, "treating a disease or disorder" means reducing the frequency with which a symptom of the disease or disorder is experienced by a patient. Disease and disorder are used interchangeably herein. To "treat" a disease as the term is used herein, means to reduce the frequency or severity of at least one sign or symptom of a disease or disorder experienced by a subject. Within the context of the invention, the term treatment denotes curative, symptomatic, and preventive treatment. As used herein, the term "treatment" of a disease refers to any act intended to extend life span of subjects (or patients) such as therapy and retardation of the disease progression. The treatment can be designed to eradicate the disease, to stop the progression of the disease, and/or to promote the regression of the disease. The term "treatment" of a disease also refers to any act intended to decrease the symptoms associated with the disease, such as hypotonia and muscle weakness. More specifically, the treatment according to the invention is intended to delay the appearance of or revert XLCNM phenotypes or symptoms, ameliorate the motor and/or muscular behavior and/or lifespan.

A disease or disorder is "alleviated" if the severity of a symptom of the disease or disorder, the frequency with which such a symptom is experienced by a patient, or both, is reduced. A "therapeutic" treatment is a treatment administered to a subject who exhibits signs of pathology, for the purpose of diminishing or eliminating at least one or all of those signs.

The phrase "therapeutically effective amount," as used herein, refers to an amount that is sufficient or effective to prevent or treat (delay or prevent the onset of, prevent the progression of, inhibit, decrease or reverse) a disease or disorder, including provision of a beneficial effect to the subject or alleviating symptoms of such diseases.

The terms "patient," "subject," "individual," and the like are used interchangeably herein, and refer to any animal, or cells thereof whether in vitro or in situ, amenable to the methods described herein. In certain non-limiting embodiments, the patient, subject or individual is a human. Preferably the subject is a human patient whatever its age or sex. New-borns, infants, children are included as well.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

"Expression vector" refers to a vector comprising a recombinant polynucleotide comprising expression control sequences operatively linked to a nucleotide sequence to be expressed, which can be referred herein as a construct. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses (e.g., lentiviruses, retroviruses, adenoviruses, and adeno-associated viruses) that incorporate the recombinant polynucleotide. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, adenoviral vectors, adeno-associated virus vectors, retroviral vectors, and the like. The construct is therefore incorporated into an expression vector.

"Homologous" refers to the sequence similarity or sequence identity between two polypeptides or between two nucleic acid molecules. When a position in both of the two compared sequences is occupied by the same base or amino acid monomer subunit, e.g., if a position in each of two DNA molecules is occupied by adenine, then the molecules are homologous at that position. The percent of homology between two sequences is a function of the number of matching or homologous positions shared by the two sequences divided by the number of positions compared× 100. For example, if 6 of 10 of the positions in two sequences are matched or homologous then the two sequences are 60% homologous. By way of example, the DNA sequences ATTGCC and TATGGC share 50% homology. Generally, a comparison is made when two sequences are aligned to give maximum homology. The "% of homology" between two nucleotide (or amino acid) sequences can be determined upon alignment of these sequences for optimal comparison. Optimal alignment of sequences may be herein preferably conducted by a global homology alignment algorithm should the alignment be performed using sequences of the same or similar length, such as by the algorithm described by Needleman and Wunsch (Journal of Molecular Biology; 1970, 48(3): 443-53), by computerized implementations of this algorithm (e.g., using the DNASTAR® Lasergene software), or by visual inspection. Alternatively, should the alignment be performed using sequences of distinct length, the optimal alignment of sequences can be preferably conducted by a local homology alignment algorithm, such as by the algorithm described by Smith and Waterson (Journal of Molecular Biology; 1981, 147: 195-197), by computerized implementations of this algorithm (e.g., using the DNASTAR® Lasergene software), or by visual inspection. Examples of global and local homology alignment algorithms are well-known to the skilled practitioner, and include, without limitation, ClustalV (global alignment), ClustalW (local alignment) and BLAST (local alignment).

"Isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

In the context of the present invention, the following abbreviations for the commonly occurring nucleic acid bases are used. "A" refers to adenosine, "C" refers to cytosine, "G" refers to guanosine, "T" refers to thymidine, and "U" refers to uridine.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may in some version contain (an) intron(s).

As used herein, the term "nucleic acid" or "polynucleotide" refers to a polymeric form of nucleotides of any length, either ribonucleotides or deoxyribonucleotides. Nucleic acids, nucleic acid sequences and polynucleotides as used herein are interchangeable. Thus, this term includes, but is not limited to, single-, double- or multi-stranded DNA or RNA, genomic DNA, cDNA, DNA-RNA hybrids, or a polymer comprising purine and pyrimidine bases, or other natural, chemically or biochemically modified, non-natural, or derived nucleotide bases. The backbone of the polynucleotide can comprise sugars and phosphate groups (as may typically be found in RNA or DNA), or modified or substituted sugar or phosphate groups. Alternatively, the backbone of the polynucleotide can comprise a polymer of synthetic subunits such as phosphoramidates and thus can be an oligodeoxynucleoside phosphoramidate (P—NH2) or a mixed phosphoramidatephosphodiester oligomer. The nucleic acid of the invention can be prepared by any method known to one skilled in the art, including chemical synthesis, recombination, and mutagenesis. In preferred embodiments, the nucleic acid of the invention is a DNA molecule, preferably a double stranded DNA molecule, and preferably synthesized by recombinant methods well known to those skilled in the art, such as the cloning of nucleic acid sequences from a recombinant library or a cell genome, using ordinary cloning technology and PCR™, and the like, and by synthetic means.

The term "promoter" as used herein is defined as a DNA sequence recognized by the synthetic machinery of the cell, or introduced synthetic machinery, required to initiate the specific transcription of a polynucleotide sequence.

As used herein, the term "promoter/regulatory sequence" means a nucleic acid sequence which is required for expression of a gene product operably linked to the promoter/regulatory sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue specific manner.

A "constitutive" promoter is a nucleotide sequence which, when operably linked with a polynucleotide which encodes or specifies a gene product, causes the gene product to be produced in a cell under most or all physiological conditions of the cell.

An "inducible" promoter is a nucleotide sequence which, when operably linked with a polynucleotide which encodes or specifies a gene product, causes the gene product to be produced in a cell substantially only when an inducer which corresponds to the promoter is present in the cell.

A "tissue-specific" promoter is a nucleotide sequence which, when operably linked with a polynucleotide encodes or specified by a gene, causes the gene product to be produced in a cell substantially only if the cell is a cell of the tissue type corresponding to the promoter.

The human BIN1 expression can rescue the myopathy displayed by Mtm1KO mice, which makes it an effective agent for the treatment of XLCNM. This method can lead to sustained improvements in muscle strength, size, and function.

The human BIN1 gene is located from base pair 127048023 to base pair 127107400 on chromosome 2 NC_000002.12 location. The BIN1 gene or gene products are also known by other names, including but not limited to AMPH2, AMPHL, SH3P9. The cDNA BIN1 full length corresponds to the longest isoform found in human; it encompasses 19 exons. Said BIN1 sequence is represented by SEQ ID NO: 1, which does not contain the muscle specific exon 11 and is thus not naturally expressed in muscle. However, in the context of the present invention, the presence of exon 11 is not mandatory. While BIN1 has 20 exons in total on the DNA, these exons are never found all together at the RNA level in humans—though all 20 exons can be used according to the present invention. Parts of the sequence represented by SEQ ID NO: 1 or any combination of at least two or three different exons 1-20 of BIN1 (SEQ ID NO: 3-22, respectively), more preferably any combination of at least two or three different exons 1-20 of BIN1 (SEQ ID NO: 3-22, respectively) according to increasing numbering of exons 1-20, can be used according to the invention. The skilled person would readily understand that "according to the increasing number of exons" means that the exons are combined according to their sequential order, or in other words consecutive order. Preferably, the number of exons present in the BIN1 nucleic acid sequence of the invention is 3, 4, 5, 6, 7, 8, 9, 10, 11, 12, 13, 14, 15, 16, 17, 18, 19, or 20 exons selected from the 20 BIN1 exons represented by SEQ ID NO: 3-22, and more preferably according to an increasing numbering of said exons 1-20 within the sequence. For example, the following sequences can be used according to the invention: an artificial cDNA sequence comprising at least exons 1 to 6 and 8 to 11 (SEQ ID NO: 23), cDNA comprising at least exons 1 to 6, 8 to 10, 12, and 17 to 20 (SEQ ID NO: 25; also named long isoform 9), cDNA comprising at least exons 1 to 6, 8 to 10, 12, and 18 to 20 (SEQ ID NO: 31; also named short isoform 9), cDNA comprising at least exons 1 to 6, 8 to 12, and 18 to 20 (SEQ ID NO: 27; also named isoform 8—without exon 17, which is BIN1 short muscle isoform containing the muscle specific exon 11), or cDNA comprising at least exons 1 to 6, 8 to 12, and 17 to 20 (SEQ ID NO: 29; also named isoform 8—with exon 17, which is BIN1 long muscle isoform containing the muscle specific exon 11, and corresponds to the NCBI isoform 8). The BIN1 nucleic acid sequence used according to the invention is able to encode the amphiphysin 2 polypeptide of the present invention. Particularly preferred BIN1 nucleic acids according to the invention are cDNA comprising at least exons 1 to 6, 8 to 10, 12, and 17 to 20 (SEQ ID NO: 25; also named long isoform 9), and cDNA comprising at least exons 1 to 6, 8 to 12, and 18 to 20 (SEQ ID NO: 27; also named isoform 8—without exon 17, which is BIN1 short muscle isoform containing the muscle specific exon 11).

As mentioned above, there are various tissue-specific isoforms or transcript variants of BIN1, among them, an isoform found in skeletal muscle specific is the isoform 8 which contains a phosphoinositides (PI) binding domain. Said cDNA isoform 8 is represented by SEQ ID NO: 27 or SEQ ID NO: 29, the corresponding proteins are represented by SEQ ID NO: 28 or SEQ ID NO: 30.

The natural human Amphiphysin 2 protein of the present invention is of 593 amino acids length. It is encoded by BIN1 gene (Gene ID 274). The Amphiphysin 2 protein is also known by other names, including but not limited to BIN1, AMPH2, AMPHL, SH3P9. Said protein is represented by SEQ ID NO: 2. As mentioned above, there are various tissue-specific isoforms of BIN1 gene. Parts of the sequence represented by SEQ ID NO: 2 or any polypeptide sequence deriving from or encoded by any combination of at least two or three different BIN1 exons 1-20, more preferably deriving from or encoded by any combination of at least two or three different BIN1 exons 1-20 (SEQ ID NO: 3-22, respectively) according to increasing numbering of BIN1 exons 1-20, can be used according to the invention. According to specific embodiments, the amphiphysin 2 polypeptide useful for the treatment of XLCNM comprises an amino acid sequence represented by SEQ ID NO: 2, 24, 26, 28, 30 or 32. Particularly preferred amphiphysin 2 polypeptides according to the invention comprise an amino acid sequence represented by SEQ ID NO:26 or 28.

In one aspect, the Amphiphysin 2 protein disclosed herein comprises an amino acid sequence at least 90% identical (or homologous) to SEQ ID NO: 2, 24, 26, 28, 30 or 32, or a bioactive fragment or variant thereof. In some embodiments, the Amphiphysin 2 comprises an amino acid sequence at least 80%, 85%, 90%, 95%, 97%, 98%, 99% or 100% identical to SEQ ID NO: 2, 24, 26, 28, 30 or 32, and is or less than 593 amino acids length, or a bioactive fragment or variant thereof.

As used herein, the Amphiphysin 2 disclosed herein can include various isoforms, fragments, variants, fusion proteins, and modified forms of the naturally occurring protein of the human Amphiphysin 2 which is of 593 amino acids length, as described above, and represented by SEQ ID NO:.2. Such isoforms, fragments or variants, fusion proteins, and modified forms of the naturally occurring Amphiphysin 2 polypeptide have at least a portion of the amino acid sequence of substantial sequence identity to the naturally occurring polypeptide, and retain at least one function of the naturally occurring Amphiphysin 2 polypeptide.

In certain embodiments, a bioactive fragment, variant, or fusion protein of the naturally occurring Amphiphysin 2 polypeptide comprises an amino acid sequence that is at least 80%, 85%, and preferably at least 90%, 95%, 97%, 98%, 99% or 100% identical to the naturally occurring Amphiphysin 2 of SEQ ID NO: 2, 26, 28, 30 or 32. As used herein, "fragments" or "variants" are understood to include bioactive fragments or bioactive variants that exhibit "bioactivity" as described herein. That is, bioactive fragments or variants of Amphiphysin 2 exhibit bioactivity that can be measured and tested. For example, bioactive fragments or variants exhibit the same or substantially the same bioactivity as native (i.e., wild-type, or normal) Amphiphysin 2 protein, and such bioactivity can be assessed by the ability of the fragment or variant to, e.g., curve or remodel membrane in vitro, upon transfection in cells, or in vivo, or bind known effector proteins, as dynamin 2, or lipids, as phosphoinositides. Methods in which to assess any of these criteria are described herein and/or one must refer more specifically to the following references: Amphiphysin 2 (Bin1) and T-tubule biogenesis in muscle.; Lee E, Marcucci M, Daniell L, Pypaert M, Weisz O A, Ochoa G C, Farsad K, Wenk M R, De Camilli P. Science. 2002 Aug. 16; 297(5584): 1193-6. PMID:12183633; Regulation of Bin1 SH3 domain binding by phosphoinositides.; Kojima C, Hashimoto A, Yabuta I, Hirose M, Hashimoto S, Kanaho Y, Sumimoto H, Ikegami T, Sabe H. EMBO J. 2004 Nov. 10; 23(22):4413-22. Epub 2004 Oct 14. PMID: 15483625; Mutations in amphiphysin 2 (BIN1) disrupt interaction with dynamin 2 and cause autosomal recessive centronuclear myopathy. Nicot A S, Toussaint A, Tosch V, Kretz C, Wallgren-Pettersson C, Iwarsson E, Kingston H, Garnier J M, Biancalana V, Oldfors A, Mandel J L, Laporte J. Nat Genet. 2007 September; 39(9):1134-9. Epub 2007 Aug. 5.

In the context of the present invention, the function (or bioactivity) of Amphiphysin 2 polypeptide, or bioactive fragments or variants thereof, can also be tested as described in the Examples described below, notably by assessing e.g. improvement of survival, lifespan, muscle strength, coordination, organization of muscle fibers/muscle ultrastructure, and/or focal adhesion.

As used herein, "substantially the same" refers to any parameter (e.g., activity or bioactivity as described above) that is at least 70% of a control against which the parameter is measured. In certain embodiments, "substantially the same" also refers to any parameter (e.g., activity) that is at least 75%, 80%, 85%, 90%, 92%, 95%, 97%, 98%, 99%, 100%, 102%, 105%, or 110% of a control against which the parameter is measured.

In certain embodiments, any of the Amphiphysin 2 polypeptides disclosed herein are possibly for use in a chimeric polypeptide further comprising one or more polypeptide portions that enhance one or more of in vivo stability, in vivo half-life, uptake/administration, and/or purification.

As used herein, BIN1 nucleic acid sequence can include BIN1 nucleic acid sequence that encodes a protein or fragment of the invention (such as those mentioned above) and/or contains SEQ ID NO:1, 23, 25, 27, 29 or 31, or a fragment thereof. In one embodiment, the BIN1 nucleic acid sequence which can be used according to the invention hybridizes to the sequence of SEQ ID NO:1, 23, 25, 27, 29 or 31 under stringent conditions. In another embodiment, the invention provides a nucleic acid sequence complementary to the nucleic acid sequence of SEQ ID NO:1, 23, 25, 27, 29 or 31. In still another embodiment, the invention provides a nucleic acid sequence encoding a fusion protein of the invention. In a further embodiment, the invention provides an allelic variant of any of the BIN1 nucleic acid sequences of the invention.

The present invention provides a composition that increases BIN1 expression in a muscle. For example, in one embodiment, the composition comprises an isolated BIN1 nucleic acid sequence or a nucleic acid comprising at least one BIN1 nucleic acid sequence. As described herein, delivery of a composition comprising such nucleic acid sequence improves muscle function. Furthermore, the delivery of a composition comprising such nucleic acid sequence prolongs survival of a subject with XLCNM.

The present invention also concerns a pharmaceutical composition comprising a Amphiphysin 2 polypeptide as defined above, or expression vector comprising at least one BIN1 nucleic acid sequence as defined above, in combination with a pharmaceutical carrier. Also disclosed said compositions are for use in the treatment of XLCNM.

The present invention further concerns a method for the treatment of XLCNM, wherein the method comprises a step of administering into a subject in need of such treatment a therapeutically efficient amount of Amphiphysin 2 polypeptide, or expression vector comprising at least one BIN1 nucleic acid sequence, as defined above.

Finally, the present invention concerns the use of Amphiphysin 2 polypeptide, or expression vector comprising at least one BIN1 nucleic acid sequence, as defined above, for the preparation of a pharmaceutical composition for the treatment of XLCNM.

The isolated nucleic acid sequence or a biologically functional fragment or variant thereof as defined above can be obtained using any of the many recombinant methods known in the art, such as, for example by screening cDNA or DNA libraries from cells expressing the BIN1 gene, by deriving the gene from a vector known to include the same, or by isolating directly from cells and tissues containing the same, using standard techniques (such as PCR). Alternatively, the gene of interest can be produced synthetically, rather than cloned.

The present invention also includes a vector in which the isolated BIN1 nucleic acid sequence or the nucleic acid comprising at least one BIN1 nucleic acid sequence of the present invention is inserted; and which is generally operably linked to one or more control sequences that direct expression of BIN1. The art is replete with suitable vectors that are useful in the present invention. It also refers to a nucleic acid construct or a recombinant host cell transformed with the vector of the invention.

In summary, the expression of BIN1 nucleic acid sequence is typically achieved by operably linking a BIN1 nucleic acid sequence or portions thereof to a promoter, and incorporating the construct into an expression vector. The vectors to be used are suitable for replication and, optionally, integration in eukaryotic cells. Typical vectors contain transcription and translation terminators, initiation sequences, and promoters useful for regulation of the expression of the desired nucleic acid sequence.

The vectors of the present invention may also be used for gene therapy, using standard gene delivery protocols. Methods for gene delivery are known in the art. See, e.g., U.S. Pat. Nos. 5,399,346; 5,580,859; or 5,589,466. In another embodiment, the invention provides a gene therapy vector.

The BIN1 nucleic acid sequence of the invention can be cloned into a number of types of vectors. For example, the nucleic acid can be cloned into a vector including, but not limited to a plasmid, a phagemid, a phage derivative, an animal virus, and a cosmid. Vectors of particular interest include expression vectors, replication vectors, probe generation vectors, and sequencing vectors.

Further, the vector may be provided to a cell in the form of a viral vector. Viral vector technology is well known in the art and is described, for example, in Sambrook et al. (2001, Molecular Cloning: A Laboratory Manual, Cold Spring Harbor Laboratory, New York), and in other virology and molecular biology manuals. Viruses, which are useful as vectors include, but are not limited to, retroviruses, adenoviruses, adeno-associated viruses, herpes viruses, and lentiviruses. In general, a suitable vector contains an origin of replication functional in at least one organism, a promoter sequence, convenient restriction endonuclease sites, and one or more selectable markers, (e.g., WO 01/96584; WO 01/29058; and U.S. Pat. No. 6,326,193).

A number of viral based systems have been developed for gene transfer into mammalian cells. For example, retroviruses provide a convenient platform for gene delivery systems. A selected gene can be inserted into a vector and packaged in retroviral particles using techniques known in the art. The recombinant virus can then be isolated and delivered to cells of the subject either in vivo or ex vivo. A number of retroviral systems are known in the art. In some embodiments, adenovirus vectors are used. A number of adenovirus vectors are known in the art. In one embodiment, lentivirus vectors are used.

For example, vectors derived from retroviruses such as the lentivirus are suitable tools to achieve long-term gene transfer since they allow long-term, stable integration of a transgene and its propagation in daughter cells. In a preferred embodiment, the composition includes a vector derived from an adeno-associated virus (AAV). Adeno-associated viral (AAV) vectors have become powerful gene delivery tools for the treatment of various disorders. AAV vectors possess a number of features that render them ideally suited for gene therapy, including a lack of pathogenicity, minimal immunogenicity, and the ability to transduce post-mitotic cells in a stable and efficient manner. Expression of a particular gene contained within an AAV vector can be specifically targeted to one or more types of cells by choosing the appropriate combination of AAV serotype, promoter, and delivery method.

In one embodiment, the BIN1 nucleic acid sequence is contained within an AAV vector. More than 30 naturally occurring serotypes of AAV are available. Many natural variants in the AAV capsid exist, allowing identification and use of an AAV with properties specifically suited for skeletal muscle. AAV viruses may be engineered using conventional molecular biology techniques, making it possible to optimize these particles for cell specific delivery of myotubularin nucleic acid sequences, for minimizing immunogenicity, for tuning stability and particle lifetime, for efficient degradation, for accurate delivery to the nucleus, etc.

Among the serotypes of AAVs isolated from human or non-human primates (NHP) and well characterized, human serotype 2 is the first AAV that was developed as a gene transfer vector; it has been widely used for efficient gene transfer experiments in different target tissues and animal models. Clinical trials of the experimental application of AAV2 based vectors to some human disease models are in progress. Other useful AAV serotypes include AAV1, AAV3, AAV4, AAV5, AAV6, AAV7, AAV8, AAV9 and AAV10.

In one embodiment, the vectors useful in the compositions and methods described herein contain, at a minimum, sequences encoding a selected AAV serotype capsid, e.g., an AAV8 capsid, or a fragment thereof. In another embodiment, useful vectors contain, at a minimum, sequences encoding a selected AAV serotype rep protein, e.g., AAV8 rep protein, or a fragment thereof. Optionally, such vectors may contain both AAV cap and rep proteins.

The AAV vectors of the invention may further contain a minigene comprising a BIN1 nucleic acid sequence as described above which is flanked by AAV 5' (inverted terminal repeat) ITR and AAV 3' ITR. A suitable recombinant adeno-associated virus (AAV) is generated by culturing a host cell which contains a nucleic acid sequence encoding an adeno-associated virus (AAV) serotype capsid protein, or fragment thereof, as defined herein; a functional rep gene; a minigene composed of, at a minimum, AAV inverted terminal repeats (ITRs) and a BIN1 nucleic acid sequence, or biologically functional fragment thereof and sufficient helper functions to permit packaging of the minigene into the AAV capsid protein. The components required to be cultured in the host cell to package an AAV minigene in an AAV capsid may be provided to the host cell in trans. Alternatively, any one or more of the required components (e.g., minigene, rep sequences, cap sequences, and/or helper functions) may be provided by a stable host cell which has been engineered to contain one or more of the required components using methods known to those of skill in the art.

In specific embodiments, such a stable host cell will contain the required component(s) under the control of a constitutive promoter. In other embodiments, the required component(s) may be under the control of an inducible promoter. Examples of suitable inducible and constitutive promoters are provided elsewhere herein, and are well known in the art. In still another alternative, a selected stable host cell may contain selected component(s) under the control of a constitutive promoter and other selected component(s) under the control of one or more inducible promoters. For example, a stable host cell may be generated which is derived from 293 cells (which contain E1 helper functions under the control of a constitutive promoter), but which contains the rep and/or cap proteins under the control of inducible promoters. Still other stable host cells may be generated by one of skill in the art.

The minigene, rep sequences, cap sequences, and helper functions required for producing the rAAV of the invention may be delivered to the packaging host cell in the form of any genetic element which transfers the sequences carried thereon. The selected genetic element may be delivered using any suitable method, including those described herein and any others available in the art. The methods used to construct any embodiment of this invention are known to those with skill in nucleic acid manipulation and include genetic engineering, recombinant engineering, and synthetic techniques. Similarly, methods of generating rAAV virions are well known and the selection of a suitable method is not a limitation on the present invention.

Unless otherwise specified, the AAV ITRs, and other selected AAV components described herein, may be readily selected from among any AAV serotype, including, without limitation, AAV1, AAV2, AAV3, AAV4, AAV5, AAV6, AAV7, AAV8, AAV9 and AAV10 or other known or as yet unknown AAV serotypes. These ITRs or other AAV components may be readily isolated from an AAV serotype using techniques available to those of skill in the art. Such an AAV may be isolated or obtained from academic, commercial, or public sources (e.g., the American Type Culture Collection, Manassas, Va.). Alternatively, the AAV sequences may be obtained through synthetic or other suitable means by reference to published sequences such as are available in the literature or in databases such as, e.g., GenBank, PubMed, or the like.

The minigene is composed of, at a minimum, a BIN1 nucleic acid sequence (the transgene) and its regulatory sequences, and 5' and 3' AAV inverted terminal repeats (ITRs). In one embodiment, the ITRs of AAV serotype 2 are used. However, ITRs from other suitable serotypes may be selected. It is this minigene which is packaged into a capsid protein and delivered to a selected host cell. The BIN1 encoding nucleic acid coding sequence is operatively linked to regulatory components in a manner which permits transgene transcription, translation, and/or expression in a host cell.

In addition to the major elements identified above for the minigene, the AAV vector generally includes conventional control elements which are operably linked to the transgene in a manner which permits its transcription, translation and/or expression in a cell transfected with the plasmid vector or infected with the virus produced by the invention. As used herein, "operably linked" sequences include both expression control sequences that are contiguous with the gene of interest and expression control sequences that act in trans or at a distance to control the gene of interest. Expression control sequences include appropriate transcription initiation, termination, promoter and enhancer sequences; efficient RNA processing signals such as splicing and polyadenylation (polyA) signals; sequences that stabilize cytoplasmic mRNA; sequences that enhance translation efficiency (i.e., Kozak consensus sequence); sequences that enhance protein stability; and when desired, sequences that enhance secretion of the encoded product. A great number of expression control sequences, including promoters which are native, constitutive, inducible and/or tissue-specific, are known in the art and may be utilized. Additional promoter elements, e.g., enhancers, regulate the frequency of transcriptional initiation. Typically, these are located in the region 30-110 bp upstream of the start site, although a number of promoters have recently been shown to contain functional elements downstream of the start site as well. The spacing between promoter elements frequently is flexible, so that promoter function is preserved when elements are inverted or moved relative to one another. Depending on the promoter, it appears that individual elements can function either cooperatively or independently to activate transcription.

In order to assess the expression of BIN1, the expression vector to be introduced into a cell can also contain either a selectable marker gene or a reporter gene or both to facilitate identification and selection of expressing cells from the population of cells sought to be transfected or infected through viral vectors. In other aspects, the selectable marker may be carried on a separate piece of DNA and used in a co-transfection procedure. Both selectable markers and reporter genes may be flanked with appropriate regulatory sequences to enable expression in the host cells. Useful selectable markers include, for example, antibiotic-resistance genes, such as neo and the like.

Reporter genes are used for identifying potentially transfected cells and for evaluating the functionality of regulatory sequences. In general, a reporter gene is a gene that is not present in or expressed by the recipient organism or tissue and that encodes a polypeptide whose expression is manifested by some easily detectable property, e.g., enzymatic activity. Expression of the reporter gene is assayed at a suitable time after the DNA has been introduced into the recipient cells. Suitable reporter genes may include genes encoding luciferase, beta-galactosidase, chloramphenicol acetyl transferase, secreted alkaline phosphatase, or the green fluorescent protein gene. Suitable expression systems are well known and may be prepared using known techniques or obtained commercially. In general, the construct with the minimal 5' flanking region showing the highest level of expression of reporter gene is identified as the promoter. Such promoter regions may be linked to a reporter gene and used to evaluate agents for the ability to modulate promoter-driven transcription.

In one embodiment, the composition comprises a naked isolated BIN1 nucleic acid as defined above, wherein the isolated nucleic acid is essentially free from transfection-facilitating proteins, viral particles, liposomal formulations and the like. It is well known in the art that the use of naked isolated nucleic acid structures, including for example naked DNA, works well with inducing expression in muscle. As such, the present invention encompasses the use of such compositions for local delivery to the muscle and for systemic administration (Wu et al., 2005, Gene Ther, 12(6): 477-486).

Methods of introducing and expressing genes into a cell are known in the art. In the context of an expression vector, the vector can be readily introduced into a host cell, e.g., mammalian, bacterial, yeast, or insect cell by any method in the art. For example, the expression vector can be transferred into a host cell by physical, chemical, or biological means.

For use in vivo, the nucleotides of the invention may be stabilized, via chemical modifications, such as phosphate backbone modifications (e.g., phosphorothioate bonds). The nucleotides of the invention may be administered in free (naked) form or by the use of delivery systems that enhance stability and/or targeting, e.g., liposomes, or incorporated into other vehicles, such as hydrogels, cyclodextrins, biodegradable nanocapsules, bioadhesive microspheres, or proteinaceous vectors, or in combination with a cationic peptide. They can also be coupled to a biomimetic cell penetrating peptide. They may also be administered in the form of their precursors or encoding DNAs.

Chemically stabilized versions of the nucleotides also include "Morpholinos" (phosphorodiamidate morpholino oligomers—PMO), 2'-O-Methyl oligomers, AcHN-(RXRRBR)2XB (SEQ ID NO: 35) peptide-tagged PMO (R, arginine, X, 6-aminohexanoic acid and B, β-alanine) (PPMO), tricyclo-DNAs, or small nuclear (sn) RNAs. All these techniques are well known in the art. These versions of nucleotides could also be used for exon skipping to promote expression of endogenous BIN1.

In the case where a non-viral delivery system is utilized, an exemplary delivery vehicle is a liposome. The use of lipid formulations is contemplated for the introduction of the nucleic acids into a host cell (in vitro, ex vivo or in vivo). In another aspect, the nucleic acid may be associated with a lipid. The nucleic acid associated with a lipid may be encapsulated in the aqueous interior of a liposome, interspersed within the lipid bilayer of a liposome, attached to a liposome via a linking molecule that is associated with both the liposome and the oligonucleotide, entrapped in a liposome, complexed with a liposome, dispersed in a solution containing a lipid, mixed with a lipid, combined with a lipid, contained as a suspension in a lipid, contained or complexed with a micelle, or otherwise associated with a lipid. Lipid, lipid/DNA or lipid/expression vector associated compositions are not limited to any particular structure in solution.

Regardless of the method used to introduce exogenous nucleic acids into a host cell or otherwise expose a cell to the BIN1 nucleic acid sequence of the present invention, in order to confirm the presence of the recombinant DNA sequence in the host cell, a variety of assays may be performed. Such assays include, for example, "molecular biological" assays well known to those of skill in the art, such as Southern and Northern blotting, RT-PCR and PCR; "biochemical" assays, such as detecting the presence or absence of a particular peptide, e.g., by immunological means (ELISAs and Western blots) or by assays described herein to identify agents falling within the scope of the invention.

Genome editing can also be used as a tool according to the invention. Genome editing is a type of genetic engineering in which DNA is inserted, replaced, or removed from a genome using artificially engineered nucleases, or "molecular scissors". The nucleases create specific double-stranded break (DSBs) at desired locations in the genome, and harness the cell's endogenous mechanisms to repair the induced break by natural processes of homologous recombination (HR) and non-homologous end-joining (NHEJ). There are currently four families of engineered nucleases being used: Zinc finger nucleases (ZFNs), Transcription Activator-Like Effector Nucleases (TALENs), the CRISPR/Cas system (more specifically Cas9 system, as described by P. Mali et al., in Nature Methods, vol. 10 No. 10, October 2013), or engineered meganuclease re-engineered homing endonucleases. Said nucleases can be delivered to the cells either as DNAs or mRNAs, such DNAs or mRNAs are engineered to overexpress BIN1 according to the invention. The CRISPR/Cas system can be used, in fusion with activator or regulator proteins to enhance expression of BIN1 through transcriptional activation or epigenetic modification (Vora S, Tuttle M, Cheng J, Church G, FEBS J. 2016 September; 283(17):3181-93. doi: 10.1111/febs.13768. Epub 2016 Jul 2. Next stop for the CRISPR revolution: RNA-guided epigenetic regulators).

The nucleotides as defined above used according to the invention can be administered in the form of DNA precursors.

The Amphiphysin 2 polypeptide as defined above, including fragments or variants thereof, can be chemically synthesized using techniques known in the art such as conventional solid phase chemistry. The fragments or variants can be produced (by chemical synthesis, for instance) and tested to identify those fragments or variants that can function as well as or substantially similarly to the native protein, for example, by testing their ability to curve or remodel membrane in vitro, upon transfection in cells, or in vivo, or bind known effector proteins, as dynamin 2, or lipids, as phosphoinositides, or treat XLCNM.

In certain embodiments, the present invention contemplates modifying the structure of an amphiphysin 2 polypeptide for such purposes as enhancing therapeutic or prophylactic efficacy, or stability (e.g., ex vivo shelf life and resistance to proteolytic degradation in vivo). Such modified amphiphysin 2 polypeptides have the same or substantially the same bioactivity as naturally-occurring (i.e., native or wild-type) amphiphysin 2 polypeptide. Modified polypeptides can be produced, for instance, by amino acid substitution, deletion, or addition at one or more positions. For instance, it is reasonable to expect, for example, that an isolated replacement of a leucine with an isoleucine or valine, an aspartate with a glutamate, or a similar replacement of an amino acid with a structurally related amino acid (e.g., conservative mutations) will not have a major effect on the biological activity of the resulting molecule. Conservative replacements are those that take place within a family of amino acids that are related in their side chains.

In a particular embodiment, the therapeutically effective amount to be administered according to the invention is an amount sufficient to alleviate at least one or all of the signs of XLCNM, or to improve muscle function of subject with XLCNM. The amount of amphiphysin 2 or of expression vector comprising at least one BIN1 nucleic acid sequence to be administered can be determined by standard procedure well known by those of ordinary skill in the art. Physiological data of the patient (e.g. age, size, and weight), the routes of administration and the disease to be treated have to be taken into account to determine the appropriate dosage, optionally compared with subjects that do not present centronuclear myopathies. One skilled in the art will recognize that the amount of amphiphysin 2 polypeptide or of a vector containing comprising at least one BIN1 nucleic acid sequence to be administered will be an amount that is sufficient to treat at least one or all of the signs of XLCNM, or to improve muscle function of subject with XLCNM. Such an amount may vary inter alia depending on such factors as the selected amphiphysin 2 polypeptides or vector expressing the same or expression vectors comprising at least one BIN1 nucleic acid sequence polypeptide, the gender, age, weight, overall physical condition of the patient, etc. and may be determined on a case by case basis. The amount may also vary according to other components of a treatment protocol (e.g. administration of other pharmaceuticals, etc.). Generally, when the therapeutic agent is a nucleic acid, a suitable dose is in the range of from about 1 mg/kg to about 100 mg/kg, and more usually from about 2 mg/kg/day to about 10 mg/kg. If a viral-based delivery of the nucleic acid is chosen, suitable doses will depend on different factors such as the virus that is employed, the route of delivery (intramuscular, intravenous, intra-arterial or other), but may typically range from $10^{-9}$ to $10^{-15}$ viral particles/kg. Those of skill in the art will recognize that such parameters are normally worked out during clinical trials. Further, those of skill in the art will recognize that, while disease symptoms may be completely alleviated by the treatments described herein, this need not be the case. Even a partial or intermittent relief of symptoms may be of great benefit to the recipient. In addition, treatment of the patient may be a single event, or the patient is administered with the amphiphysin 2 or nucleic acid encoding the same or expression vector comprising at least one BIN1 nucleic acid sequence on multiple occasions, that may be, depending on the results obtained, several days apart, several weeks apart, or several months apart, or even several years apart.

The pharmaceutical composition of the invention is formulated in accordance with standard pharmaceutical practice (see, e.g., Remington: The Science and Practice of Pharmacy (20th ed.), ed. A. R. Gennaro, Lippincott Williams & Wilkins, 2000 and Encyclopedia of Pharmaceutical Technology, eds. J. Swarbrick and J. C. Boylan, 1988-1999, Marcel Dekker, New York) known by a person skilled in the art.

Possible pharmaceutical compositions include those suitable for oral, rectal, intravaginal, mucosal, topical (including transdermal, buccal and sublingual), or parenteral (including subcutaneous (sc), intramuscular (im), intravenous (iv), intra-arterial, intradermal, intrasternal, injection, or infusion techniques) administration. For these formulations, conventional excipient can be used according to techniques well known by those skilled in the art.

In particular, intramuscular or systemic administration is preferred. More particularly, in order to provide a localized therapeutic effect, specific muscular or intramuscular administration routes are preferred.

Pharmaceutical compositions according to the invention may be formulated to release the active drug substantially immediately upon administration or at any predetermined time or time period after administration.

```
SEQUENCE LISTING
cDNA HUMAN BIN1 isoform 1 (longest isoform)
                                                   SEQ ID NO: 1
ATGGCAGAGATGGGCAGTAAAGGGGTGACGGCGGGAAAGATCGCCAGCAACGT

GCAGAAGAAGCTCACCCGCGCGCAGGAGAAGGTTCTCCAGAAGCTGGGGAAGGC

AGATGAGACCAAGGATGAGCAGTTTGAGCAGTGCGTCCAGAATTTCAACAAGCA

GCTGACGGAGGGCACCCGGCTGCAGAAGGATCTCCGGACCTACCTGGCCTCCGTC

AAAGCCATGCACGAGGCTTCCAAGAAGCTGAATGAGTGTCTGCAGGAGGTGTAT

GAGCCCGATTGGCCCGGCAGGGATGAGGCAAACAAGATCGCAGAGAACAACGAC

CTGCTGTGGATGGATTACCACCAGAAGCTGGTGGACCAGGCGCTGCTGACCATGG

ACACGTACCTGGGCCAGTTCCCCGACATCAAGTCACGCATTGCCAAGCGGGGGCG

CAAGCTGGTGGACTACGACAGTGCCCGGCACCACTACGAGTCCCTTCAAACTGC

CAAAAAGAAGGATGAAGCCAAAATTGCCAAGCCTGTCTCGCTGCTTGAGAAAGC

CGCCCCCAGTGGTGCCAAGGCAAACTGCAGGCTCATCTCGTAGCTCAAACTAAC

CTGCTCCGAAATCAGGCCGAGGAGGAGCTCATCAAAGCCCAGAAGGTGTTTGAG

GAGATGAATGTGGATCTGCAGGAGGAGCTGCCGTCCCTGTGGAACAGCCGCGTA

GGTTTCTACGTCAACACGTTCCAGAGCATCGCGGGCCTGGAGGAAAACTTCCACA

AGGAGATGAGCAAGCTCAACCAGAACCTCAATGATGTGCTGGTCGGCCTGGAGA

AGCAACACGGGAGCAACACCTTCACGGTCAAGGCCCAGCCCAGTGACAACGCGC

CTGCAAAAGGGAACAAGAGCCCTTCGCCTCCAGATGGCTCCCCTGCCGCCACCCC

CGAGATCAGAGTCAACCACGAGCCAGAGCCGGCCGGCGGGGCCACGCCCGGGGC

CACCCTCCCCAAGTCCCCATCTCAGCTCCGGAAAGGCCCACCAGTCCCTCCGCCT

CCCAAACACACCCCGTCCAAGGAAGTCAAGCAGGAGCAGATCCTCAGCCTGTTTG

AGGACACGTTTGTCCCTGAGATCAGCGTGACCACCCCCTCCCAGTTTGAGGCCCC

GGGGCCTTTCTCGGAGCAGGCCAGTCTGCTGGACCTGGACTTTGACCCCCTCCCG

CCCGTGACGAGCCCTGTGAAGGCACCCACGCCCTCTGGTCAGTCAATTCCATGGG

ACCTCTGGGAGCCCACAGAGAGTCCAGCCGGCAGCCTGCCTTCCGGGGAGCCCA

GCGCTGCCGAGGGCACCTTTGCTGTGTCCTGGCCCAGCCAGACGGCCGAGCCGGG

GCCTGCCCAACCAGCAGAGGCCTCGGAGGTGGCGGGTGGGACCCAACCTGCGGC

TGGAGCCCAGGAGCCAGGGGAGACGGCGGCAAGTGAAGCAGCCTCCAGCTCTCT

TCCTGCTGTCGTGGTGGAGACCTTCCCAGCAACTGTGAATGGCACCGTGGAGGGC

GGCAGTGGGGCCGGGCGCTTGGACCTGCCCCCAGGTTTCATGTTCAAGGTACAGG

CCCAGCACGACTACACGGCCACTGACACAGACGAGCTGCAGCTCAAGGCTGGTG

ATGTGGTGCTGGTGATCCCCTTCCAGAACCCTGAAGAGCAGGATGAAGGCTGGCT

CATGGGCGTGAAGGAGAGCGACTGGAACCAGCACAAGGAGCTGGAGAAGTGCC

GTGGCGT CTTCCCCGAGAACTTCACTGAGAGGGTCCCATGA
```

-continued

AMINO ACID SEQUENCE of HUMAN BIN1 isoform 1 (longest isoform)
                                                SEQ ID NO: 2
MAEMGSKGVTAGKIASNVQKKLTRAQEKVLQKLGKADETKDEQFEQCVQNFNKQL

TEGTRLQKDLRTYLASVKAMHEASKKLNECLQEVYEPDWPGRDEANKIAENNDLL

WMDYHQKLVDQALLTMDTYLGQFPDIKSRIAKRGRKLVDYDSARHHYESLQTAKK

KDEAKIAKPVSLLEKAAPQWCQGKLQAHLVAQTNLLRNQAEEELIKAQKVFEEMNV

DLQEELPSLWNSRVGFYVNTFQSIAGLEENFHKEMSKLNQNLNDVLVGLEKQHGSN

TFTVKAQPSDNAPAKGNKSPSPPDGSPAATPEIRVNHEPEPAGGATPGATLPKSPSQL

RKGPPVPPPPKHTPSKEVKQEQILSLFEDTFVPEISVTTPSQFEAPGPFSEQASLLDLDF

DPLPPVTSPVKAPTPSGQSIPWDLWEPTESPAGSLPSGEPSAAEGTFAVSWPSQTAEPG

PAQPAEASEVAGGTQPAAGAQEPGETAASEAASSSLPAVVVETFPATVNGTVEGGSG

AGRLDLPPGFMFKVQAQHDYTATDTDELQLKAGDVVLVIPFQNPEEQDEGWLMGV

KESDWNQHKELEKCRGVFPENFTERVP

EXON 1
                                                SEQ ID NO: 3
Atggcagagatgggcagtaaaggggtgacggcgggaaagatcgccagcaacgtgcagaagaag ctcacccgcgcgcaggagaag EXON 2
                                                SEQ ID NO: 4
Gttctccagaagctggggaaggcagatgagaccaaggatgagcagtttgagcagtgcgtccag aatttcaacaagcagct EXON3
                                                SEQ ID NO: 5
Gacggagggcacccggctgcagaaggatctccggacctacctggcctccgtcaaag EXON 4
                                                SEQ ID NO: 6
Ccatgcacgaggcttccaagaagctgaatgagtgtctgcaggaggtgtatgagcccgattggc ccggcagggatgaggcaaacaagatcgcagag EXON 5
                                                SEQ ID NO: 7
Aacaacgacctgctgtggatggattaccaccagaagctggtggaccaggcgctgctgaccatg gacacgtacctgggccagttccccgacatcaag EXON 6
                                                SEQ ID NO: 8
Tcacgcattgccaagcgggggcgcaagctggtggactacgacagtgcccggcaccactacgag tcccttcaaactgccaaaaagaaggatgaagccaaaattgccaag EXON 7 (not present in skeletal muscle isoform)
                                                SEQ ID NO: 9
Cctgtctcgctgcttgagaaagccgccccccagtggtgccaaggcaaactgcaggctcatctc gtagctcaaactaacctgctccgaaatcag EXON8
                                                SEQ ID NO: 10
Gccgaggaggagctcatcaaagcccagaaggtgtttgaggagatgaatgtggatctgcaggag gagctgccgtccctgtggaacag EXON 9
                                                SEQ ID NO: 11
Ccgcgtaggtttctacgtcaacacgttccagagcatcgcgggcctggaggaaaacttccacaa ggagatgagcaag EXON 10
SEQ ID NO: 12
Ctcaaccagaacctcaatgatgtgctggtcggcctggagaagcaacacgggagcaacaccttc acggtcaaggcccagcccag EXON 11 (muscle specific exon)
SEQ ID NO: 13
aaagaaaagtaaactgttttcgcggctgcgcagaaagaagaacag EXON 12 (not present in skeletal muscle isoform)
SEQ ID NO: 14
tgacaacgcgcctgcaaaagggaacaagagcccttcgcctccagatggctcccctgccgccac ccccgagatcagagtcaaccacgagccagagccggccggcggggccacgcccggggccaccct ccccaagtccccatctcag EXON 13 (not present in skeletal muscle isoform)
SEQ ID NO: 15
tttgaggccccggggcctttctcggagcaggccagtctgctggacctggactttgaccccctc ccgcccgtgacgagccctgtgaaggcacccacgccctctggtcag EXON 14 (not present in skeletal muscle isoform)
SEQ ID NO: 16
tcaattccatgggacctctgggag EXON 15 (not present in skeletal muscle isoform)
SEQ ID NO: 17
cccacagagagtccagccggcagcctgccttccggggagcccagcgctgccgagggcacctttt gctgtgtcctggcccagccagacggccgagccggggcctgcccaa EXON 16 (not present in skeletal muscle isoform)
SEQ ID NO: 18
ccagcagaggcctcggaggtggcgggtgggacccaacctgcggctggagcccaggagccaggg gagacggcggcaagtgaagcagcctcc EXON 17
SEQ ID NO: 19
Ccagcagaggcctcggaggtggcgggtgggacccaacctgcggctggagcccaggagccaggg gagacggcggcaagtgaagcagcctcc EXON 18
SEQ ID NO: 20
Agctctcttcctgctgtcgtggtggagaccttcccagcaactgtgaatggcaccgtggagggc ggcagtggggccgggcgcttggacctgcccccaggtttcatgttcaag EXON 19
SEQ ID NO: 21
Gtacaggcccagcacgactacacggccactgacacagacgagctgcagctcaaggctggtgat gtggtgctggtgatccccttccagaaccctgaagagcag EXON 20
SEQ ID NO: 22
gatgaaggctggctcatgggcgtgaaggagagcgactggaaccagcacaaggagctggagaag tgccgtggcgtcttccccgagaacttcactgagagggtcccatga artificial cDNA sequence with exons 1 to 6 and 8 to 11
SEQ ID NO: 23
atggcagagatgggcagtaaaggggtgacggcgggaaagatcgccagcaacgtgcagaagaag ctcacccgcgcgcaggagaaggttctccagaagctggggaaggcagatgagaccaaggatgag cagtttgagcagtgcgtccagaatttcaacaagcagctgacggagggcacccggctgcagaag gatctccggaccctacctggcctccgtcaaagccatgcacgaggcttccaagaagctgaatgag tgtctgcaggaggtgtatgagcccgattggcccggcagggatgaggcaaacaagatcgcagag aacaacgacctgctgtggatggattaccaccagaagctggtggaccaggcgctgctgaccatg gacacgtacctgggccagttccccgacatcaagtcacgcattgccaagcgggggcgcaagctg -continued

```
gtggactacgacagtgcccggcaccactacgagtcccttcaaactgccaaaaagaaggatgaa gccaaaattgccaaggccgaggaggagctcatcaaagcccagaaggtgtttgaggagatgaat gtggatctgcaggaggagctgccgtccctgtggaacagccgcgtaggtttctacgtcaacacg ttccagagcatcgcggggcctggaggaaaaacttccacaaggagatgagcaagctcaaccagaac ctcaatgatgtgctggtcggcctggagaagcaacacgggagcaacaccttcacggtcaaggcc cagcccagaaagaaaagtaaactgttttcgcggctgcgcagaaagaagaacagtga
```

AMINO ACID SEQUENCE corresponding to artificial cDNA sequence
with exons 1 to 6 and 8 to 11
SEQ ID NO: 24

```
MAEMGSKGVTAGKIASNVQKKLTRAQEKVLQKLGKADETKDEQFEQCVQNFNKQL

TEGTRLQKDLRTYLASVKAMHEASKKLNECLQEVYEPDWPGRDEANKIAENNDLL

WMDYHQKLVDQALLTMDTYLGQFPDIKSRIAKRGRKLVDYDSARHHYESLQTAKK

KDEAKIAKAEEELIKAQKVFEEMNVDLQEELPSLWNSRVGFYVNTFQSIAGLEEN

FHKEMSKLNQNLNDVLVGLEKQHGSNTFTVKAQPRKKSKLFSRLRRKKNS
``` cDNA sequence with exons 1 to 6, 8 to 10, 12, and 17 to 20 -
named long isoform 9
SEQ ID NO: 25

```
atggcagagatgggcagtaaaggggtgacggcgggaaagatcgccagcaacgtgcagaagaag ctcacccgcgcgcaggagaaggttctccagaagctggggaaggcagatgagaccaaggatgag cagtttgagcagtgcgtccagaatttcaacaagcagctgacggagggcaccggctgcagaag gatctccggacctacctggcctccgtcaaagccatgcacgaggcttccaagaagctgaatgag tgtctgcaggaggtgtatgagcccgattggcccggcagggatgaggcaaacaagatcgcagag aacaacgacctgctgtggatggattaccaccagaagctggtggaccaggcgctgctgaccatg gacacgtacctgggccagttccccgacatcaagtcacgcattgccaagcgggggcgcaagctg gtggactacgacagtgcccggcaccactacgagtcccttcaaactgccaaaaagaaggatgaa gccaaaattgccaaggccgaggaggagctcatcaaagcccagaaggtgtttgaggagatgaat gtggatctgcaggaggagctgccgtccctgtggaacagccgcgtaggtttctacgtcaacacg ttccagagcatcgcggggcctggaggaaaaacttccacaaggagatgagcaagctcaaccagaac ctcaatgatgtgctggtcggcctggagaagcaacacgggagcaacaccttcacggtcaaggcc cagcccagtgacaacgcgcctgcaaaagggaacaagagcccttcgcctccagatggctccct gccgccaccccgagatcagagtcaaccacgagccagagccggccggcggggccacgcccggg gccacccctccccaagtccccatctcagccagcagaggcctcggaggtggcgggtgggacccaa cctgcggctggagcccaggagccaggggagacggcggcaagtgaagcagcctccagctctctt cctgctgtcgtggtggagaccttcccagcaactgtgaatggcaccgtggagggcggcagtggg gccgggcgcttggacctgcccccaggtttcatgttcaaggtacaggcccagcacgactacacg gccactgacacagacgagctgcagctcaaggctggtgatgtggtgctggtgatcccctcccag aaccctgaagagcaggatgaaggctggctcatgggcgtgaaggagagcgactggaaccagcac aaggagctggagaagtgccgtggcgtcttccccgagaacttcactgagagggtcccatga
```

AMINO ACID SEQUENCE corresponding to cDNA sequence with exons
1 to 6, 8 to 10, 12, and 17 to 20 - named long isoform 9
SEQ ID NO: 26

```
MAEMGSKGVTAGKIASNVQKKLTRAQEKVLQKLGKADETKDEQFEQCVQNFNKQL

TEGTRLQKDLRTYLASVKAMHEASKKLNECLQEVYEPDWPGRDEANKIAENNDLL

WMDYHQKLVDQALLTMDTYLGQFPDIKSRIAKRGRKLVDYDSARHHYESLQTAKK

KDEAKIAKAEEELIKAQKVFEEMNVDLQEELPSLWNSRVGFYVNTFQSIAGLEEN
```

-continued

FHKEMSKLNQNLNDVLVGLEKQHGSNTFTVKAQPSDNAPAKGNKSPSPPDGSPAA

TPEIRVNHEPEPAGGATPGATLPKSPSQPAEASEVAGGTQPAAGAQEPGETAASE

AASSSLPAVVVETFPATVNGTVEGGSGAGRLDLPPGFMFKVQAQHDYTATDTDEL

QLKAGDVVLVIPFQNPEEQDEGWLMGVKESDWNQHKELEKCRGVFPENFTERVP cDNA with exons 1 to 6, 8 to 12, and 18 to 20 - named isoform
8 - without exon 17, which is BIN1 short muscle isoform
containing the muscle specific exon 11

SEQ ID NO: 27 atggcagagatgggcagtaaaggggtgacggcgggaaagatcgccagcaacgtgcagaagaag ctcacccgcgcgcaggagaaggttctccagaagctggggaaggcagatgagaccaaggatgag cagtttgagcagtgcgtccagaatttcaacaagcagctgacggagggcacccggctgcagaag gatctccggacctacctggcctccgtcaaagccatgcacgaggcttccaagaagctgaatgag tgtctgcaggaggtgtatgagcccgattggcccggcagggatgaggcaaacaagatcgcagag aacaacgacctgctgtggatggattaccaccagaagctggtggaccaggcgctgctgaccatg gacacgtacctgggccagttccccgacatcaagtcacgcattgccaagcgggggcgcaagctg gtggactacgacagtgcccggcaccactacgagtcccttcaaactgccaaaaagaaggatgaa gccaaaattgccaaggccgaggaggagctcatcaaagcccagaaggtgtttgaggagatgaat gtggatctgcaggaggagctgccgtccctgtggaacagccgcgtaggtttctacgtcaacacg ttccagagcatcgcgggcctggaggaaaacttccacaaggagatgagcaagctcaaccagaac ctcaatgatgtgctggtcggcctggagaagcaacacgggagcaacaccttcacggtcaaggcc cagcccagaaagaaagtaaactgttttcgcggctgcgcagaaagaagaacagtgacaacgcg cctgcaaaagggaacaagagcccttcgcctccagatggctcccctgccgccaccccgagatc agagtcaaccacgagccagagccggccggcggggccacgcccggggccaccctccccaagtcc ccatctcagagctctcttcctgctgtcgtggtggagaccttcccagcaactgtgaatggcacc gtggagggcggcagtggggccgggcgcttggacctgccccaggtttcatgttcaaggtacag gcccagcacgactacacggccactgacacagacgagctgcagctcaaggctggtgatgtggtg ctggtgatccccttccagaaccctgaagagcaggatgaaggctggctcatgggcgtgaaggag agcgactggaaccagcacaaggagctggagaagtgccgtggcgtcttccccgagaacttcact gagagggtcccatga AMINO ACID SEQUENCE - isoform 8 - without exon 17

SEQ ID NO: 28

MAEMGSKGVTAGKIASNVQKKLTRAQEKVLQKLGKADETKDEQFEQCVQNFNKQL

TEGTRLQKDLRTYLASVKAMHEASKKLNECLQEVYEPDWPGRDEANKIAENNDLL

WMDYHQKLVDQALLTMDTYLGQFPDIKSRIAKRGRKLVDYDSARHHYESLQTAKK

KDEAKIAKAEEELIKAQKVFEEMNVDLQEELPSLWNSRVGFYVNTFQSIAGLEEN

FHKEMSKLNQNLNDVLVGLEKQHGSNTFTVKAQPRKKSKLFSRLRRKKNSDNAPA

KGNKSPSPPDGSPAATPEIRVNHEPEPAGGATPGATLPKSPSQSSLPAVVVETFP

ATVNGTVEGGSGAGRLDLPPGFMFKVQAQHDYTATDTDELQLKAGDVVLVIPFQN

PEEQDEGWLMGVKESDWNQHKELEKCRGVFPENFTERVP cDNA with exons 1 to 6, 8 to 12, and 17 to 20 - named isoform
8 - with exon 17, which is BIN1 long muscle isoform
containing the muscle specific exon 11, and corresponds
to the NCBI isoform 8

SEQ ID NO: 29 atggcagagatgggcagtaaaggggtgacggcgggaaagatcgccagcaacgtgcagaagaag ctcacccgcgcgcaggagaaggttctccagaagctggggaaggcagatgagaccaaggatgag -continued

```
cagtttgagcagtgcgtccagaatttcaacaagcagctgacggagggcacccggctgcagaag gatctccggacctacctggcctccgtcaaagccatgcacgaggcttccaagaagctgaatgag tgtctgcaggaggtgtatgagcccgattggcccggcagggatgaggcaaacaagatcgcagag aacaacgacctgctgtggatggattaccaccagaagctggtggaccaggcgctgctgaccatg gacacgtacctgggccagttccccgacatcaagtcacgcattgccaagcgggggcgcaagctg gtggactacgacagtgcccggcaccactacgagtcccttcaaactgccaaaaagaaggatgaa gccaaaattgccaaggccgaggaggagctcatcaaagcccagaaggtgtttgaggagatgaat gtggatctgcaggaggagctgccgtccctgtggaacagccgcgtaggtttctacgtcaacacg ttccagagcatcgcgggcctggaggaaaacttccacaaggagatgagcaagctcaaccagaac ctcaatgatgtgctggtcggcctggagaagcaacacgggagcaacaccttcacggtcaaggcc cagcccagaaagaaaagtaaactgttttcgcggctgcgcagaaagaagaacagtgacaacgcg cctgcaaaagggaacaagagcccttcgcctccagatggctccctgccgccaccccgagatc agagtcaaccacgagccagagccgccggcggggccacgcccggggccaccctccccaagtcc ccatctcagccagcagaggcctcggaggtggcgggtgggacccaacctgcggctggagcccag gagccaggggagacggcggcaagtgaagcagcctccagctctcttcctgctgtcgtggtggag accttcccagcaactgtgaatggcaccgtggagggcggcagtggggccgggcgcttggacctg cccccaggtttcatgttcaaggtacaggcccagcacgactacacggccactgacacagacgag ctgcagctcaaggctggtgatgtggtgctggtgatccccttccagaaccctgaagagcaggat gaaggctggctcatgggcgtgaaggagagcgactggaaccagcacaaggagctggagaagtgc cgtggcgtcttccccgagaacttcactgagagggtcccatga
```

AMINO ACID SEQUENCE isoform 8 - with exon 17
SEQ ID NO: 30

MAEMGSKGVTAGKIASNVQKKLTRAQEKVLQKLGKADETKDEQFEQCVQNFNKQL

TEGTRLQKDLRTYLASVKAMHEASKKLNECLQEVYEPDWPGRDEANKIAENNDLL

WMDYHQKLVDQALLTMDTYLGQFPDIKSRIAKRGRKLVDYDSARHHYESLQTAKK

KDEAKIAKAEEELIKAQKVFEEMNVDLQEELPSLWNSRVGFYVNTFQSIAGLEEN

FHKEMSKLNQNLNDVLVGLEKQHGSNTFTVKAQPRKKSKLFSRLRRKKNSDNAPA

KGNKSPSPPDGSPAATPEIRVNHEPEPAGGATPGATLPKSPSQPAEASEVAGGTQ

PAAGAQEPGETAASEAASSSLPAVVVETFPATVNGTVEGGSGAGRLDLPPGFMFK

VQAQHDYTATDTDELQLKAGDVVLVIPFQNPEEQDEGWLMGVKESDWNQHKELEK

CRGVFPENFTERVP artificial cDNA sequence with exons 1 to 6; 8 to 10; 12 and
18-20 - named short isoform 9
SEQ ID NO: 31

```
atggcagagatgggcagtaaaggggtgacggcgggaaagatcgccagcaacgtgcagaagaag ctcacccgcgcgcaggagaaggttctccagaagctggggaaggcagatgagaccaaggatgag cagtttgagcagtgcgtccagaatttcaacaagcagctgacggagggcacccggctgcagaag gatctccggacctacctggcctccgtcaaagccatgcacgaggcttccaagaagctgaatgag tgtctgcaggaggtgtatgagcccgattggcccggcagggatgaggcaaacaagatcgcagag aacaacgacctgctgtggatggattaccaccagaagctggtggaccaggcgctgctgaccatg gacacgtacctgggccagttccccgacatcaagtcacgcattgccaagcgggggcgcaagctg gtggactacgacagtgcccggcaccactacgagtcccttcaaactgccaaaaagaaggatgaa gccaaaattgccaaggccgaggaggagctcatcaaagcccagaaggtgtttgaggagatgaat
```

-continued

```
gtggatctgcaggaggagctgccgtccctgtggaacagccgcgtaggtttctacgtcaacacg ttccagagcatcgcgggcctggaggaaaacttccacaaggagatgagcaagctcaaccagaac ctcaatgatgtgctggtcggcctggagaagcaacacgggagcaacaccttcacggtcaaggcc cagcccagtgacaacgcgcctgcaaaaggggaacaagagcccttcgcctccagatggctcccct gccgccaccccccgagatcagagtcaaccacgagccagagccggccggcggggccacgcccggg gccaccctccccaagtccccatctcagagctctcttcctgctgtcgtggtggagaccttccca gcaactgtgaatggcaccgtggagggcggcagtggggccgggcgcttggacctgcccccaggt ttcatgttcaaggtacaggcccagcacgactacacggccactgacacagacgagctgcagctc aaggctggtgatgtggtgctggtgatcccccttccagaaccctgaagagcaggatgaaggctgg ctcatgggcgtgaaggagagcgactggaaccagcacaaggagctggagaagtgccgtggcgtc ttccccgagaacttcactgagagggtcccatga
```

AMINO ACID SEQUENCE corresponding to cDNA sequence with exons
1 to 6, 8 to 10, 12, and 18 to 20 - named short isoform 9
SEQ ID NO: 32

MAEMGSKGVTAGKIASNVQKKLTRAQEKVLQKLGKADETKDEQFEQCVQNFNKQL

TEGTRLQKDLRTYLASVKAMHEASKKLNECLQEVYEPDWPGRDEANKIAENNDLL

WMDYHQKLVDQALLTMDTYLGQFPDIKSRIAKRGRKLVDYDSARHHYESLQTAKK

KDEAKIAKAEEELIKAQKVFEEMNVDLQEELPSLWNSRVGFYVNTFQSIAGLEEN

FHKEMSKLNQNLNDVLVGLEKQHGSNTFTVKAQPSDNAPAKGNKSPSPPDGSPAA

TPEIRVNHEPEPAGGATPGATLPKSPSQSSLPAVVVETFPATVNGTVEGGSGAGR

LDLPPGFMFKVQAQHDYTATDTDELQLKAGDVVLVIPFQNPEEQDEGWLMGVKES

DWNQHKELEKCRGVFPENFTERVP

Primer BIN1
SEQ ID NO: 33
ACGGCGGGAAAGATCGCCAG

Primer BIN1
SEQ ID NO: 34
TTGTGCTGGTTCCAGTCGCT

The following examples are given for purposes of illustration and not by way of limitation.

EXAMPLES

Abbreviations:
Aa or AA: amino acids; AAV: adeno-associated virus; DMSO: Dimethyl sulfoxide; EDTA: Ethylenediaminetetraacetic acid; HE: hematoxylin-eosin; KO: knockout; MTM: myotubularin MTMR: myotubularin-related; PPIn: phosphoinositides; PtdIns3P: phosphatidylinositol 3-phosphate; PtdIns(3,5)P2: phosphatidylinositol 3,5-bisphosphate; SDH: succinate deshydrogenase; SDS: Sodium dodecyl sulfate; TA: tibialis anterior; Tg: transgenic; WT: wild type.

1. Materials and Methods

1.1. Study Design

The sample size for each experiment is included in the figure legends. In this study, mice (WT and Mtm1−/y mice) and primary myoblasts were obtained from WT and Mtm1−/y pups. The number of mice used was selected based on previous phenotyping analysis conducted on the same model. Mtm1−/y mice died before 2-3 months so they were analyzed until 2 months. The other genotypes studied (WT, TgBIN1, Mtm1−/y TgBIN1 and Mtm1−/y injected with AAV-BIN1 systemically) were phenotyped and sacrificed at a certain age. Blind phenotyping tests were conducted on mice WT, TgBIN1, Mtm1−/y TgBIN1 and on primary cells. Each experiment was repeated at least 3 times. No outliers were excluded in the study.

1.2. Generation of Mtm1−/y Mice, and Mtm1−/y Tg BIN1 Mice

Mtm1−/y mouse line (129PAS) was previously generated and characterized (A. Buj-Bello et al., Proc Natl Acad Sci USA 99, 15060-15065, 2002; H. Tasfaout et al., Nat Commun 8, 15661, 2017). TgBIN1(B6J) mice were obtained by the insertion of human BAC (n° RP11-437K23 Grch37 Chr2: 127761089-127941604) encompassing the full BIN1 gene with 180.52 Kb of genomic sequence. Mtm1 heterozygous female mice were crossed with TgBIN1 males to generate 4 genotypes: WT, TgBIN1, Mtm1−/y TgBIN1 and Mtm1−/y. Animals were maintained at room temperature with 12 hours light/12 hours dark cycle. Animals were sacrificed by cervical dislocation following European legislation on animal experimentation and experiments approved by ethical committees (APAFIS #5640-2016061019332648; Com'Eth 01594, 2016031110589922).

1.3. Animal Phenotyping

Animal tests were performed weekly from 3 weeks to 16 weeks of age and monthly from 4 months to 12 months. Hanging test: The mice were suspended to a cage lid for 60 seconds. The test was repeated 3 times on average; Grip test: The 4 paws strength was measured using a dynamometer, the average of 3 repetitions was considered. Results are represented as force (g) relative to body weight in grams (g); Rotarod test: The mice performed the test for 5 days. On day 1, the mice were trained to run. From day 2 to day 5, the mice ran for a maximum of 5 minutes with increasing speed (4-40 rpm); Bar test: Mice were placed on a suspended bar. The time to walk along the bar was measured; Footprint test: 2 mice back paws were coloured with ink, and mice walked on a white paper. The angle of the footprint pattern was measured using ImageJ.

1.4. Muscle Force Measurement

Mice were anesthetized using Pentobarbitol (50 mg/kg) by intraperitoneal injection, the force of tibialis anterior (TA) was measured using a force transducer (Aurora Scientific), as previously described (H. Tasfaout et al., Nat Commun 8, 15661, 2017). TA absolute maximal force was measured after tetanic stimulation of the sciatic nerve with a pulse frequency from 1 to 125 Hz. Specific maximal force was determined dividing the absolute maximal force with the TA weight. Fatigue was measured stimulating continuously the sciatic nerve with a frequency of 50 Hz.

1.5. AAV Transduction of TA Muscle and Systemic Transduction

1.5.1. Intramuscular Injection 3 weeks-old male wild-type and Mtm1−/y 129PAS mice were anesthetized by intraperitoneal injection of ketamine (20 mg/ml) and xylazine 0.4% (5 μL/g of body weight). TA muscle was injected with 20 μL/g of AAV9-CMV-BIN1 isoform 8 without exon 17 (SEQ ID NO: 27) or with AAV9 empty Control diluted in PBS solution. The concentration injected was about 7×10^11vg/mL.

1.5.2. Systemic Injection

Pups were injected in the first 24 hours after birth. A volume of 50 μL of AAV-CMV-BIN1 isoform 8 without exon 17 (SEQ ID NO: 27) or with AAV9 empty Control was injected by i.p. The concentration injected was 10^13vg/mL. Pups were immediately housed in the cage with their mother.

1.5.3. Other AAV BIN1 Viral Vectors

Alternative AAV viral vectors (as described in the application) comprising other natural isoforms of BIN1 than isoform 8, or artificial cDNA BIN1 construct, were produced and tested, in particular BIN1 long isoform 9 represented by SEQ ID NO: 25.

1.6. Tissue Collection

Cervical dislocation was used to kill mice after carbon dioxide suffocation. TA and GAS (gastronecmius) were extracted and then frozen in cold isopentane cooled in liquid nitrogen. The diaphragm was collected and directly frozen in OCT in dry ice. Heart, liver and brain were collected and directly frozen in liquid nitrogen. All the tissues were then stored at −80° C.

1.7. Histology

8 μm slides (cryosections) of TA, GAS and diaphragm were cut in the cryostat and then stained with Haematoxylin and Eosin (HE) and succinate dehydrogenase (SDH) for histological analysis. After staining, images were acquired with the Hamamatsu Nano Zoomer 2HT slide scanner. The percentage of internalized nuclei were counted using Cell Counter Plugin in Fiji software. A Macro was used to measure the TA fiber diameter. The TA fiber meter was calculated (500 fibers per mouse) based on 3-5 mice per group. The percentage of TA muscle fibers with centralized or internalized nuclei was counted in 500 fibers using the cell counter plugin in Image.

1.8. Immunostaining

Transversal section was obtained from TA frozen in isopentane and then cut on the cryostat at 8 μm. For longitudinal staining, the TA was incubated overnight in PFA at 4° C. and after 3 PBS 1X washing transferred into 30% sucrose overnight at 4° C. The sections were permeabilised with PBS-Triton 0.5% and then blocked with BSA 5% in PBS.

Primary antibodies diluted in BSA 1% used were: Dystrophin (ab15277, Abcam), Laminin (ab11575, Abcam; 1:200), EEA1 (sc-137130, Santa Cruz Biotechnology, Inc.; 1:50), Alpha 7 Integrin (ab195959, Abcam; 1:50), Beta1 Integrin (MAB1997, Chemicon; 1:50), Vinculin (V9131, Sigma; 1:200), DHPR1a (abcam2862. 1: 50, Abcam; 1:50), BIN1 (C99D, Abcam; 1:50), anti-BIN1 (R2405, IGBMC), GAPDH (MAB374, Chemicon), Collagen VI (NB120-6588, Novus Biologicals), FAK (3285S, Cell Signaling), pY397FAK (44-624G, Invitrogen), Rhodamine Phalloidin (PHDR1, Cytoskeleton), Rabbit anti-DNM2 antibodies (R2680 and R2865, IGBMC).

Alexa Fluor-conjugated secondary antibodies were purchased from Invitrogen: Alexa Fluor 488 (AA11001 and A11008), Alexa Fluor 594 (A11005 and A1112) and Alexa Fluor 647 (A32728). Secondary antibodies against mouse and rabbit IgG, conjugated with horseradish peroxidase (HRP) were purchased from Jackson ImmunoResearch Laboratories. An ECL kit was purchased from Pierce. Secondary antibodies were diluted 1:250 in 1% BSA.

1.9. Electron Microscopy

TA was stored in 2.5% paraformaldehyde, 2.5% glutaraldehyde in 0.1M cacodylate buffer. The section was observed by electron microscopy (EM). To observed T-tubules, potassium ferrocyanide was added to the buffer (K3Fe (CN) 6 0.8%, Osmium 2%, cacodylate 0.1M). The triad number per sarcomere and T-tubule direction were measured manually.

1.10. RNA Extraction and BIN1 Isoform 8 Detection

TA was lysed in TRIzol reagent (Invitrogen, UK) to extract RNA and the Reverse Transcriptase (Thermofisher Scientific) was used to obtain cDNA. To identify human BIN1 isoform overexpressed in Mtm1−/y Tg BIN1 mice, BIN1 cDNA was amplified using human BIN1 primers (SEQ ID NO: 33: ACGGCGGGAAAGATCGCCAG, SEQ ID NO: 34: TTGTGCTGGTTCCAGTCGCT). Human BIN1 cDNA was cloned into the pENTR1A vector and then sequenced using GATC service (Germany).

1.11. Protein Extraction and Western Blotting

TA muscle was lysed in RIPA buffer with DMSO 1 mM, PMSF 1 mM and mini EDTA free protease inhibitor cocktail tablets (Roche Diagnostic), on ice. The protein concentration was measured using the BIO-RAD Protein Assay Kit (BIO-RAD). Loading buffer (50 mM Tris-HCl, 2% SDS, 10% glycerol) was added to protein lysates, and proteins were separated by 8% or 10% in SDS-polyacrylamide gel electrophoresis containing 2,2,2-Trichloroethanol (TCE, Aldrich) in order to visualize all tryptophan-containing proteins. After transfer to nitrocellulose, saturation was done with 3% BSA or 5% milk, primary antibody and secondary antibody was added: Beta1 integrin (MAB1997, 1:500), vinculin (V9131, 1:1000), BIN1 (2405, 1:1000; IGBMC), MTM1 (2827, 1:1000; IGBMC), GAPDH (MAB374, 1:100000).

1.12. Primary Myoblasts

Primary myoblasts from WT and Mtm1−/y newborn mice were prepared as previously described. After extraction, primary cells were plated in IMDM with 20% FCS and 1%

Chicken Embryo Extract (MP Biomedical) onto 1:200 Matrigel Reduced Factor (BD) and Laminin (354232, Corning).

1.13. Primary Myoblasts Adhesion Experiments

The experiments were conducted following the protocol adapted from Ratcliffe et al, Traffic 17, 670-688 (2016). WT and Mtm1−/y primary myoblast were trypsinized and resuspended in IMDM with 20% FCS and 1% Chicken Embryo Extract. 2,5×104 primary myoblasts were diluted in 500 µl media and plated in laminin coated dishes. Cells were allowed to adhere for 10, 20, 30 and 60 minutes. Primary myoblasts were then washed with warmed medium and fixed with 4% PFA. Immunofluorescence was conducted and cells were stained with Rhodamine Phalloidin (Cystoskeleton). After confocal acquisition cells surface were measured using ImageJ program.

1.14. Primary Myoblasts Fusion Index

Primary myoblasts were plated at 4×104 on matrigel. Primary myoblasts differentiation was triggered when cells reach 70% by switching the medium to IMDM with 2% horse serum and 24 hours later a thick layer of matrigel (1:3 in IMDM) was added. Brightfield picture were acquired in living myotubes at 24, 48 and 72 hours post differentiations.

1.15. Primary Myoblasts Migration

2×104 primary myoblasts were plated in IMDM with 20% FCS and 1% Chicken Embryo Extract on laminin coated dishes. Migration of cells were observed in Time lapse Leica microscope for 24 hours, Pictures were taken every 15 minutes. The migration velocity was measured using Fiji program.

1.16. Statistical Analysis

The data are expressed as mean±s.e.m. Graph and curves were made using GraphPad Prism software version 5 and 6. The unpaired students T-test was used to analysing two groups; one-way ANOVA and Bonferroni test was used to compare different groups. P values smaller than 0.05 were considered significant. The number of mice is listed for each experiment in the Figures legend.

2. Results 2.1. Overexpression of Human BIN1 Rescues Mtm1−/y Survival

Figure 1:
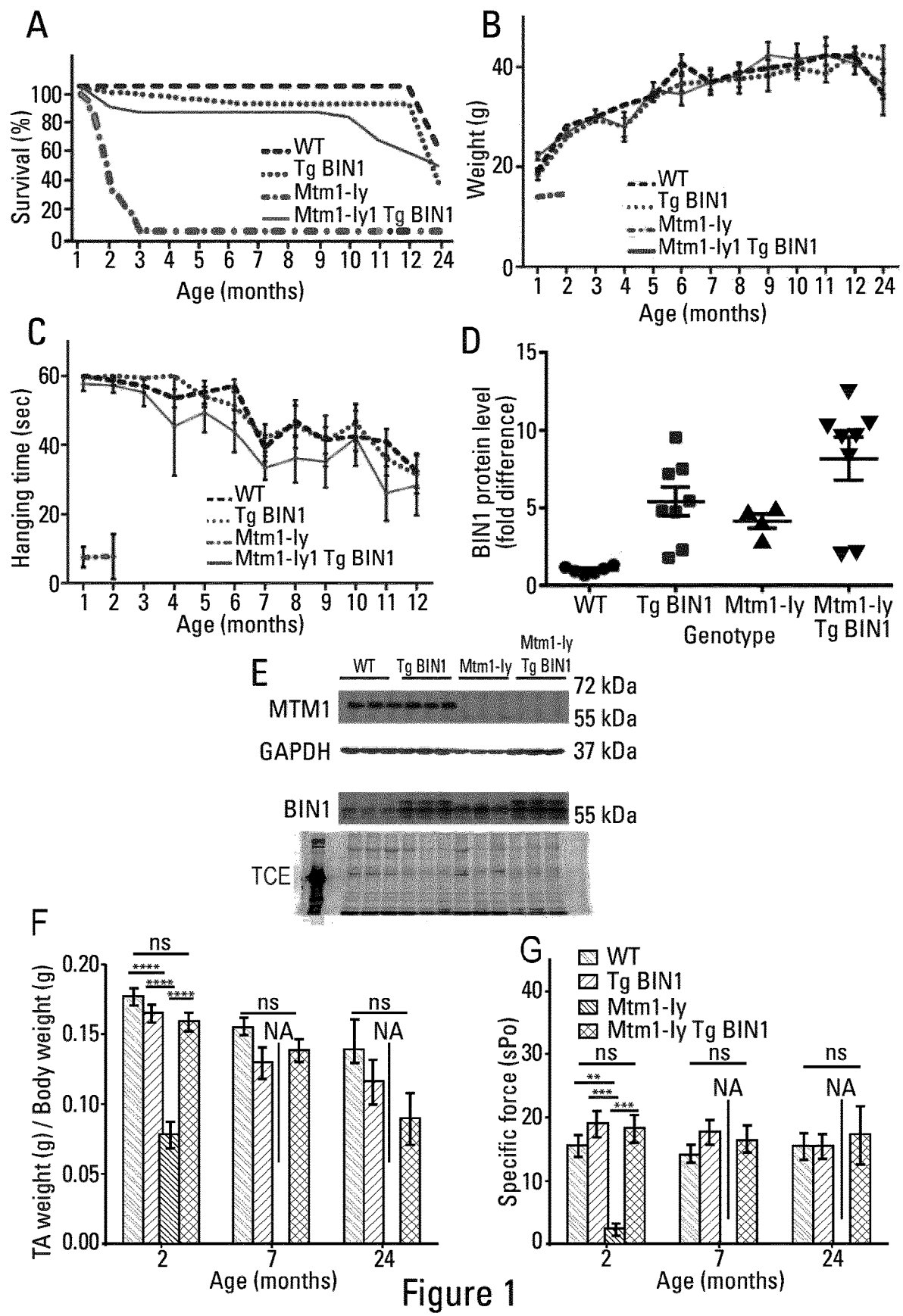
FIG. 1: Overexpression of BIN1 rescues the lifespan defect in Mtm1−/y mice. BIN1 isoform 8 of sequence SEQ ID NO: 27 has been used herein. (A) Lifespan of the mice analyzed (represented as survival percentage). (B) Body weight with age (n>5). (C) Hanging test. Mice were suspended from a cage lid for maximum 60s, and each mouse repeated the test three times (n>5). (D) BIN1 quantification normalized on TCE (2,2,2-Trichloroethanol) fluorescence labelling all tryptophan-containing proteins. (E) Western blot from Tibialis Anterior (TA) muscle lysate probed with anti-BIN1 and MTM1 antibodies; protein level showed in WT, Tg BIN1, Mtm1−/y, Mtm1−/y Tg BIN1 mice, normalized on GAPDH. (F) Weight of Tibialis Anterior (TA) muscle, represented as a percentage of the total body weight. (G) Specific muscle force of the TA; the test was performed at 2 months (n>5), 7 months (n>5) and at 24 months (n=4). NA: not applicable as Mtm1−/y mice died before. Statistic test: One-Way Anova, Bonferroni post-hoc test; ns: not significant, *p<0.05,  p<0.01, *p<0.001.

Mtm1−/y mice die in the first 2 months of age due to a severe and progressive skeletal muscle phenotype resembling XLCNM, as previously reported (Buj-Bello A et al., Proc Natl Acad Sci USA. 2002 Nov. 12; 99(23):15060-5. Epub 2002 Oct 21). To test if the overexpression of BIN1 could rescue the survival of Mtm1−/y mice, transgenic mice expressing the human BIN1 gene (Tg BIN1) were created by insertion of a human bacterial artificial chromosome (BAC) containing the human BIN1 gene with its flanking sequence into the mouse genome. RT-PCR, cloning and sequencing from tibialis (TA) muscle showed the presence of the human BIN1 isoform 8 (data not shown), that is the main muscle isoform. Approximately 4-fold overexpression of BIN1 was found (FIGS. 1D-1E). TgBIN1 mice were viable with no overt motor phenotypes (data not shown). Crossing TgBIN1 with Bin1−/− mice that die at birth from muscle defects efficiently rescued the lethality. No difference was observed in body weight, tibialis anterior (TA) weight and specific muscle force between WT and Bin1−/− TgBIN1 mice at 4 months (data not shown), showing that human BIN1 is functional in a mouse context.

Surprisingly, most Mtm1−/y Tg BIN1 mice survived for more than 12 months (at least 2 years old) similarly to the control genotypes WT and Tg BIN1, while Mtm1−/y mice died before 2 months of age (FIG. 1A). Additionally, there was no difference in body weight between WT, Tg BIN1 and Mtm1−/y Tg BIN1 mice throughout their 24 months lifespan, whilst Mtm1−/y mice weighted significantly less at comparable age (FIG. 1B). These results suggest that the increase of BIN1 rescues the early lethality of Mtm1−/y mice.

BIN1 level was increased by about 4-fold in Mtm1−/y Tg BIN1 mice compared to WT (FIGS. 1D-1E). These results show that an increased expression of BIN1 rescues the postnatal lethality and growth defect observed in Mtm1−/y mice.

2.2. Overexpression of BIN1 Rescues Muscle Strength and Coordination in Mtm1−/y Mice Since the overexpression of BIN1 in Mtm1−/y mice rescued the lifespan of Mtm1−/y mice, it was then investigated whether the survival correlated with an improvement in total muscle strength. Various functional tests were performed in all four genotypes. The hanging test requires mice to be suspended to a grid for 60 sec. Mtm1−/y mice could not perform this test, whereas Mtm1−/y Tg BIN1 mice were able to complete the test similarly to WT and Tg BIN1 mice (FIG. 1C). The grip test was performed to understand the maximal leg strength. Only after 4 months of age, a slight decrease was identified in Mtm1−/y Tg BIN1 mice compared with WT and Tg BIN1 mice (data not shown). To evaluate if the general motor coordination was rescued thanks to the overexpression of BIN1 in Mtm1−/y mice, rotarod, footprint and bar test were performed at 5 weeks and 5 months of age. Rotarod was performed for 4 days, mice run for max 5 minutes in a crescent acceleration and the time that mice could run was registered. At 5 weeks of age WT, Tg BIN1 and Mtm1−/y Tg BIN1 mice could run between 2 to 3 minutes for the 4 days of trial, and perfectly completed the bar test, whilst Mtm1−/y mice decreased their performance with time and reached maximum 50 seconds on the rotarod test (data not shown). More particularly, at 5 weeks, Mtm1−/y mice exhibited strong defects in hanging (whole body strength), rotarod (coordination and resistance to exercise), bar walking (they could not walk on the bar) and foot print (coordination) tests (FIG. 1C, and data not shown). At 5 months, Mtm1−/y Tg BIN1 mice were still able to perform all the tests (hanging, rotarod, and foot print) and they slightly improved the time spent on the rotarod during the 4 days of trials (FIG. 1C, and data not shown), indicating a long-term improvement in their motor function.

Increased expression of BIN1 in Mtm1−/y mice which normally present with strong muscle atrophy, rescued the TA muscle atrophy back to WT level (FIG. 1F). Specific muscle force, measured in situ in the TA muscle, was extremely low in Mtm1−/y mice at 2 months, and rescued to WT levels in 2, 7 and 24 months old Mtm1−/y TgBIN1 mice (FIG. 1G, and data not shown). The time to muscle exhaustion during continuous stimulation was similar between Mtm1−/y TgBIN1 and WT mice at 2 and 7 months of age (data not shown). Overall, the severe coordination and muscle weakness phenotypes of Mtm1−/y mice were completely rescued by overexpressing BIN1 in Mtm1−/y mice.

2.3. Histological Features of XLCNM are Rescued by Overexpressing BIN1 in Mtm1−/y Mice At 8 weeks of age, Mtm1−/y TA muscles present with small rounded fibers with abnormal subsarcolemmal and central accumulation of oxidative staining (FIG. 2A). Fiber size distribution (minimum ferret) was biased towards small fibers (peak diameter 20-25 µm), whilst it increased to 25-30 µm in Mtm1−/y Tg BIN1, similar to WT and Tg BIN1 muscles (FIG. 2C). Mtm1−/y TA muscles displayed about 20-30% of fibers with abnormal nuclei position (including internalized and centralized nuclei), whereas Mtm1−/y Tg BIN1 had only 2% of abnormal nuclei and were indistinguishable from WT (FIG. 2B). Similar defects in Mtm1−/y mice were found in other muscles (gastrocnemius, diaphragm) and were efficiently rescued to WT levels in Mtm1−/y TgBIN1 mice (data not shown). Later, at 7 months of age, no difference was found in TA and gastronecmius muscles between Mtm1−/y TgBIN1 mice and WT mice (data not shown). To sum up, the TA muscle force and histology of Mtm1−/y Tg BIN1 supported that the overexpression of BIN1 rescues the main histological muscle feature of XLCNM in mice.

2.4. Increasing BIN1 Level in Mtm1−/y Mice Improves Muscle TA Ultrastructure

Figure 2:
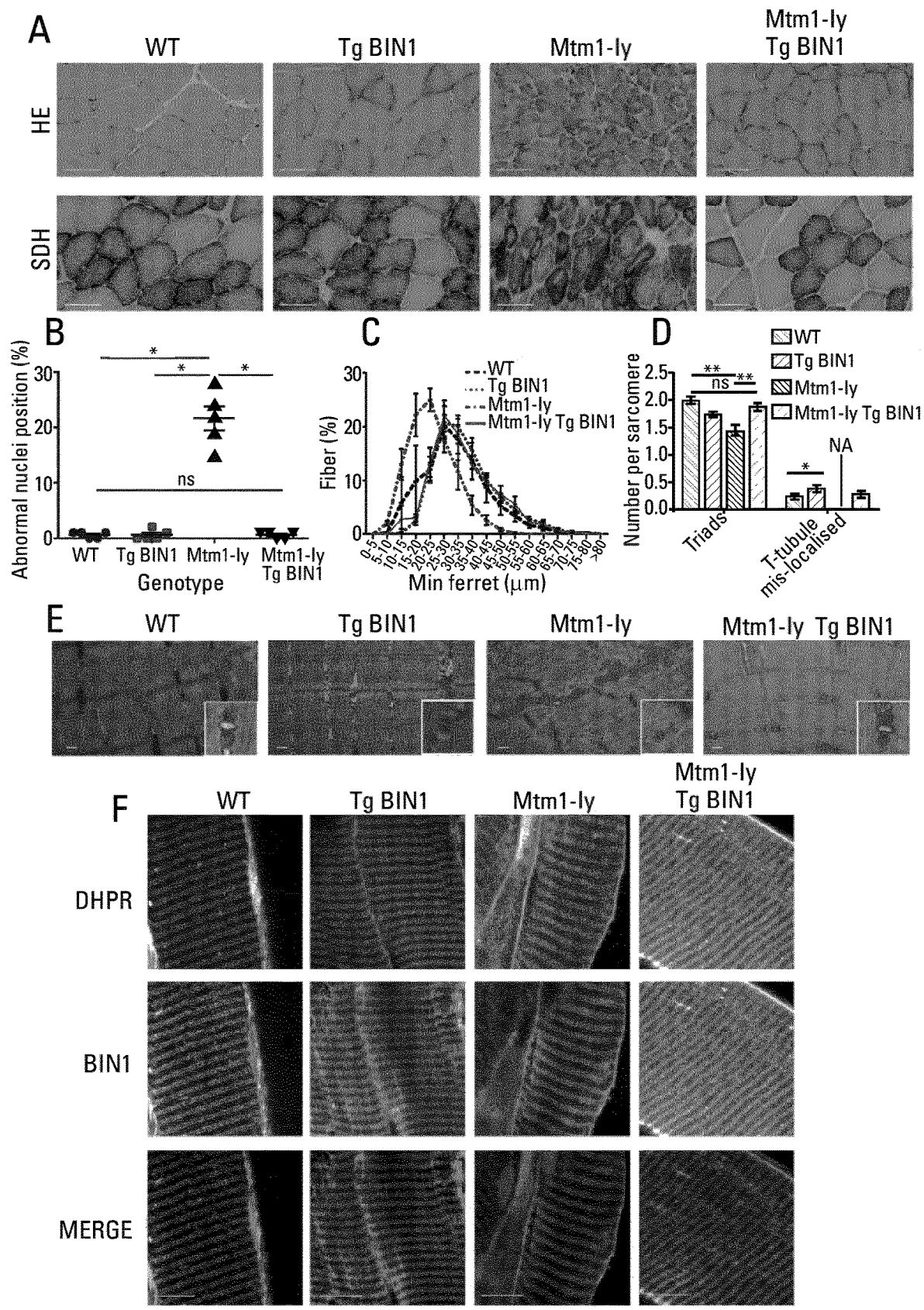
FIG. 2: Overexpression of BIN1 rescues the histology and ultrastructure in Mtm1−/y mice at 8 weeks old. BIN1 isoform 8 of sequence SEQ ID NO: 27 has been used herein. (A) Transversal TA muscle sections stained with HE and SDH; scale bar 500 µm. (B) Frequency of fibers with abnormal (internalized and centralized) nuclei in TA (n=5). (C) Minimum ferret of TA fibers grouped into 5 µm intervals (n=5). (D) Analysis of muscle ultrastructure. Frequency of triads counted for each sarcomere; frequency of T tubule mis-localised. (E) TA muscle ultrastructure observed by electron microscopy (EM). Scale bar 1 µm. High magnification insert for triads. (F) Longitudinal TA muscle sections stained with DHPR and BIN1 antibodies (2 months old mice). Images were acquired by confocal microscopy. Scale bar 10 µm. Statistic test: One-Way Anova, Bonferroni post-hoc test; ns: not significant, *p<0.05, ** p<0.01.

Based on the results that Mtm1−/y Tg BIN1 mice are as strong as the WT control and have no abnormalities in TA muscle histology, it was checked whether muscle organization was rescued in Mtm1−/y Tg BIN1. Pictures of TA muscle sections of WT, Tg BIN1, Mtm1−/y and Mtm1−/y Tg BIN1 mice were acquired by transmission electron microscopy (TEM) at 8 weeks of age to assess myofiber organization (FIG. 2E). In contrast to Mtm1−/y mice that had misaligned Z line, altered mitochondria position and shape, and general sarcomere disorganization, Mtm1−/y Tg BIN1 mice had aligned Z line and no abnormality in mitochondria. In other words, Mtm1−/y Tg BIN1 mice displayed normal myofiber ultrastructure. A fundamental structure in skeletal muscle are the triads which are involved in excitation and contraction coupling in skeletal muscle and are formed by one T-tubule and two sarcoplasmic reticulum (SR) cisternae. As BIN1 is known as a fundamental player in T-tubule biogenesis, it was next analyzed whether the overexpression of BIN1 had an impact on T-tubules and triads structure. Mtm1−/y TA muscle was very disorganized and it was difficult to distinguish the triads structure. However, normal triads, T-tubule shape and localization were observed in Tg BIN1 and Mtm1−/y Tg BIN1 mice (FIG. 2).

To confirm the correct organization of triads and T-tubule in the TA muscle, longitudinal TA muscle sections stained by BIN1 and DHPR were observed by immunofluorescence. BIN1 and the T-tubule receptor DHPR colocalized at T-tubules in the WT, Tg BIN1 and Mtm1−/y Tg BIN1 mice, whereas Mtm1−/y mice had some fibers with disorganized staining (FIG. 2F). In addition, Tg BIN1 and Mtm1−/y Tg BIN1 mice also exhibited longitudinal BIN1 and DHPR stainings that could correspond to the misorientated T-tubules (FIG. 2F); the same abnormal T-tubule localization was already observed during the T-tubule analysis on EM picture. Of note, human BIN1 is thus localizing as expected on the T-tubules. Next, it was analyzed the localization of Desmin which had been observed aggregating in the middle of the fibers in Mtm1−/y TA muscle. Mtm1−/y Tg BIN1 TA muscle had a normal distribution of Desmin in proximity of the plasma membrane and inside the fibers, as WT. To conclude, overexpression of BIN1 rescued the TA muscle ultrastructure observed in Mtm1−/y mice.

2.5. Postnatal Muscular Overexpression of Human BIN1 Rescues Muscle Force and Myofiber Atrophy in Mtm1−/y Mice The overexpression of BIN1 from early embryonic age in Mtm1−/y mice rescued the survival and all CNM hallmarks, such as muscle strength. A crucial point was to identify the correct isoform of BIN1 that allowed the rescue even when expressed after birth. The human BIN1 isoform 8 without the exon 17 was the main human isoform overexpressed in the TA of Mtm1−/y Tg BIN1 mice, and was cloned into an AAV9 vector. Next, this human BIN1 isoform was overexpressed only in the TA muscle to test if the acute overexpression of BIN1 after birth could rescue TA muscle force, histology and muscle ultrastructure. To do so, 3-weeks old WT and Mtm1−/y mice were injected intramuscularly (in TA muscles) with AAV-BIN1 and Control empty AAV virus. In situ force analysis were performed 2-weeks and 4-weeks post-injection. In the injected muscles, BIN1 was expressed approximately 4-fold higher than in control muscles (FIG. 3H).

Figure 3:
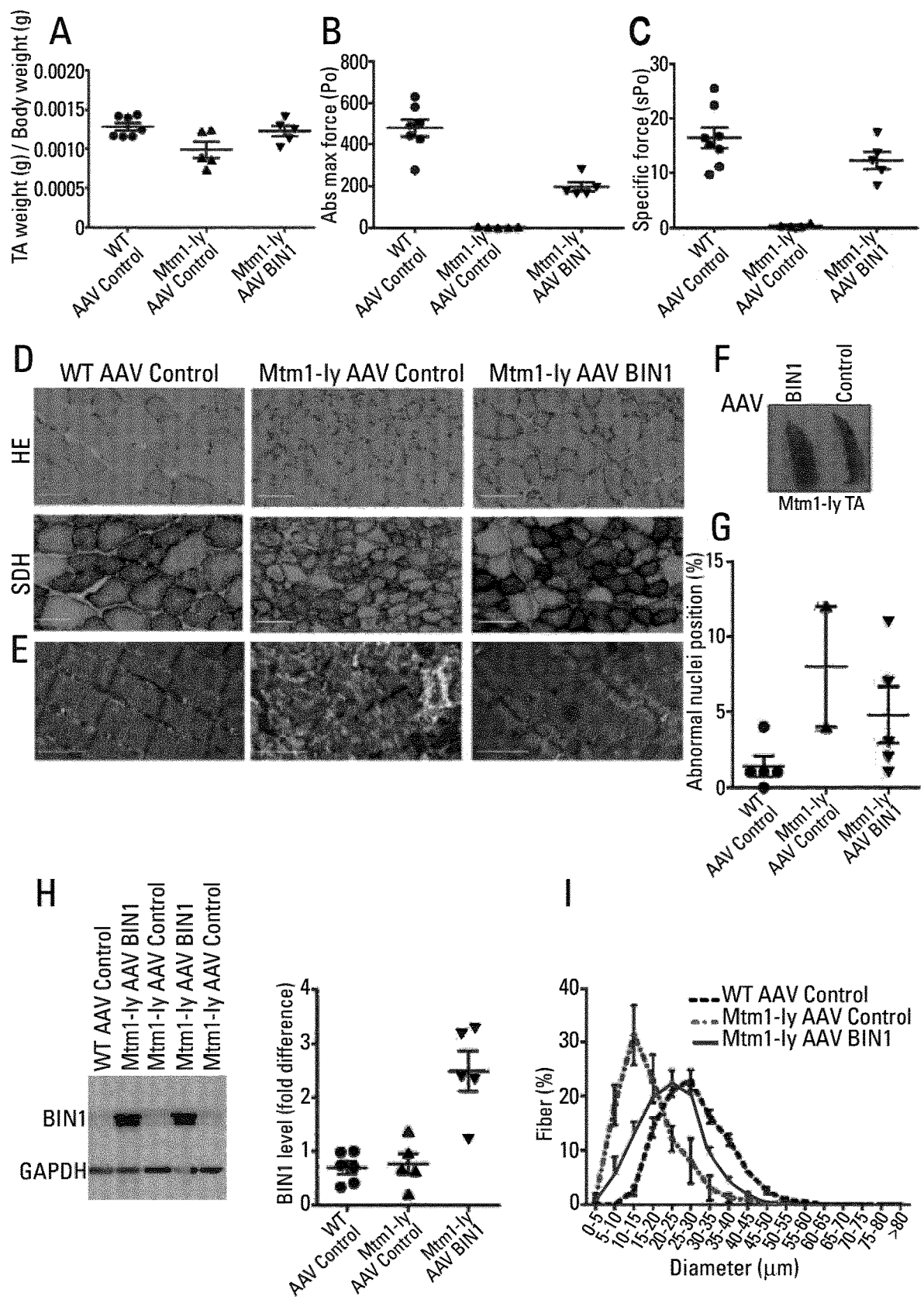
FIG. 3: Postnatal intramuscular overexpression of BIN1 with AAV rescues muscle atrophy and specific muscle force in Mtm1−/y mice. Mtm1−/y mice were injected at 3 weeks old with either AAV empty as Control or with AAV-BIN1 (BIN1 isoform 8 of sequence SEQ ID NO: 27, or BIN1 long isoform 9 of sequence SEQ ID NO: 25); mice were analyzed 2 weeks post-injection except stated otherwise. (A) Percentage of the ratio of TA muscle on the mouse body weight (n≥5) (BIN1 isoform 8). (B) Maximal TA muscle force (n≥5). (C) Specific muscle TA force (n≥5) (BIN1 isoform 8). (D) Transversal TA sections stained with HE and SDH. Scale bar 500 µm (BIN1 isoform 8). (E) TA muscle longitudinal ultrastructure observed by electron microscopy (EM). Scale bar 1 µm. (BIN1 isoform 8). (F) Pictures of Mtm1−/y mouse TA muscle fibers: On the left, TA muscles injected with AAV BIN1, on the right, TA muscles injected with AAV Control, both observed 5 weeks post-injection (BIN1 isoform 8). (G) Frequency of fibers with abnormal (internalized and centralized) nuclei position in TA of WT Control mice and Mtm1−/y mice (n≥2) (BIN1 isoform 8). (H) Western-blot with anti-BIN1 antibody (left panel). BIN1 protein level (fold difference) observed in WT, Mtm1−/y, and normalized on GAPDH (right panel) (BIN1 isoform 8). (I) Minimum ferret of TA fibers grouped into 5 µm intervals (n=5). Scale bar 1 µm. (BIN1 isoform 8). (J) Specific muscle force of WT and Mtm1−/y mice injected with AAV empty Control or AAV-BIN1 long isoform 9. Statistic test: One-Way Anova, Bonferroni post-hoc test; ns: not significant, *p<0.05,  p<0.01, *p<0.001.
Figure 3:
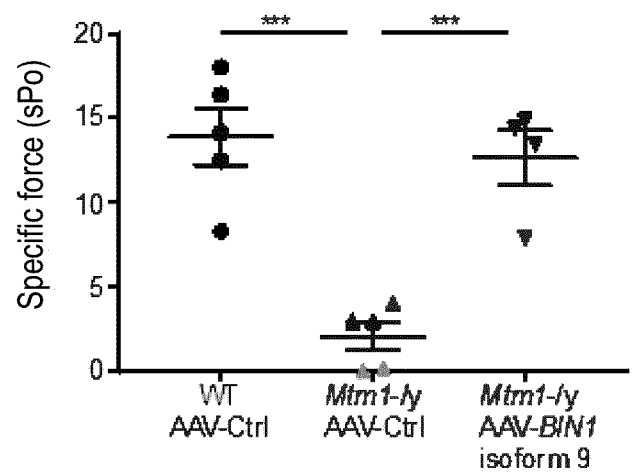

2-weeks post-injection, a significant increase in skeletal muscle TA force was noted in Mtm1−/y mice injected with AAV-BIN1 (FIGS. 3B-3C, 3J). No significant difference was observed in TA muscle weight of Mtm1−/y injected with AAV BIN1 compared to AAV Control (FIG. 3A). However, AAV-BIN1 greatly improved the general aspect of the muscle (HE), including the oxidative staining (SDH), fiber size (fiber diameter increased), and to a lesser extent nuclei position (nuclei position was not fully rescued) (FIGS. 3D, 3G and 3I). To determine if the overexpression of BIN1 after birth allowed a rescue in muscle ultrastructure, electron microscopy (EM) of TA injected with AAV-BIN1 and AAV-Control was performed. As expected, Mtm1−/y mice displayed severe defects of muscle organization. By contrast, TA muscle injected with AAV-BIN1 was organized as well as the WT TA muscle injected with the AAV-Control (FIG. 3E). In other words, myofiber organization was improved in Mtm1−/y mice injected with AAV-BIN1 compared with AAV-empty Control.

Similar effects were observed at 4 weeks post-injection (data not shown).

Overall, these results show that the intramuscular overexpression of BIN1 after birth is sufficient to achieve a strong improvement in muscle force, and myofiber organization (TA fiber size, TA muscle ultrastructure) in the Mtm1−/y mice. This strongly suggests that increased BIN1 after completion of embryogenesis is sufficient to significantly improve the myopathy phenotype in Mtm1−/y mice.

2.6. Postnatal Systemic Overexpression of BIN1 Prolongs Mtm1−/y Life Span

Figure 4:
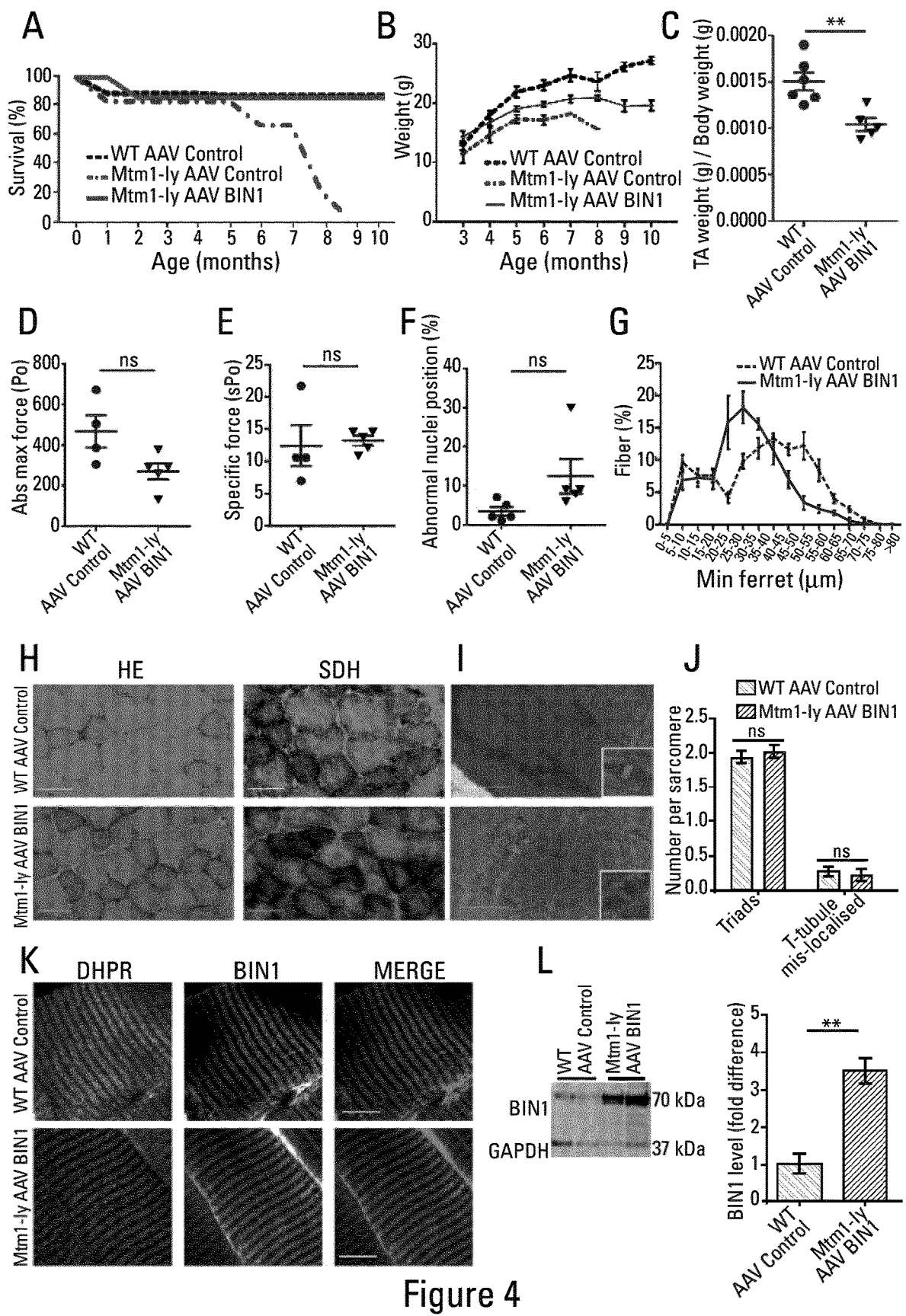
FIG. 4: Postnatal systemic BIN1 overexpression rescue the survival and muscles defect of Mtm1−/y mice. Mtm1−/y mice were injected at P1 with either AAV empty as Control or with AAV-BIN1 (BIN1 isoform 8 of sequence SEQ ID NO: 27); mice were analyzed at 10 weeks. (A) Percentage of mice survival before sacrifice at 10 weeks. (B) Body weight. (C) Ratio of TA muscles weight on mouse total body weight (n≥5). (D) Absolute maximal TA muscle force (n≥4). (E) Specific TA muscle force (n≥4). (F) Percentage of fibers with abnormal (internalized or centralized) nuclei (n=5). (G) Minimum ferret of TA fibers grouped into 5 µm intervals (n≥3). (H) Transversal TA muscle sections stained with HE an SDH. Scale bar 500 µm (I) Longitudinal TA muscle ultrastructure. T-tubule marked with ferrocyanate and pictures acquired by TEM. Scale bar 1 µm. High magnification insert for triads (J) Analysis of muscle ultrastructure: Frequency of triads counted for each sarcomere; frequency of T tubule mis-localized. (K) Longitudinal TA muscle sections stained with DHPR and BIN1 antibody. Images were acquired by confocal microscopy. Scale bar 10 µm. (L)Western Blot probed with anti BIN1 and GAPDH antibodies (left panel). The graph shows the overexpression of BIN1 on GAPDH (right panel). Statistic test: T-test; ns: not significant, ** p<0.01.

After having proved a striking increase of TA force due to AAV-BIN1 injected intramuscularly, it was decided to further investigate if systemic overexpression of BIN1 could rescue the lifespan of Mtm1−/y mice. AAV-BIN1 or AAV-Control were injected into pups postnatally at day 1 by intraperitoneal injection. Mouse weight and survival were measured weekly until 10 weeks of age. Surprisingly, the systemic overexpression of BIN1 post-birth rescued the premature death of Mtm1−/y mice (FIG. 4A). Interestingly, a slight increase of body weight was registered for Mtm1−/y mice injected with AAV-BIN1 during the period studied compared to mice injected with AAV Control (FIG. 4B). To sum up, the overexpression of BIN1 in Mtm1−/y mice after birth prolonged their lifespan.

2.7. Postnatal Systemic Overexpression of BIN1 Rescues TA Muscle Force in Mtm1−/y Mice Mtm1−/y mice survival was rescued by overexpression of BIN1 after birth. Phenotyping was then performed. The oldest treated Mtm1−/y mouse is now 1 year-old. None of the Mtm1−/y mice injected with AAV-BIN1 displayed ptosis and kyphosis, which are typical features observed in Mtm1−/y from 4 weeks of age (data not shown). To evaluate if the positive effect on growth and survival was correlated with an increase in muscle mass, function and structure, TA and GAS muscles were extracted at 10 weeks of age. Overexpression of BIN1 in the AAV-BIN1 injected animals was verified (FIG. 4L). Ratio of TA weight and body weight revealed the weight of Mtm1−/y TA injected with AAV-BIN1 was slightly lower compared to WT control (FIG. 4C). No significant difference was observed in situ in TA absolute force or TA specific muscle force or time to fatigue between Mtm1−/y mice injected with AAV-BIN1 and WT mice injected with AAV-Control (FIGS. 4D, 4E, and data not shown), indicating a complete rescue in muscle force These results thus strongly suggest that BIN1 overexpression improves the TA muscle force in Mtm1−/y mice.

2.8. Mtm1−/y Mice Injected with AAV-BIN1 have No Atrophy but Some Histological Features Typical of XLCNM The histological features of XLCNM were rescued in mice overexpressing BIN1 from early embryogenesis and in Mtm1−/y mice injected intramuscularly at 3 weeks of age. To assess if the systemic overexpression of BIN1 after birth rescued the abnormal nuclei position and fiber size in Mtm1−/y mice, the TA at 10 weeks of age was analyzed. No muscle atrophy was identified in WT and Mtm1−/y mice injected with AAV-BIN1 (general organization and oxidative staining were normal), but Mtm1−/y mice injected with AAV-BIN1 nevertheless displayed about 15% increase in abnormal nuclei position as well as a reduced fiber size compared to WT (FIGS. 4F-4H). Of note, the histological features of these treated Mtm1−/y mice appeared partially rescued (FIGS. 4F-4H), compared to 8-w old untreated mice (FIG. 2).

To understand if the ultrastructure of Mtm1−/y mice was rescued, the TA was checked with the EM (FIG. 4I) and TEM (transmission electron microscopy) (data not shown). The TA ultrastructure analysis revealed that the sarcomere organization was rescued by overexpression of BIN1 in Mtm1−/y, and the number of triads per sarcomere was normalized, with most triads presenting a normal shape and localization (FIGS. 4I-4J). The correct T-Tubule organization was confirmed by BIN1 and DHPR stainings of longitudinal TA muscle sections: BIN1 and DHPR seemed localized parallel to the Z line in the WT and in Mtm1−/y mice injected with AAV BIN1 (FIG. 4K). To summarize, the histology and ultrastructure analysis of Mtm1−/y mice receiving a systemic injection of AAV-BIN1 indicated that overexpression of BIN1 after birth rescued muscle atrophy and TA muscle ultrastructure defects. However, Mtm1−/y mice still had more centralized nuclei compared to the WT controls.

Figure 5:
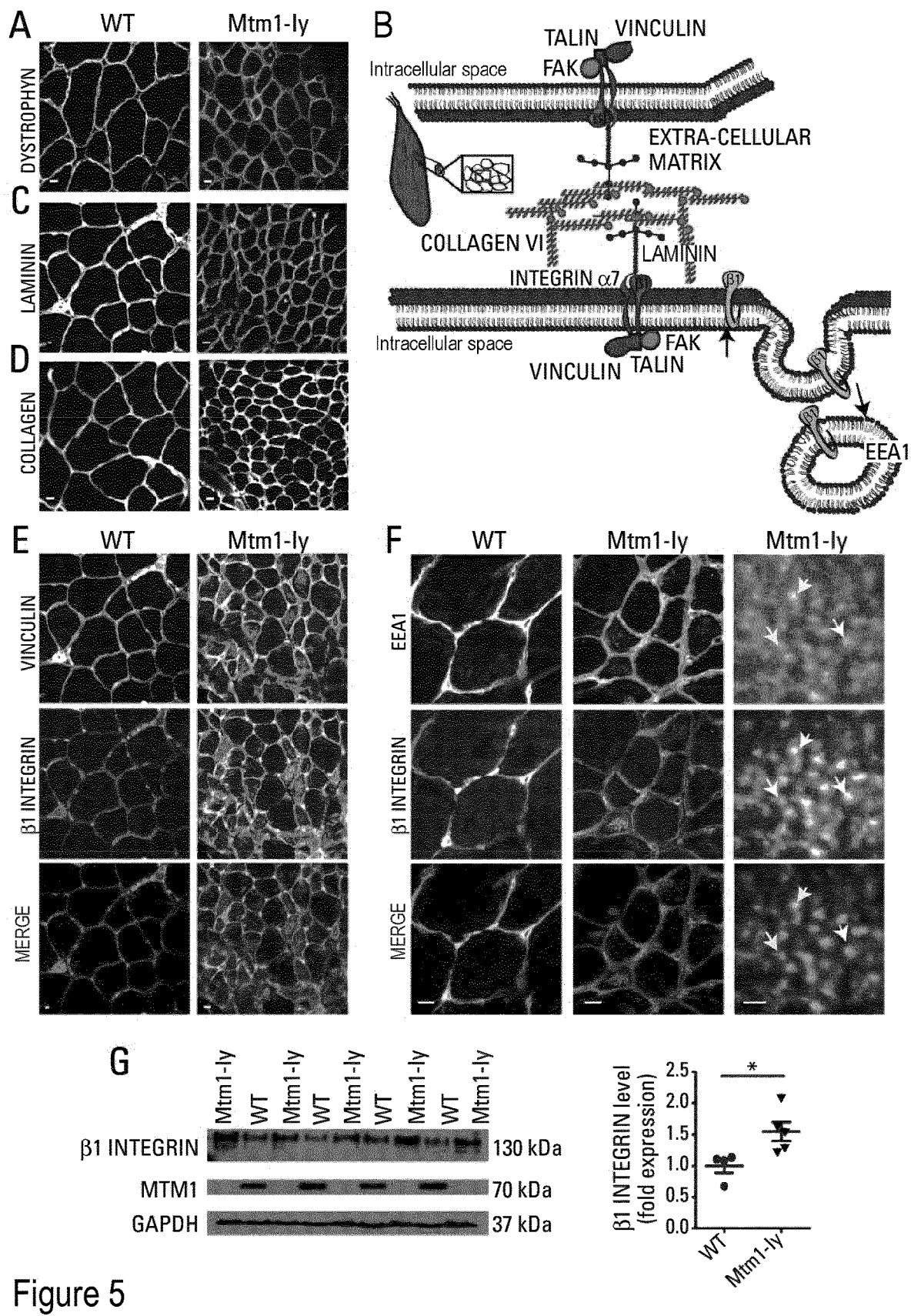
Figure 5:
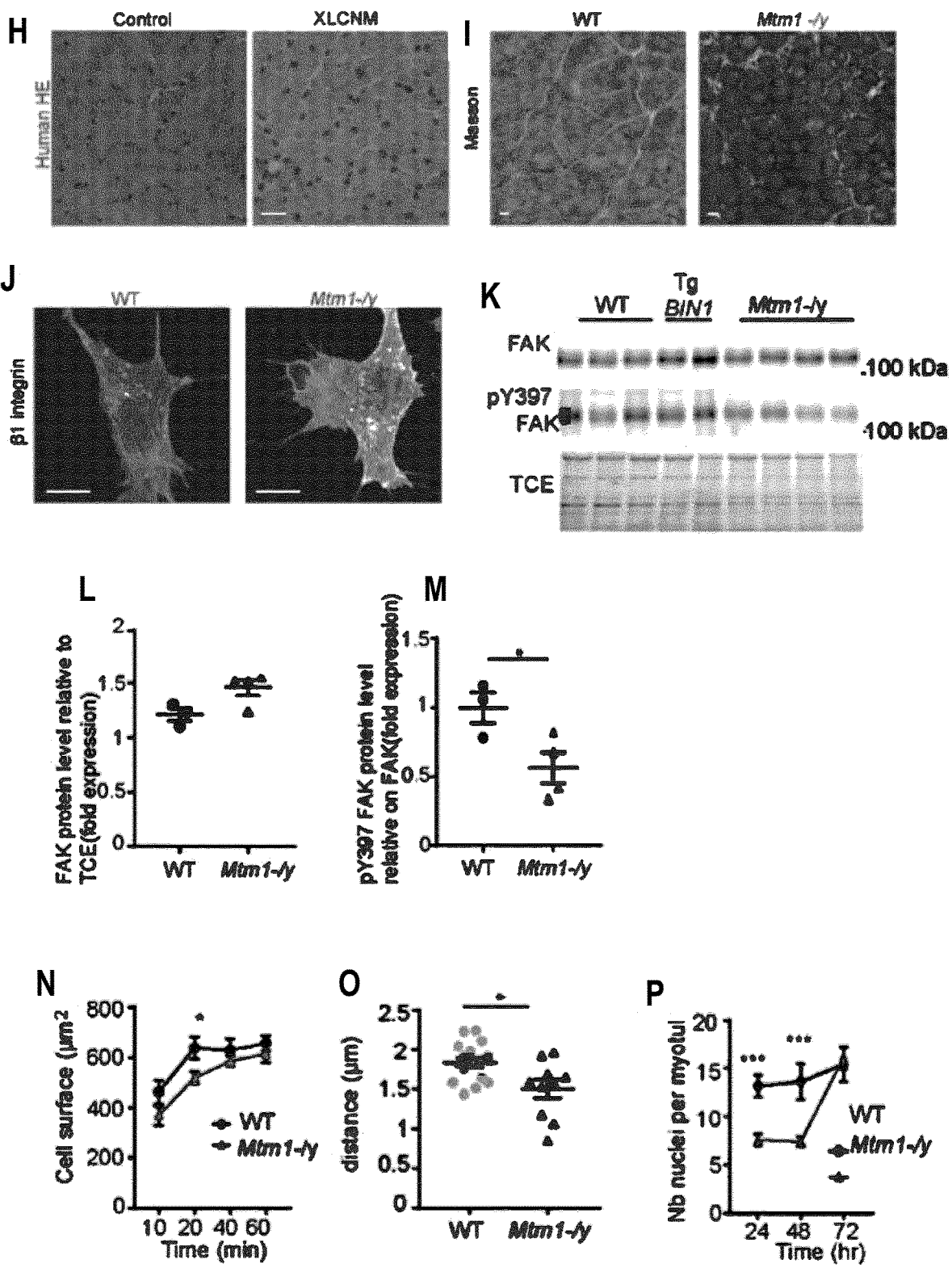

2.9. Mtm1−/y Mice have Defect in Beta1 Integrin Localization, Leading to Focal Adhesion Impairment Adhesion complexes prevent fibers disassembly as skeletal muscle fibers are exposed to continued mechanical stress. In the context of CNM, hypotrophic (smaller) and rounder fibers with increased inter-fiber space are main histological defects in XLCNM patients, suggesting a defect in cell adhesion (FIG. 5H). The Mtm1−/y mouse faithfully recapitulates these hallmarks (FIG. 2A). To better understand if these Mtm1−/y defects were correlated with a defect in skeletal muscle adhesion, transverse TA sections of WT and Mtm1−/y TA muscle were stained for Dystrophin, a protein well-known for providing a structural link between the muscle cytoskeleton and extracellular matrix to maintain muscle integrity, mutations of said protein being notably responsible for the Duchenne and Becker muscular dystrophies (FIG. 5A). Hexagonal fibers of WT skeletal muscle were completely adherent one to the other while Mtm1−/y TA muscle displayed rounder muscle fibers than the WT control as well as an increase in inter-fiber space. To examine whether these fibers shape, and consequently the higher inter-fiber space, corresponded to an increase of extracellular matrix and a disorganization of complexes involved in fiber adhesion, TA transverse sections of WT and Mtm1−/y mice were next stained for two well-known components of the extracellular matrix in skeletal muscle: Collagen and Laminin. Mtm1−/y TA muscle section presented an increased inter-fiber space occupied by Laminin and Collagen IV compared to WT (FIGS. 5C-5D, 5I). Laminin protein level was higher in Mtm1−/y than in WT mice (FIG. 6H).

Proteins from the extracellular matrix, such as Laminin, are known to connect to proteins involved in focal adhesion, including integrins and adaptor proteins such as Vinculin (FIG. 5B). As Mtm1−/y mice had abnormal fiber shape and an increase in extracellular matrix in TA, it was checked whether the localization of proteins involved in cell adhesion were abnormal. In WT, integrins localized at the sarcolemma, specifically at the costamere in skeletal muscle (FIG. 5F). Surprisingly, Mtm1−/y mice exhibited internalized Beta1 Integrin (FIG. 5E), Alpha7 Integrin (data not shown), and Vinculin (FIG. 5E). In other words, Alpha7 Integrin aggregated in the center of some fibers without following the same pattern as Beta1 Integrin, while Vinculin staining displayed an abnormal pattern similar to the one of Beta1 Integrin, inside the fibers in Mtm1−/y mice. This phenotype correlated with an increase in protein level for Beta1 Integrin (FIG. 6E), not due to an increase in transcription (data not shown). As illustrated on FIG. 5B, Beta1 Integrin forms heterodimers with Alpha7 Integrin on the plasma membrane of TA muscle fibers and binds to Talin and Vinculin.

Previous studies indicated that Beta1 Integrin is going through a recycling process. To investigate in which intracellular compartment Beta1 Integrin accumulates, endosomal markers were labelled on muscle sections: Beta1 Integrin colocalized with the early endosome marker EEA1 in Mtm1−/y TA (FIG. 5F). EEA1-positive endosomes also accumulated inside the myofibers only in Mtm1−/y (compared to WT). Additionally, a higher level of Beta1 integrin in Mtm1−/y TA total muscle lysate was detected by Western Blot compared to WT. Overall, these results highlight that Beta1 Integrin abnormally accumulates at early endosomes in Mtm1−/y muscles, indicating a defect Beta1 integrin turnover that may induce the abnormality in fiber shape and the increase in inter-fiber space. To further decipher the mechanism linked to defects in the focal adhesion pathway, the activation of the focal adhesion kinase (FAK), a downstream effector of Beta1 integrin, was measured. The activation of the focal adhesion complex is known to lead to the auto-phosphorylation of FAK on Tyrosine 397. Mtm1−/y muscles showed a decreased auto-phosphorylation of FAK, confirming that activation of the focal adhesion pathway was altered (FIGS. 5K-5M).

To analyze the functional impact of focal adhesion defect observed in skeletal muscle, experiments on primary myoblasts were conducted. Mtm1−/y myoblasts displayed larger Beta1 integrin vesicles than WT myoblasts (FIG. 5J), confirming the accumulation of Beta1 integrin observed in adult skeletal muscle (FIG. 5F). Cell adhesion was checked by letting WT and Mtm1−/y myoblasts adhere for 10, 20, 40 min on laminin coated dishes. The surface area of Mtm1−/y myoblasts was lower than for WT cells at 20 minutes (FIG. 5N). As studies showed that defect in Beta1 Integrin localization affected cell migration, a migration assay was performed with WT and Mtm1−/y myoblasts plated on laminin-coated dishes. A significant reduction of migrating distance was observed in Mtm1−/y myoblast compared to WT (FIG. 5O). Finally, the ability of myoblasts to fuse was followed over time on matrigel-coated dishes. A significant defect of myoblast fusion was identified at 24 and 48 hours after differentiation in Mtm1−/y cells (FIG. 5P). Overall, these results showed that Mtm1−/y myoblasts have defects in cell adhesion, migration and fusion that correlate to a defect in β1 integrin localization and turnover in muscle.

2.10. BIN1 Overexpression Rescues Beta1 Integrin, and Hence Focal Adhesion Defects, in Mtm1−/y Mice Mtm1−/y mice exhibited a defect on Beta1 Integrin protein localization indicating that it might be involved in Beta1 Integrin organization. It was thus analyzed whether BIN1 overexpression could rescue the abnormalities in extracellular matrix and focal adhesion.

Firstly, the TA muscle section of Mtm1−/y Tg BIN1 mice showed a normalization of inter fiber space (reduction observed) and consequently reduced Collagen and Laminin accumulation between fibers (FIGS. 6A-6B and 6G), in addition to a rescue in fiber size and shape (FIG. 2A). It was also found that the laminin levels increased in the Mtm1−/y mice were normalized upon BIN1 increased expression (FIG. 6H). Additionally, muscle immunostaining and western-blotting showed that Mtm1−/y Tg BIN1 mice exhibited reduced intracellular accumulation and normalized total level of Beta1 Integrin (FIGS. 6C-6D). Further investigations of the focal adhesion pathway showed that Vinculin localization, altered in the Mtm1−/y mice, were rescued in Mtm1−/y TgBIN1 mice. Similar normalization of Beta1 Integrin localization in Mtm1−/y muscle was observed upon AAV-BIN1 systemic injection after birth (FIG. 6D), showing this rescue was not dependent on the methodology used for BIN1 expression. To sum up, thanks to the overexpression of BIN1 in Mtm1−/y mice, the recycling pathway of beta1 integrin was normalized.

3. Conclusion

This study reports a genetic and functional link between MTM1 and BIN1 in skeletal muscle. Increased expression of BIN1 by genetic cross or viral delivery after birth prolongs the lifespan of Mtm1−/y mice and rescued the muscle force and the main histological hallmarks of centronuclear myopathy. In the Mtm1−/y mice, defects in integrin turnover and focal adhesion functions correlated with myofiber hypotrophy and abnormal shape, and these phenotypes were rescued upon BIN1 overexpression.

Loss-of-function mutations in BIN1 and MTM1 can cause different forms of CNM; however, their genetic interplay was not elucidated to this day. The present study shows that an increased expression of human BIN1, either by transgenesis or via AAV-mediated transduction, rescued the lifespan, the motor defects, most of the histological and ultrastructural muscle defects, as well as the molecular alterations linked to MTM1 loss. These results thus demonstrate that increased BIN1 compensates for the lack of MTM1, suggesting that MTM1 and BIN1 share a common pathway where MTM1 is a positive regulator of BIN1. In a previous study, a decreased expression of DNM2, a third protein mutated in CNM, was shown to rescue both the CNM phenotypes due to MTM1 or BIN1 loss, supporting that MTM1 and BIN1 are negative regulators of DNM2. Taken together with the present data, a CNM pathway could now be defined where MTM1 would activate BIN1 that in turn inhibits DNM2.

Interestingly, BIN1 protein expression level almost doubled (1.9-fold increase) in the muscle of Mtm1−/y mice at 8 weeks (advanced disease stage), while said level was normal level at 5 weeks (FIGS. 1E and 3H). This observation suggests a potential compensatory mechanism that is insufficient for reaching a rescue, but this rescue can be obtained by increasing BIN1 exogenous expression by about 3.5-fold for example via transgenesis or AAV injection (FIGS. 1E and 4L).

Here, BIN1 was identified as a modifier gene for MTM1-related CNM, and thus as a novel therapeutic for said disease, in particular for treating XLCNM. We thus propose herein a "cross-therapy" concept, where modulation of a CNM gene (BIN1) rescues the loss of another CNM gene (MTM1) to treat a MTM1-related myopathy, in particular XLCNM.

Indeed, BIN1 expression was shown to rescue the postnatal muscle maintenance defects linked to MTM1 loss. Following the positive proof-of-concept based on a transgenesis approach, AAV delivery of human BIN1 was performed after birth of Mtm1−/y mice to validate a translational approach. BIN1 was first overexpressed intramuscularly and then through a systemic delivery: both strategies were sufficient to rescue muscle force and myofiber structural defects. In addition, the systemic injection of AAV-BIN1 greatly prolonged the lifespan of the treated mice. Of note, AAV injection at 3 weeks, after the start of the disease, was shown to be sufficient to provide a rescue, suggesting that treating patients affected at birth may provide a benefit. It must further be noted that, the present study relied on an AAV9 vector to deliver a human BIN1 transgene: since this AAV serotype is already used in clinical trials, preclinical development could be started immediately. Moreover, AAV-mediated MTM1 gene therapy was previously shown to be effective in animal models of XLCNM and is currently assessed in clinical trials. Hence, using an AAV-BIN1 strategy should not generate an immune response to the protein as BIN1 is already present in patients, in contrast to an AAV-MTM1 strategy where patients are exposed to MTM1 for the first time. Furthermore, this approach may avoid potential secondary effects of the DNM2 reduction strategy.

Small rounded fibers and increased inter-fiber space are main histological hallmarks in patients for the diagnosis of XLCNM, and suggest a defect of adhesion to the extracellular matrix. Beta1 integrin is the major integrin molecule of skeletal muscle and links the extracellular matrix with the intracellular cytoskeleton and the sarcomeres at focal adhesions termed costameres. Focal adhesions integrity is indeed important for muscle as they mediate mechano-transduction and are a platform for intracellular signaling. Alteration of beta1 integrin levels and localization in muscle was seen here in 5w- and 8w-old Mtm1−/y mice, together with increased collagen and inter-fiber space. Of note, correct sarcomere alignment and integrity depends on costameres. Indeed, myofibril formation can be inhibited by antagonizing integrin dimers alone, suggesting integrin-ECM interaction is important for correct sarcomere formation during muscle development. Sarcomeres are greatly altered in XLCNM and Mtm1−/y muscles, which probably contributes to the severe muscle weakness. In addition, a recent report proposed that integrins regulate peripheral nuclear positioning in myofibers differentiated in vitro, suggesting that integrin defects may also mediates the centralization of nuclei in CNM. Importantly, all these defects were rescued herein by overexpressing BIN1, supporting the fact that defects in the focal adhesion pathway is an important cause of the disease. MTM1 and BIN1 thus appear as important regulators of focal adhesion. Interestingly, mice that lack Beta1 integrin specifically in skeletal muscle had reduced muscle mass and alteration of sarcomere ultrastructure, and died at birth with noninflated lungs: such phenotypes are typical from XLCNM patients. Also, heterozygous mutations in α7 integrin have been shown to cause muscular dystrophy. Altogether, this supports the rationale that defects in the functions of focal adhesion is an important component of the mechanism leading to the MTM1-related myopathy.

Both MTM1 and BIN1 are involved in membrane remodeling and recycling in cells, and we observed that Beta1 integrin is blocked in EEA1-positive endosomes in Mtm1−/y muscles. This defect maybe due to the fact that MTM1 is implicated in the conversion of early to late or recycling endosomes. This function appears conserved in evolution as Ribeiro et al. found that the *drosophila* ortholog of MTM1 was necessary for integrin turnover (Ribeiro et al., PLoS Genet 7, e1001295 (2011)). The present study highlights for the first time that integrin downstream effectors, such as vinculin and FAK, were altered in Mtm1−/y muscles, supporting the integrin trafficking defects lead to alteration of focal adhesion signaling. Subsequently, alteration of focal adhesion caused a defect in adhesion, migration and fusion of myoblasts lacking MTM1, leading to a decrease in myoblast to myotube fusion index that is reminiscent of the myofibers hypotrophy typically seen in patient muscles.

Overall, this study underlines a key role for MTM1 and BIN1 in the regulation of integrin trafficking and activation of focal adhesion in skeletal muscle, and points to the defect in these mechanisms as an important cause of XLCNM that can be efficiently rescued by increasing BIN1 expression, for example through gene viral delivery.

SEQUENCE LISTING

<160> NUMBER OF SEQ ID NOS: 35

<210> SEQ ID NO 1
<211> LENGTH: 1782
<212> TYPE: DNA
<213> ORGANISM: Homo sapiens

<400> SEQUENCE: 1

```
atggcagaga tgggcagtaa aggggtgacg gcgggaaaga tcgccagcaa cgtgcagaag      60
aagctcaccc gcgcgcagga gaaggttctc cagaagctgg ggaaggcaga tgagaccaag     120
gatgagcagt ttgagcagtg cgtccagaat ttcaacaagc agctgacgga gggcacccgg     180
ctgcagaagg atctccggac ctacctggcc tccgtcaaag ccatgcacga ggcttccaag     240
aagctgaatg agtgtctgca ggaggtgtat gagcccgatt ggcccggcag ggatgaggca     300
aacaagatcg cagagaacaa cgacctgctg tggatggatt accaccagaa gctggtggac     360
caggcgctgc tgaccatgga cacgtacctg ggccagttcc ccgacatcaa gtcacgcatt     420
gccaagcggg ggcgcaagct ggtggactac gacagtgccc ggcaccacta cgagtccctt     480
caaactgcca aaaagaagga tgaagccaaa attgccaagc ctgtctcgct gcttgagaaa     540 gccgccccc agtggtgcca aggcaaactg caggctcatc tcgtagctca aactaacctg     600
ctccgaaatc aggccgagga ggagctcatc aaagcccaga aggtgtttga ggagatgaat     660
gtggatctgc aggaggagct gccgtccctg tggaacagcc gcgtaggttt ctacgtcaac     720
acgttccaga gcatcgcggg cctggaggaa aacttccaca aggagatgag caagctcaac     780
cagaacctca tgatgtgct ggtcggcctg gagaagcaac acgggagcaa cccttcacg      840 gtcaaggccc agcccagtga caacgcgcct gcaaaaggga caagagccc ttcgcctcca      900 gatggctccc ctgccgccac ccccgagatc agagtcaacc acgagccaga gccggccggc      960
ggggccacgc ccgggccac cctccccaag tccccatctc agctccggaa aggcccacca     1020
gtccctccgc ctcccaaaca cacccgtcc aaggaagtca agcaggagca gatcctcagc     1080
ctgtttgagg acacgtttgt ccctgagatc agcgtgacca ccccctccca gtttgaggcc     1140
ccggggcctt tctcggagca ggccagtctg ctggacctgg actttgaccc cctcccgccc     1200
gtgacgagcc ctgtgaaggc acccacgccc tctggtcagt caattccatg ggacctctgg     1260
gagcccacag agagtccagc cggcagcctg ccttccgggg agcccagcgc tgccgagggc     1320
acctttgctg tgtcctggcc cagccagacg gccgagccgg ggcctgccca accagcagag     1380
gcctcggagg tggcgggtgg gacccaacct gcggctggag cccaggagcc aggggagacg     1440
gcggcaagtg aagcagcctc cagctctctt cctgctgtcg tggtggagac cttcccagca     1500
```

```
actgtgaatg gcaccgtgga gggcggcagt ggggccgggc gcttggacct gcccccaggt    1560
ttcatgttca aggtacaggc ccagcacgac tacacggcca ctgacacaga cgagctgcag    1620
ctcaaggctg gtgatgtggt gctggtgatc cccttccaga accctgaaga gcaggatgaa    1680
ggctggctca tgggcgtgaa ggagagcgac tggaaccagc acaaggagct ggagaagtgc    1740
cgtggcgtct tccccgagaa cttcactgag agggtcccat ga                      1782
```

<210> SEQ ID NO 2
<211> LENGTH: 593
<212> TYPE: PRT
<213> ORGANISM: Homo sapiens

<400> SEQUENCE: 2

```
Met Ala Glu Met Gly Ser Lys Gly Val Thr Ala Gly Lys Ile Ala Ser
1               5                   10                  15

Asn Val Gln Lys Lys Leu Thr Arg Ala Gln Glu Lys Val Leu Gln Lys
                20                  25                  30

Leu Gly Lys Ala Asp Glu Thr Lys Asp Glu Gln Phe Glu Gln Cys Val
            35                  40                  45

Gln Asn Phe Asn Lys Gln Leu Thr Glu Gly Thr Arg Leu Gln Lys Asp
        50                  55                  60

Leu Arg Thr Tyr Leu Ala Ser Val Lys Ala Met His Glu Ala Ser Lys
65                  70                  75                  80

Lys Leu Asn Glu Cys Leu Gln Glu Val Tyr Glu Pro Asp Trp Pro Gly
                85                  90                  95

Arg Asp Glu Ala Asn Lys Ile Ala Glu Asn Asn Asp Leu Leu Trp Met
                100                 105                 110

Asp Tyr His Gln Lys Leu Val Asp Gln Ala Leu Leu Thr Met Asp Thr
            115                 120                 125

Tyr Leu Gly Gln Phe Pro Asp Ile Lys Ser Arg Ile Ala Lys Arg Gly
        130                 135                 140

Arg Lys Leu Val Asp Tyr Asp Ser Ala Arg His His Tyr Glu Ser Leu
145                 150                 155                 160

Gln Thr Ala Lys Lys Lys Asp Glu Ala Lys Ile Ala Lys Pro Val Ser
                165                 170                 175

Leu Leu Glu Lys Ala Ala Pro Gln Trp Cys Gln Gly Lys Leu Gln Ala
            180                 185                 190

His Leu Val Ala Gln Thr Asn Leu Leu Arg Asn Gln Ala Glu Glu Glu
        195                 200                 205

Leu Ile Lys Ala Gln Lys Val Phe Glu Glu Met Asn Val Asp Leu Gln
    210                 215                 220

Glu Glu Leu Pro Ser Leu Trp Asn Ser Arg Val Gly Phe Tyr Val Asn
225                 230                 235                 240

Thr Phe Gln Ser Ile Ala Gly Leu Glu Glu Asn Phe His Lys Glu Met
                245                 250                 255

Ser Lys Leu Asn Gln Asn Leu Asn Asp Val Leu Val Gly Leu Glu Lys
            260                 265                 270

Gln His Gly Ser Asn Thr Phe Thr Val Lys Ala Gln Pro Ser Asp Asn
        275                 280                 285

Ala Pro Ala Lys Gly Asn Lys Ser Pro Ser Pro Asp Gly Ser Pro
    290                 295                 300

Ala Ala Thr Pro Glu Ile Arg Val Asn His Glu Pro Glu Pro Ala Gly
305                 310                 315                 320

Gly Ala Thr Pro Gly Ala Thr Leu Pro Lys Ser Pro Ser Gln Leu Arg
```

```
                    325                 330                 335
Lys Gly Pro Pro Val Pro Pro Pro Lys His Thr Pro Ser Lys Glu
            340                 345                 350
Val Lys Gln Glu Gln Ile Leu Ser Leu Phe Glu Asp Thr Phe Val Pro
            355                 360                 365
Glu Ile Ser Val Thr Thr Pro Ser Gln Phe Glu Ala Pro Gly Pro Phe
        370                 375                 380
Ser Glu Gln Ala Ser Leu Leu Asp Leu Asp Phe Asp Pro Leu Pro Pro
385                 390                 395                 400
Val Thr Ser Pro Val Lys Ala Pro Thr Pro Ser Gly Gln Ser Ile Pro
                405                 410                 415
Trp Asp Leu Trp Glu Pro Thr Glu Ser Pro Ala Gly Ser Leu Pro Ser
            420                 425                 430
Gly Glu Pro Ser Ala Ala Glu Gly Thr Phe Ala Val Ser Trp Pro Ser
            435                 440                 445
Gln Thr Ala Glu Pro Gly Pro Ala Gln Pro Ala Glu Ala Ser Glu Val
        450                 455                 460
Ala Gly Gly Thr Gln Pro Ala Ala Gly Ala Gln Glu Pro Gly Glu Thr
465                 470                 475                 480
Ala Ala Ser Glu Ala Ala Ser Ser Ser Leu Pro Ala Val Val Val Glu
                485                 490                 495
Thr Phe Pro Ala Thr Val Asn Gly Thr Val Glu Gly Gly Ser Gly Ala
            500                 505                 510
Gly Arg Leu Asp Leu Pro Pro Gly Phe Met Phe Lys Val Gln Ala Gln
            515                 520                 525
His Asp Tyr Thr Ala Thr Asp Thr Asp Glu Leu Gln Leu Lys Ala Gly
        530                 535                 540
Asp Val Val Leu Val Ile Pro Phe Gln Asn Pro Glu Glu Gln Asp Glu
545                 550                 555                 560
Gly Trp Leu Met Gly Val Lys Glu Ser Asp Trp Asn Gln His Lys Glu
                565                 570                 575
Leu Glu Lys Cys Arg Gly Val Phe Pro Glu Asn Phe Thr Glu Arg Val
            580                 585                 590
Pro

<210> SEQ ID NO 3
<211> LENGTH: 84
<212> TYPE: DNA
<213> ORGANISM: Homo sapiens

<400> SEQUENCE: 3
atggcagaga tgggcagtaa aggggtgacg gcgggaaaga tcgccagcaa cgtgcagaag      60
aagctcaccc gcgcgcagga gaag                                            84

<210> SEQ ID NO 4
<211> LENGTH: 80
<212> TYPE: DNA
<213> ORGANISM: Homo sapiens

<400> SEQUENCE: 4
gttctccaga agctggggaa ggcagatgag accaaggatg agcagtttga gcagtgcgtc      60
cagaatttca caagcagct                                                  80

<210> SEQ ID NO 5
<211> LENGTH: 56
```

```
<212> TYPE: DNA
<213> ORGANISM: Homo sapiens

<400> SEQUENCE: 5
gacggagggc acccggctgc agaaggatct ccggacctac ctggcctccg tcaaag        56

<210> SEQ ID NO 6
<211> LENGTH: 95
<212> TYPE: DNA
<213> ORGANISM: Homo sapiens

<400> SEQUENCE: 6
ccatgcacga ggcttccaag aagctgaatg agtgtctgca ggaggtgtat gagcccgatt    60
ggcccggcag ggatgaggca acaagatcg cagag                                95

<210> SEQ ID NO 7
<211> LENGTH: 96
<212> TYPE: DNA
<213> ORGANISM: Homo sapiens

<400> SEQUENCE: 7
aacaacgacc tgctgtggat ggattaccac cagaagctgg tggaccaggc gctgctgacc    60
atggacacgt acctgggcca gttccccgac atcaag                              96

<210> SEQ ID NO 8
<211> LENGTH: 108
<212> TYPE: DNA
<213> ORGANISM: Homo sapiens

<400> SEQUENCE: 8
tcacgcattg ccaagcgggg gcgcaagctg gtggactacg acagtgcccg gcaccactac    60
gagtcccttc aaactgccaa aagaaggat gaagccaaaa ttgccaag                 108

<210> SEQ ID NO 9
<211> LENGTH: 93
<212> TYPE: DNA
<213> ORGANISM: Homo sapiens

<400> SEQUENCE: 9
cctgtctcgc tgcttgagaa agccgccccc cagtggtgcc aaggcaaact gcaggctcat    60
ctcgtagctc aaactaacct gctccgaaat cag                                 93

<210> SEQ ID NO 10
<211> LENGTH: 86
<212> TYPE: DNA
<213> ORGANISM: Homo sapiens

<400> SEQUENCE: 10
gccgaggagg agctcatcaa agcccagaag gtgtttgagg agatgaatgt ggatctgcag    60
gaggagctgc cgtccctgtg aacag                                          86

<210> SEQ ID NO 11
<211> LENGTH: 76
<212> TYPE: DNA
<213> ORGANISM: Homo sapiens

<400> SEQUENCE: 11
ccgcgtaggt ttctacgtca acacgttcca gagcatcgcg ggcctggagg aaaacttcca    60
caaggagatg agcaag                                                    76
```

<210> SEQ ID NO 12
<211> LENGTH: 83
<212> TYPE: DNA
<213> ORGANISM: Homo sapiens

<400> SEQUENCE: 12
ctcaaccaga acctcaatga tgtgctggtc ggcctggaga agcaacacgg gagcaacacc     60
ttcacggtca aggcccagcc cag                                            83

<210> SEQ ID NO 13
<211> LENGTH: 45
<212> TYPE: DNA
<213> ORGANISM: Homo sapiens

<400> SEQUENCE: 13
aaagaaaagt aaactgttttt cgcggctgcg cagaaagaag aacag                   45

<210> SEQ ID NO 14
<211> LENGTH: 145
<212> TYPE: DNA
<213> ORGANISM: Homo sapiens

<400> SEQUENCE: 14
tgacaacgcg cctgcaaaag ggaacaagag cccttcgcct ccagatggct ccctgccgc     60 cacccccgag atcagagtca accacgagcc agagccggcc ggcggggcca cgcccggggc   120
caccctcccc aagtccccat ctcag                                         145

<210> SEQ ID NO 15
<211> LENGTH: 108
<212> TYPE: DNA
<213> ORGANISM: Homo sapiens

<400> SEQUENCE: 15
tttgaggccc cggggccttt ctcggagcag gccagtctgc tggacctgga ctttgacccc    60
ctcccgcccg tgacgagccc tgtgaaggca cccacgccct ctggtcag                108

<210> SEQ ID NO 16
<211> LENGTH: 24
<212> TYPE: DNA
<213> ORGANISM: Homo sapiens

<400> SEQUENCE: 16
tcaattccat gggacctctg ggag                                          24

<210> SEQ ID NO 17
<211> LENGTH: 108
<212> TYPE: DNA
<213> ORGANISM: Homo sapiens

<400> SEQUENCE: 17
cccacagaga gtccagccgg cagcctgcct tccggggagc ccagcgctgc cgagggcacc    60
tttgctgtgt cctggcccag ccagacggcc gagccggggc ctgcccaa               108

<210> SEQ ID NO 18
<211> LENGTH: 90
<212> TYPE: DNA
<213> ORGANISM: Homo sapiens

<400> SEQUENCE: 18
ccagcagagg cctcggaggt ggcgggtggg acccaacctg cggctggagc ccaggagcca    60

```
ggggagacgg cggcaagtga agcagcctcc                                          90

<210> SEQ ID NO 19
<211> LENGTH: 90
<212> TYPE: DNA
<213> ORGANISM: Homo sapiens

<400> SEQUENCE: 19
ccagcagagg cctcggaggt ggcgggtggg acccaacctg cggctggagc ccaggagcca        60
ggggagacgg cggcaagtga agcagcctcc                                          90

<210> SEQ ID NO 20
<211> LENGTH: 111
<212> TYPE: DNA
<213> ORGANISM: Homo sapiens

<400> SEQUENCE: 20
agctctcttc ctgctgtcgt ggtggagacc ttcccagcaa ctgtgaatgg caccgtggag        60
ggcggcagtg gggccgggcg cttggacctg cccccaggtt tcatgttcaa g                111

<210> SEQ ID NO 21
<211> LENGTH: 102
<212> TYPE: DNA
<213> ORGANISM: Homo sapiens

<400> SEQUENCE: 21
gtacaggccc agcacgacta cacggccact gacacagacg agctgcagct caaggctggt        60
gatgtggtgc tggtgatccc cttccagaac cctgaagagc ag                          102

<210> SEQ ID NO 22
<211> LENGTH: 108
<212> TYPE: DNA
<213> ORGANISM: Homo sapiens

<400> SEQUENCE: 22
gatgaaggct ggctcatggg cgtgaaggag agcgactgga accagcacaa ggagctggag        60
aagtgccgtg gcgtcttccc cgagaacttc actgagaggg tcccatga                    108

<210> SEQ ID NO 23
<211> LENGTH: 812
<212> TYPE: DNA
<213> ORGANISM: artificial
<220> FEATURE:
<223> OTHER INFORMATION: artificial cDNA sequence with exons 1 to 6 and
      8 to 11

<400> SEQUENCE: 23
atggcagaga tgggcagtaa aggggtgacg gcgggaaaga tcgccagcaa cgtgcagaag        60
aagctcaccc gcgcgcagga gaaggttctc cagaagctgg ggaaggcaga tgagaccaag       120
gatgagcagt ttgagcagtg cgtccagaat ttcaacaagc agctgacgga gggcacccgg       180
ctgcagaagg atctccggac ctacctggcc tccgtcaaag ccatgcacga ggcttccaag       240
aagctgaatg agtgtctgca ggaggtgtat gagcccgatt ggcccggcag ggatgaggca       300
aacaagatcg cagagaacaa cgacctgctg tggatggatt accaccagaa gctggtggac       360
caggcgctgc tgaccatgga cacgtacctg ggccagttcc ccgacatcaa gtcacgcatt       420
gccaagcggg ggcgcaagct ggtggactac gacagtgccc ggcaccacta cgagtccctt       480
caaactgcca aaagaagga tgaagccaaa attgccaagg ccgaggagga gctcatcaaa       540
```

```
gcccagaagg tgtttgagga gatgaatgtg gatctgcagg aggagctgcc gtccctgtgg      600
aacagccgcg taggtttcta cgtcaacacg ttccagagca tcgcgggcct ggaggaaaac      660
ttccacaagg agatgagcaa gctcaaccag aacctcaatg atgtgctggt cggcctggag      720
aagcaacacg ggagcaacac cttcacggtc aaggcccagc ccagaaagaa aagtaaactg      780
ttttcgcggc tgcgcagaaa gaagaacagt ga                                    812
```

<210> SEQ ID NO 24
<211> LENGTH: 270
<212> TYPE: PRT
<213> ORGANISM: artificial
<220> FEATURE:
<223> OTHER INFORMATION: aminoacid sequence corresponding to artificial
      cDNA sequence with exons 1 to 6 and 8 to 11

<400> SEQUENCE: 24

```
Met Ala Glu Met Gly Ser Lys Gly Val Thr Ala Gly Lys Ile Ala Ser
1               5                   10                  15

Asn Val Gln Lys Lys Leu Thr Arg Ala Gln Glu Lys Val Leu Gln Lys
                20                  25                  30

Leu Gly Lys Ala Asp Glu Thr Lys Asp Glu Gln Phe Glu Gln Cys Val
            35                  40                  45

Gln Asn Phe Asn Lys Gln Leu Thr Glu Gly Thr Arg Leu Gln Lys Asp
        50                  55                  60

Leu Arg Thr Tyr Leu Ala Ser Val Lys Ala Met His Glu Ala Ser Lys
65                  70                  75                  80

Lys Leu Asn Glu Cys Leu Gln Glu Val Tyr Glu Pro Asp Trp Pro Gly
                85                  90                  95

Arg Asp Glu Ala Asn Lys Ile Ala Glu Asn Asn Asp Leu Leu Trp Met
            100                 105                 110

Asp Tyr His Gln Lys Leu Val Asp Gln Ala Leu Leu Thr Met Asp Thr
        115                 120                 125

Tyr Leu Gly Gln Phe Pro Asp Ile Lys Ser Arg Ile Ala Lys Arg Gly
130                 135                 140

Arg Lys Leu Val Asp Tyr Asp Ser Ala Arg His His Tyr Glu Ser Leu
145                 150                 155                 160

Gln Thr Ala Lys Lys Lys Asp Glu Ala Lys Ile Ala Lys Ala Glu Glu
                165                 170                 175

Glu Leu Ile Lys Ala Gln Lys Val Phe Glu Glu Met Asn Val Asp Leu
            180                 185                 190

Gln Glu Glu Leu Pro Ser Leu Trp Asn Ser Arg Val Gly Phe Tyr Val
        195                 200                 205

Asn Thr Phe Gln Ser Ile Ala Gly Leu Glu Glu Asn Phe His Lys Glu
210                 215                 220

Met Ser Lys Leu Asn Gln Asn Leu Asn Asp Val Leu Val Gly Leu Glu
225                 230                 235                 240

Lys Gln His Gly Ser Asn Thr Phe Thr Val Lys Ala Gln Pro Arg Lys
                245                 250                 255

Lys Ser Lys Leu Phe Ser Arg Leu Arg Arg Lys Lys Asn Ser
            260                 265                 270
```

<210> SEQ ID NO 25
<211> LENGTH: 1320
<212> TYPE: DNA
<213> ORGANISM: Homo sapiens

<400> SEQUENCE: 25

```
atggcagaga tgggcagtaa aggggtgacg gcgggaaaga tcgccagcaa cgtgcagaag      60
aagctcaccc gcgcgcagga gaaggttctc cagaagctgg ggaaggcaga tgagaccaag     120
gatgagcagt ttgagcagtg cgtccagaat ttcaacaagc agctgacgga gggcacccgg     180
ctgcagaagg atctccggac ctacctggcc tccgtcaaag ccatgcacga ggcttccaag     240
aagctgaatg agtgtctgca ggaggtgtat gagcccgatt ggcccggcag ggatgaggca     300
aacaagatcg cagagaacaa cgacctgctg tggatggatt accaccagaa gctggtggac     360
caggcgctgc tgaccatgga cacgtacctg ggccagttcc ccgacatcaa gtcacgcatt     420
gccaagcggg ggcgcaagct ggtggactac gacagtgccc ggcaccacta cgagtcccct     480
caaactgcca aaagaagga tgaagccaaa attgccaagg ccgaggagga gctcatcaaa     540
gcccagaagg tgtttgagga tgaatgtg atctgcagg aggagctgcc gtccctgtgg         600
aacagccgcg taggtttcta cgtcaacacg ttccagagca tcgcgggcct ggaggaaaac     660
ttccacaagg agatgagcaa gctcaaccag aacctcaatg atgtgctggt cggcctggag     720
aagcaacacg ggagcaacac cttcacggtc aaggcccagc ccagtgacaa cgcgcctgca     780
aaagggaaca agagcccttc gcctccagat ggctcccctg ccgccacccc cgagatcaga     840
gtcaaccacg agccagagcc ggccggcggg gccacgcccg ggccaccct ccccaagtcc       900
ccatctcagc cagcagaggc ctcggaggtg gcgggtggga cccaacctgc ggctggagcc     960
caggagccag gggagacggc ggcaagtgaa gcagcctcca gctctcttcc tgctgtcgtg    1020
gtggagacct tcccagcaac tgtgaatggc accgtggagg cggcagtgg ggccgggcgc      1080
ttggacctgc ccccaggttt catgttcaag gtacaggccc agcacgacta cacggccact    1140
gacacagacg agctgcagct caaggctggt gatgtggtgc tggtgatccc cttccagaac    1200
cctgaagagc aggatgaagg ctggctcatg ggcgtgaagg agagcgactg gaaccagcac    1260
aaggagctgg agaagtgccg tggcgtcttc cccgagaact tcactgagag ggtcccatga    1320
```

<210> SEQ ID NO 26
<211> LENGTH: 439
<212> TYPE: PRT
<213> ORGANISM: Homo sapiens

<400> SEQUENCE: 26

```
Met Ala Glu Met Gly Ser Lys Gly Val Thr Ala Gly Lys Ile Ala Ser
1               5                   10                  15

Asn Val Gln Lys Lys Leu Thr Arg Ala Gln Glu Lys Val Leu Gln Lys
            20                  25                  30

Leu Gly Lys Ala Asp Glu Thr Lys Asp Glu Gln Phe Glu Gln Cys Val
        35                  40                  45

Gln Asn Phe Asn Lys Gln Leu Thr Glu Gly Thr Arg Leu Gln Lys Asp
    50                  55                  60

Leu Arg Thr Tyr Leu Ala Ser Val Lys Ala Met His Glu Ala Ser Lys
65                  70                  75                  80

Lys Leu Asn Glu Cys Leu Gln Glu Val Tyr Glu Pro Asp Trp Pro Gly
                85                  90                  95

Arg Asp Glu Ala Asn Lys Ile Ala Glu Asn Asn Asp Leu Leu Trp Met
            100                 105                 110

Asp Tyr His Gln Lys Leu Val Asp Gln Ala Leu Leu Thr Met Asp Thr
        115                 120                 125

Tyr Leu Gly Gln Phe Pro Asp Ile Lys Ser Arg Ile Ala Lys Arg Gly
```

```
                130             135             140
Arg Lys Leu Val Asp Tyr Asp Ser Ala Arg His His Tyr Glu Ser Leu
145                 150                 155                 160

Gln Thr Ala Lys Lys Asp Glu Ala Lys Ile Ala Lys Ala Glu Glu
                165                 170                 175

Glu Leu Ile Lys Ala Gln Lys Val Phe Glu Met Asn Val Asp Leu
            180                 185                 190

Gln Glu Glu Leu Pro Ser Leu Trp Asn Ser Arg Val Gly Phe Tyr Val
            195                 200                 205

Asn Thr Phe Gln Ser Ile Ala Gly Leu Glu Glu Asn Phe His Lys Glu
            210                 215                 220

Met Ser Lys Leu Asn Gln Asn Leu Asn Asp Val Leu Val Gly Leu Glu
225                 230                 235                 240

Lys Gln His Gly Ser Asn Thr Phe Thr Val Lys Ala Gln Pro Ser Asp
                245                 250                 255

Asn Ala Pro Ala Lys Gly Asn Lys Ser Pro Ser Pro Asp Gly Ser
            260                 265                 270

Pro Ala Thr Pro Glu Ile Arg Val Asn His Glu Pro Glu Pro Ala
            275                 280                 285

Gly Gly Ala Thr Pro Gly Ala Thr Leu Pro Lys Ser Pro Ser Gln Pro
290                 295                 300

Ala Glu Ala Ser Glu Val Ala Gly Gly Thr Gln Pro Ala Ala Gly Ala
305                 310                 315                 320

Gln Glu Pro Gly Glu Thr Ala Ala Ser Glu Ala Ala Ser Ser Ser Leu
                325                 330                 335

Pro Ala Val Val Val Glu Thr Phe Pro Ala Thr Val Asn Gly Thr Val
            340                 345                 350

Glu Gly Gly Ser Gly Ala Gly Arg Leu Asp Leu Pro Pro Gly Phe Met
            355                 360                 365

Phe Lys Val Gln Ala Gln His Asp Tyr Thr Ala Thr Asp Thr Asp Glu
            370                 375                 380

Leu Gln Leu Lys Ala Gly Asp Val Val Leu Val Ile Pro Phe Gln Asn
385                 390                 395                 400

Pro Glu Glu Gln Asp Glu Gly Trp Leu Met Gly Val Lys Glu Ser Asp
                405                 410                 415

Trp Asn Gln His Lys Glu Leu Glu Lys Cys Arg Gly Val Phe Pro Glu
                420                 425                 430

Asn Phe Thr Glu Arg Val Pro
            435

<210> SEQ ID NO 27
<211> LENGTH: 1275
<212> TYPE: DNA
<213> ORGANISM: Homo sapiens

<400> SEQUENCE: 27
atggcagaga tgggcagtaa agggggtgacg gcgggaaaga tcgccagcaa cgtgcagaag      60
aagctcaccc gcgcgcagga gaaggttctc cagaagctgg ggaaggcaga tgagaccaag     120
gatgagcagt ttgagcagtg cgtccagaat ttcaacaagc agctgacgga gggcacccgg     180
ctgcagaagg atctccggac ctacctggcc tccgtcaaag ccatgcacga ggcttccaag     240
aagctgaatg agtgtctgca ggaggtgtat gagcccgatt ggccCggcag ggatgaggca     300
aacaagatcg cagagaacaa cgacctgctg tggatggatt accaccagaa gctggtggac     360
```

```
caggcgctgc tgaccatgga cacgtacctg gccagttcc ccgacatcaa gtcacgcatt      420
gccaagcggg ggcgcaagct ggtggactac gacagtgccc ggcaccacta cgagtccctt      480
caaactgcca aaagaagga tgaagccaaa attgccaagg ccgaggagga gctcatcaaa      540
gcccagaagg tgtttgagga gatgaatgtg gatctgcagg aggagctgcc gtccctgtgg      600
aacagccgcg taggtttcta cgtcaacacg ttccagagca tcgcgggcct ggaggaaaac      660
ttccacaagg agatgagcaa gctcaaccag aacctcaatg atgtgctggt cggcctggag      720
aagcaacacg ggagcaacac cttcacggtc aaggcccagc ccagaaagaa aagtaaactg      780
ttttcgcggc tgcgcagaaa gaagaacagt gacaacgcgc tgcaaaagg gaacaagagc       840 ccttcgcctc cagatggctc ccctgccgcc accccgaga tcagagtcaa ccacgagcca       900
gagccggccg cgggggccac gcccggggcc accctcccca gtccccatc tcagagctct       960 cttcctgctg tcgtggtgga gaccttccca gcaactgtga atggcaccgt ggagggcggc     1020
agtggggccg ggcgcttgga cctgccccca ggtttcatgt tcaaggtaca ggcccagcac     1080
gactacacgg ccactgacac agacgagctg cagctcaagg ctggtgatgt ggtgctggtg     1140
atccccttcc agaaccctga agagcaggat gaaggctggc tcatgggcgt gaaggagagc     1200
gactggaacc agcacaagga gctggagaag tgccgtggcg tcttccccga gaacttcact     1260
gagagggtcc catga                                                      1275
```

<210> SEQ ID NO 28
<211> LENGTH: 424
<212> TYPE: PRT
<213> ORGANISM: Homo sapiens

<400> SEQUENCE: 28

```
Met Ala Glu Met Gly Ser Lys Gly Val Thr Ala Gly Lys Ile Ala Ser
1               5                   10                  15

Asn Val Gln Lys Lys Leu Thr Arg Ala Gln Glu Lys Val Leu Gln Lys
            20                  25                  30

Leu Gly Lys Ala Asp Glu Thr Lys Asp Glu Gln Phe Glu Gln Cys Val
        35                  40                  45

Gln Asn Phe Asn Lys Gln Leu Thr Glu Gly Thr Arg Leu Gln Lys Asp
    50                  55                  60

Leu Arg Thr Tyr Leu Ala Ser Val Lys Ala Met His Glu Ala Ser Lys
65                  70                  75                  80

Lys Leu Asn Glu Cys Leu Gln Glu Val Tyr Glu Pro Asp Trp Pro Gly
                85                  90                  95

Arg Asp Glu Ala Asn Lys Ile Ala Glu Asn Asn Asp Leu Leu Trp Met
            100                 105                 110

Asp Tyr His Gln Lys Leu Val Asp Gln Ala Leu Leu Thr Met Asp Thr
        115                 120                 125

Tyr Leu Gly Gln Phe Pro Asp Ile Lys Ser Arg Ile Ala Lys Arg Gly
    130                 135                 140

Arg Lys Leu Val Asp Tyr Asp Ser Ala Arg His His Tyr Glu Ser Leu
145                 150                 155                 160

Gln Thr Ala Lys Lys Lys Asp Glu Ala Lys Ile Ala Lys Ala Glu Glu
                165                 170                 175

Glu Leu Ile Lys Ala Gln Lys Val Phe Glu Glu Met Asn Val Asp Leu
            180                 185                 190

Gln Glu Glu Leu Pro Ser Leu Trp Asn Ser Arg Val Gly Phe Tyr Val
        195                 200                 205
```

```
Asn Thr Phe Gln Ser Ile Ala Gly Leu Glu Glu Asn Phe His Lys Glu
    210                 215                 220

Met Ser Lys Leu Asn Gln Asn Leu Asn Asp Val Leu Val Gly Leu Glu
225                 230                 235                 240

Lys Gln His Gly Ser Asn Thr Phe Thr Val Lys Ala Gln Pro Arg Lys
                245                 250                 255

Lys Ser Lys Leu Phe Ser Arg Leu Arg Arg Lys Lys Asn Ser Asp Asn
            260                 265                 270

Ala Pro Ala Lys Gly Asn Lys Ser Pro Ser Pro Asp Gly Ser Pro
        275                 280                 285

Ala Ala Thr Pro Glu Ile Arg Val Asn His Glu Pro Glu Pro Ala Gly
    290                 295                 300

Gly Ala Thr Pro Gly Ala Thr Leu Pro Lys Ser Pro Ser Gln Ser Ser
305                 310                 315                 320

Leu Pro Ala Val Val Val Glu Thr Phe Pro Ala Thr Val Asn Gly Thr
                325                 330                 335

Val Glu Gly Gly Ser Gly Ala Gly Arg Leu Asp Leu Pro Pro Gly Phe
            340                 345                 350

Met Phe Lys Val Gln Ala Gln His Asp Tyr Thr Ala Thr Asp Thr Asp
        355                 360                 365

Glu Leu Gln Leu Lys Ala Gly Asp Val Val Leu Val Ile Pro Phe Gln
    370                 375                 380

Asn Pro Glu Glu Gln Asp Glu Gly Trp Leu Met Gly Val Lys Glu Ser
385                 390                 395                 400

Asp Trp Asn Gln His Lys Glu Leu Glu Lys Cys Arg Gly Val Phe Pro
                405                 410                 415

Glu Asn Phe Thr Glu Arg Val Pro
            420

<210> SEQ ID NO 29
<211> LENGTH: 1365
<212> TYPE: DNA
<213> ORGANISM: Homo sapiens

<400> SEQUENCE: 29
atggcagaga tgggcagtaa aggggtgacg gcgggaaaga tcgccagcaa cgtgcagaag      60
aagctcaccc gcgcgcagga gaaggttctc cagaagctgg ggaaggcaga tgagaccaag     120
gatgagcagt ttgagcagtg cgtccagaat ttcaacaagc agctgacgga gggcacccgg     180
ctgcagaagg atctccggac ctacctggcc tccgtcaaag ccatgcacga ggcttccaag     240
aagctgaatg agtgtctgca ggaggtgtat gagcccgatt ggcccggcag ggatgaggca     300
aacaagatcg cagagaacaa cgacctgctg tggatggatt accaccagaa gctggtggac     360
caggcgctgc tgaccatgga cacgtacctg gccagttccc ccgacatcaa gtcacgcatt     420
gccaagcggg gcgcaagct ggtggactac gacagtgccc ggcaccacta cgagtcccct     480
caaactgcca aaagaagga tgaagccaaa attgccaagg ccgaggagga gctcatcaaa     540
gcccagaagg tgtttgagga tgaatgtgt gatctgcagg aggagctgcc gtccctgtgg     600
aacagccgcg taggtttcta cgtcaacacg ttccagagca tcgcgggcct ggaggaaaac     660
ttccacaagg agatgagcaa gctcaaccag aacctcaatg atgtgctggt cggcctggag     720
aagcaacacg ggagcaacac cttcacggtc aaggcccagc ccagaaagaa agtaaactg     780 ttttcgcggc tgcgcagaaa gaagaacagt gacaacgcgc tgcaaaagg gaacaagagc     840 ccttcgcctc cagatggctc ccctgccgcc acccccgaga tcagagtcaa ccacgagcca     900
```

```
gagccggccg gcggggccac gcccggggcc accctcccca gtccccatc tcagccagca    960 gaggcctcgg aggtggcggg tgggacccaa cctgcggctg gagcccagga gccaggggag   1020
acggcggcaa gtgaagcagc ctccagctct cttcctgctg tcgtggtgga gaccttccca   1080
gcaactgtga atggcaccgt ggagggcggc agtggggccg gcgcttgga cctgccccca    1140 ggtttcatgt tcaaggtaca ggcccagcac gactacacgg ccactgacac agacgagctg   1200
cagctcaagg ctggtgatgt ggtgctggtg atccccttcc agaaccctga agagcaggat   1260
gaaggctggc tcatgggcgt gaaggagagc gactggaacc agcacaagga gctggagaag   1320
tgccgtggcg tcttccccga gaacttcact gagagggtcc catga                  1365
```

<210> SEQ ID NO 30
<211> LENGTH: 454
<212> TYPE: PRT
<213> ORGANISM: Homo sapiens

<400> SEQUENCE: 30

```
Met Ala Glu Met Gly Ser Lys Gly Val Thr Ala Gly Lys Ile Ala Ser
1               5                   10                  15

Asn Val Gln Lys Lys Leu Thr Arg Ala Gln Glu Lys Val Leu Gln Lys
            20                  25                  30

Leu Gly Lys Ala Asp Glu Thr Lys Asp Glu Gln Phe Glu Gln Cys Val
        35                  40                  45

Gln Asn Phe Asn Lys Gln Leu Thr Glu Gly Thr Arg Leu Gln Lys Asp
    50                  55                  60

Leu Arg Thr Tyr Leu Ala Ser Val Lys Ala Met His Glu Ala Ser Lys
65                  70                  75                  80

Lys Leu Asn Glu Cys Leu Gln Glu Val Tyr Glu Pro Asp Trp Pro Gly
                85                  90                  95

Arg Asp Glu Ala Asn Lys Ile Ala Glu Asn Asn Asp Leu Leu Trp Met
            100                 105                 110

Asp Tyr His Gln Lys Leu Val Asp Gln Ala Leu Leu Thr Met Asp Thr
        115                 120                 125

Tyr Leu Gly Gln Phe Pro Asp Ile Lys Ser Arg Ile Ala Lys Arg Gly
    130                 135                 140

Arg Lys Leu Val Asp Tyr Asp Ser Ala Arg His His Tyr Glu Ser Leu
145                 150                 155                 160

Gln Thr Ala Lys Lys Lys Asp Glu Ala Lys Ile Ala Lys Ala Glu Glu
                165                 170                 175

Glu Leu Ile Lys Ala Gln Lys Val Phe Glu Glu Met Asn Val Asp Leu
            180                 185                 190

Gln Glu Glu Leu Pro Ser Leu Trp Asn Ser Arg Val Gly Phe Tyr Val
        195                 200                 205

Asn Thr Phe Gln Ser Ile Ala Gly Leu Glu Glu Asn Phe His Lys Glu
    210                 215                 220

Met Ser Lys Leu Asn Gln Asn Leu Asn Asp Val Leu Val Gly Leu Glu
225                 230                 235                 240

Lys Gln His Gly Ser Asn Thr Phe Thr Val Lys Ala Gln Pro Arg Lys
                245                 250                 255

Lys Ser Lys Leu Phe Ser Arg Leu Arg Arg Lys Lys Asn Ser Asp Asn
            260                 265                 270

Ala Pro Ala Lys Gly Asn Lys Ser Pro Ser Pro Pro Asp Gly Ser Pro
        275                 280                 285
```

```
Ala Ala Thr Pro Glu Ile Arg Val Asn His Glu Pro Glu Pro Ala Gly
            290                 295                 300
Gly Ala Thr Pro Gly Ala Thr Leu Pro Lys Ser Pro Ser Gln Pro Ala
305                 310                 315                 320
Glu Ala Ser Glu Val Ala Gly Gly Thr Gln Pro Ala Ala Gly Ala Gln
                325                 330                 335
Glu Pro Gly Glu Thr Ala Ala Ser Glu Ala Ala Ser Ser Ser Leu Pro
            340                 345                 350
Ala Val Val Val Glu Thr Phe Pro Ala Thr Val Asn Gly Thr Val Glu
        355                 360                 365
Gly Gly Ser Gly Ala Gly Arg Leu Asp Leu Pro Pro Gly Phe Met Phe
    370                 375                 380
Lys Val Gln Ala Gln His Asp Tyr Thr Ala Thr Asp Thr Asp Glu Leu
385                 390                 395                 400
Gln Leu Lys Ala Gly Asp Val Val Leu Val Ile Pro Phe Gln Asn Pro
                405                 410                 415
Glu Glu Gln Asp Glu Gly Trp Leu Met Gly Val Lys Glu Ser Asp Trp
            420                 425                 430
Asn Gln His Lys Glu Leu Glu Lys Cys Arg Gly Val Phe Pro Glu Asn
        435                 440                 445
Phe Thr Glu Arg Val Pro
    450

<210> SEQ ID NO 31
<211> LENGTH: 1230
<212> TYPE: DNA
<213> ORGANISM: artificial
<220> FEATURE:
<223> OTHER INFORMATION: artificial cDNA sequence with exons 1 to 6; 8
      to 10; 12 and 18-20 - named short isoform 9

<400> SEQUENCE: 31
atggcagaga tgggcagtaa aggggtgacg gcgggaaaga tcgccagcaa cgtgcagaag        60
aagctcaccc gcgcgcagga gaaggttctc cagaagctgg ggaaggcaga tgagaccaag       120
gatgagcagt tgagcagtg cgtccagaat tcaacaagc agctgacgga gggcaccccgg       180 ctgcagaagg atctccggac ctacctggcc tccgtcaaag ccatgcacga ggcttccaag       240
aagctgaatg agtgtctgca ggaggtgtat gagcccgatt ggcccggcag ggatgaggca       300
aacaagatcg cagagaacaa cgacctgctg tggatggatt accaccagaa gctggtggac       360
caggcgctgc tgaccatgga cacgtacctg ggccagttcc ccgacatcaa gtcacgcatt       420
gccaagcggg ggcgcaagct ggtggactac gacagtgccc ggcaccacta cgagtccctt       480
caaactgcca aaagaagga tgaagccaaa attgccaagg ccgaggagga gctcatcaaa       540
gcccagaagg tgtttgagga tgaatgtgt gatctgcagg aggagctgcc gtccctgtgg        600
aacagccgcg taggtttcta cgtcaacacg ttccagagca tcgcgggcct ggaggaaaac       660
ttccacaagg agatgagcaa gctcaaccag aacctcaatg atgtgctggt cggcctggag       720
aagcaacacg ggagcaacac cttcacggtc aaggcccagc ccagtgacaa cgcgcctgca       780
aaagggaaca agagcccttc gcctccagat ggctcccctg ccgccacccc cgagatcaga       840
gtcaaccacg agccagagcc ggccggcggg gccacgcccg ggccacccct ccccaagtcc       900
ccatctcaga gctctcttcc tgctgtcgtg gtggagacct tcccagcaac tgtgaatggc       960
accgtggagc gcggcagtgg ggccgggcgc ttggacctgc cccaggtttt catgttcaag      1020
gtacaggccc agcacgacta cacggccact gacacagacg agctgcagct caaggctggt      1080
```

```
gatgtggtgc tggtgatccc cttccagaac cctgaagagc aggatgaagg ctggctcatg    1140
ggcgtgaagg agagcgactg gaaccagcac aaggagctgg agaagtgccg tggcgtcttc    1200
cccgagaact tcactgagag ggtcccatga                                     1230
```

<210> SEQ ID NO 32
<211> LENGTH: 409
<212> TYPE: PRT
<213> ORGANISM: artificial
<220> FEATURE:
<223> OTHER INFORMATION: aminoacid sequence corresponding to cDNA
      sequence with exons 1 to 6, 8 to 10, 12, and 18 to 20 - named
      short isoform 9

<400> SEQUENCE: 32

```
Met Ala Glu Met Gly Ser Lys Gly Val Thr Ala Gly Lys Ile Ala Ser
1               5                   10                  15

Asn Val Gln Lys Lys Leu Thr Arg Ala Gln Glu Lys Val Leu Gln Lys
            20                  25                  30

Leu Gly Lys Ala Asp Glu Thr Lys Asp Glu Gln Phe Glu Gln Cys Val
        35                  40                  45

Gln Asn Phe Asn Lys Gln Leu Thr Glu Gly Thr Arg Leu Gln Lys Asp
    50                  55                  60

Leu Arg Thr Tyr Leu Ala Ser Val Lys Ala Met His Glu Ala Ser Lys
65                  70                  75                  80

Lys Leu Asn Glu Cys Leu Gln Glu Val Tyr Glu Pro Asp Trp Pro Gly
                85                  90                  95

Arg Asp Glu Ala Asn Lys Ile Ala Glu Asn Asn Asp Leu Leu Trp Met
            100                 105                 110

Asp Tyr His Gln Lys Leu Val Asp Gln Ala Leu Leu Thr Met Asp Thr
        115                 120                 125

Tyr Leu Gly Gln Phe Pro Asp Ile Lys Ser Arg Ile Ala Lys Arg Gly
    130                 135                 140

Arg Lys Leu Val Asp Tyr Asp Ser Ala Arg His His Tyr Glu Ser Leu
145                 150                 155                 160

Gln Thr Ala Lys Lys Lys Asp Glu Ala Lys Ile Ala Lys Ala Glu Glu
                165                 170                 175

Glu Leu Ile Lys Ala Gln Lys Val Phe Glu Glu Met Asn Val Asp Leu
            180                 185                 190

Gln Glu Glu Leu Pro Ser Leu Trp Asn Ser Arg Val Gly Phe Tyr Val
        195                 200                 205

Asn Thr Phe Gln Ser Ile Ala Gly Leu Glu Glu Asn Phe His Lys Glu
    210                 215                 220

Met Ser Lys Leu Asn Gln Asn Leu Asn Asp Val Leu Val Gly Leu Glu
225                 230                 235                 240

Lys Gln His Gly Ser Asn Thr Phe Thr Val Lys Ala Gln Pro Ser Asp
                245                 250                 255

Asn Ala Pro Ala Lys Gly Asn Lys Ser Pro Ser Pro Asp Gly Ser
            260                 265                 270

Pro Ala Ala Thr Pro Glu Ile Arg Val Asn His Glu Pro Glu Pro Ala
        275                 280                 285

Gly Gly Ala Thr Pro Gly Ala Thr Leu Pro Lys Ser Pro Ser Gln Ser
    290                 295                 300

Ser Leu Pro Ala Val Val Val Glu Thr Phe Pro Ala Thr Val Asn Gly
305                 310                 315                 320
```

```
Thr Val Glu Gly Gly Ser Gly Ala Gly Arg Leu Asp Leu Pro Pro Gly
            325                 330                 335

Phe Met Phe Lys Val Gln Ala Gln His Asp Tyr Thr Ala Thr Asp Thr
        340                 345                 350

Asp Glu Leu Gln Leu Lys Ala Gly Asp Val Val Leu Val Ile Pro Phe
            355                 360                 365

Gln Asn Pro Glu Glu Gln Asp Glu Gly Trp Leu Met Gly Val Lys Glu
        370                 375                 380

Ser Asp Trp Asn Gln His Lys Glu Leu Glu Lys Cys Arg Gly Val Phe
385                 390                 395                 400

Pro Glu Asn Phe Thr Glu Arg Val Pro
            405

<210> SEQ ID NO 33
<211> LENGTH: 20
<212> TYPE: DNA
<213> ORGANISM: Artificial Sequence
<220> FEATURE:
<223> OTHER INFORMATION: Primer BIN1

<400> SEQUENCE: 33
acggcgggaa agatcgccag                                              20

<210> SEQ ID NO 34
<211> LENGTH: 20
<212> TYPE: DNA
<213> ORGANISM: Artificial Sequence
<220> FEATURE:
<223> OTHER INFORMATION: Primer BIN1

<400> SEQUENCE: 34
ttgtgctggt tccagtcgct                                              20

<210> SEQ ID NO 35
<211> LENGTH: 14
<212> TYPE: PRT
<213> ORGANISM: Artificial sequence
<220> FEATURE:
<223> OTHER INFORMATION: peptide tagged PMO
<220> FEATURE:
<221> NAME/KEY: MISC_FEATURE
<222> LOCATION: (1)..(1)
<223> OTHER INFORMATION: Acetylamino
<220> FEATURE:
<221> NAME/KEY: MISC_FEATURE
<222> LOCATION: (2)..(2)
<223> OTHER INFORMATION: Xaa = 6-aminohexanoic acid
<220> FEATURE:
<221> NAME/KEY: MISC_FEATURE
<222> LOCATION: (5)..(5)
<223> OTHER INFORMATION: beta-alanine
<220> FEATURE:
<221> NAME/KEY: MISC_FEATURE
<222> LOCATION: (8)..(8)
<223> OTHER INFORMATION: Xaa = 6-aminohexanoic acid
<220> FEATURE:
<221> NAME/KEY: MISC_FEATURE
<222> LOCATION: (11)..(11)
<223> OTHER INFORMATION: beta-alanine
<220> FEATURE:
<221> NAME/KEY: MISC_FEATURE
<222> LOCATION: (13)..(13)
<223> OTHER INFORMATION: Xaa = 6-aminohexanoic acid
<220> FEATURE:
<221> NAME/KEY: MISC_FEATURE
<222> LOCATION: (14)..(14)
<223> OTHER INFORMATION: beta-alanine
```

```
<400> SEQUENCE: 35

Arg Xaa Arg Arg Ala Arg Arg Xaa Arg Arg Ala Arg Xaa Ala
1               5                   10
```

The invention claimed is:

1. A method of improving motor and/or muscular function and/or prolonging lifespan in a subject with an X-linked centronuclear myopathy (XLCNM), comprising administering an amphiphysin 2 polypeptide or a BIN1 nucleic acid to the subject.

2. The method according to claim 1, wherein the BIN1 nucleic acid comprises a sequence comprising any combination of at least two or three different BIN1 exons 1 to 20 represented by SEQ ID NO: 3 to 22, respectively.

3. The method according to claim 1, wherein the BIN1 nucleic acid comprises a sequence comprising any combination of at least two or three different BIN1 exons 1 to 20 represented by SEQ ID NO: 3 to 22, respectively, and according to increasing numbering of exons 1 to 20.

4. The method according to claim 1, wherein the BIN1 nucleic acid comprises any one of the sequences SEQ ID NO: 1, 23, 25, 27, 29, or 31, or sequence that hybridizes or is complementary thereto.

5. The method according to claim 1, wherein the amphiphysin 2 polypeptide comprises a sequence derived from or encoded by any combination of at least two or three different BIN1 exons 1 to 20, represented by SEQ ID NO: 3 to 22, respectively.

6. The method according to claim 1, wherein the amphiphysin 2 polypeptide comprises a sequence derived from or encoded by any combination of at least two or three different BIN1 exons 1 to 20, represented by SEQ ID NO: 3 to 22, respectively, and according to increasing numbering of exons 1 to 20.

7. The method according to claim 1, wherein the amphiphysin 2 polypeptide comprises any one of the sequences SEQ ID NO: 2, 24, 26, 28, 30 or 32, or a bioactive fragment or variant thereof having at least 80% sequence identity thereto.

8. The method according to claim 1, said method improving motor function in the subject with XLCNM.

9. The method according to claim 1, said method improving muscular function in the subject with XLCNM.

10. The method according to claim 1, said method prolonging lifespan in the subject with XLCNM.

11. The method according to claim 1, said method improving motor and muscular function and prolonging lifespan in the subject with XLCNM.

* * * * *

UNITED STATES PATENT AND TRADEMARK OFFICE
CERTIFICATE OF CORRECTION

PATENT NO. : 11,666,628 B2
APPLICATION NO. : 16/762953
DATED : June 6, 2023
INVENTOR(S) : Jocelyn Laporte, Valentina Lionello and Belinda Cowling It is certified that error appears in the above-identified patent and that said Letters Patent is hereby corrected as shown below:

In the Specification

Column 4,
Line 21, "(n ǂ 5)" should read --(n ≥ 5)--.
Line 22, "(n ǂ 5)." should read --(n ≥ 5).--.
Line 22, "force (n ǂ 5)" should read --force (n ≥ 5)--.
Line 32, "(n ǂ 2)" should read --(n ≥ 2)--.
Line 49, "(n ǂ 5)." should read --(n ≥ 5).--.
Line 49, "(n ǂ 4)." should read --(n ≥ 4).--.
Line 50, "(n ǂ 4)." should read --(n ≥ 4).--.
Line 53, "(n ǂ 3)." should read --(n ≥ 3).--.

Column 5,
Line 30, "(n ǂ 25 from" should read --(n ≥ 25 from--.
Line 32, "(n ǂ 0 from" should read --(n ≥ 0 from--.

Column 6,
Lines 7-8, "of -20% or -10%," should read --of ±20% or ±10%,--.
Lines 8-9, "-5%, even more preferably -1%, and still more preferably -0.1%" should read --±5%, even more preferably ±1%, and still more preferably ±0.1%--.

Column 16,
Line 57, "b-alanine)" should read --β-alanine)--.

Signed and Sealed this
First Day of October, 2024

Katherine Kelly Vidal
*Director of the United States Patent and Trademark Office*